United States Patent
Indermuhle et al.

(10) Patent No.: US 12,306,093 B2
(45) Date of Patent: May 20, 2025

(54) METHODS AND SYSTEMS FOR INTEGRATED ON-CHIP SINGLE-MOLECULE DETECTION

(71) Applicant: Nautilus Subsidiary, Inc., Seattle, WA (US)

(72) Inventors: Pierre Indermuhle, Berkeley, CA (US); Elliott Sorelle, San Carlos, CA (US); David Stern, San Carlos, CA (US); Parag Mallick, San Mateo, CA (US); Sujal M. Patel, Seattle, WA (US)

(73) Assignee: Nautilus Subsidiary, Inc., Seattle, WA (US)

( * ) Notice: Subject to any disclaimer, the term of this patent is extended or adjusted under 35 U.S.C. 154(b) by 819 days.

(21) Appl. No.: 17/513,877

(22) Filed: Oct. 28, 2021

(65) Prior Publication Data
US 2022/0050049 A1    Feb. 17, 2022

Related U.S. Application Data

(63) Continuation of application No. PCT/US2020/030501, filed on Apr. 29, 2020.

(60) Provisional application No. 62/840,209, filed on Apr. 29, 2019.

(51) Int. Cl.
*G01N 21/25* (2006.01)
*C12Q 1/6837* (2018.01)
*G01N 21/64* (2006.01)
*G01N 33/543* (2006.01)
*G01N 21/77* (2006.01)

(52) U.S. Cl.
CPC ......... *G01N 21/255* (2013.01); *C12Q 1/6837* (2013.01); *G01N 21/6428* (2013.01); *G01N 33/54366* (2013.01); *G01N 2021/6439* (2013.01); *G01N 2021/7793* (2013.01)

(58) Field of Classification Search
CPC ............. G01N 21/255; G01N 21/6428; G01N 33/54366; G01N 2021/6439; G01N 2021/7793; G01N 33/5308; C12Q 1/6837; C12Q 1/6825; C12Q 2565/607; C12Q 2563/107; C12Q 2565/518
See application file for complete search history.

(56) References Cited

U.S. PATENT DOCUMENTS

| | | | |
|---|---|---|---|
| 5,324,633 A | 6/1994 | Fodor et al. | |
| 5,445,934 A | 8/1995 | Fodor et al. | |
| 5,695,934 A | 12/1997 | Brenner | |
| 5,849,878 A | 12/1998 | Cantor et al. | |
| 5,863,722 A | 1/1999 | Brenner | |
| 5,888,737 A | 3/1999 | DuBridge et al. | |
| 5,919,626 A | 7/1999 | Shi et al. | |
| 6,140,489 A | 10/2000 | Brenner | |
| 6,175,002 B1 | 1/2001 | DuBridge et al. | |
| 6,255,469 B1 | 7/2001 | Seeman et al. | |
| 6,391,625 B1 | 5/2002 | Park et al. | |
| 6,589,726 B1 | 7/2003 | Butler et al. | |
| 6,610,482 B1 | 8/2003 | Fodor et al. | |
| 6,720,595 B2 | 4/2004 | Clevenger et al. | |
| 6,737,236 B1 | 5/2004 | Pieken et al. | |
| 6,806,361 B1 | 10/2004 | Kajisa et al. | |
| 6,824,866 B1 | 11/2004 | Glazer et al. | |
| 6,998,241 B2 | 2/2006 | Boga | |
| 7,022,515 B2 | 4/2006 | Herron et al. | |
| 7,148,058 B2 | 12/2006 | Charych et al. | |
| 7,158,224 B2 | 1/2007 | Montagu | |
| 7,239,860 B2 | 7/2007 | Stoks | |
| 7,252,954 B2 | 8/2007 | Wang et al. | |
| 7,259,258 B2 | 8/2007 | Kozlov et al. | |
| 7,375,234 B2 | 5/2008 | Sharpless et al. | |
| 7,427,678 B2 | 9/2008 | Pieken et al. | |
| 7,545,496 B2 | 6/2009 | Prins et al. | |
| 7,598,363 B2 | 10/2009 | Seeman et al. | |
| 7,635,562 B2 | 12/2009 | Harris et al. | |
| 7,763,736 B2 | 7/2010 | Sharpless et al. | |
| 7,794,799 B1 | 9/2010 | Kim et al. | |
| 7,842,793 B2 | 11/2010 | Rothemund | |
| 7,932,060 B2 | 4/2011 | Nadeau et al. | |
| 8,133,719 B2 | 3/2012 | Drmanac et al. | |
| 8,445,194 B2 | 5/2013 | Drmanac et al. | |
| 8,467,061 B2 | 6/2013 | McCAFFREY et al. | |
| 8,501,923 B2 | 8/2013 | Rothemund | |
| 8,680,483 B2 | 3/2014 | Haga et al. | |
| 8,865,077 B2 | 10/2014 | Chiou et al. | |

(Continued)

FOREIGN PATENT DOCUMENTS

| | | |
|---|---|---|
| CN | 100500865 C | 6/2009 |
| EP | 1105529 B2 | 5/2013 |
| EP | 2872898 B1 | 12/2016 |
| EP | 3498865 B1 | 10/2020 |

(Continued)

OTHER PUBLICATIONS

Office Action in CA3135206, mailed Aug. 29, 2023, 5 pages.

(Continued)

*Primary Examiner* — Narayan K Bhat
(74) *Attorney, Agent, or Firm* — Orrick, Herrington & Sutcliffe, LLP

(57) ABSTRACT

The present disclosure provides methods and systems for performing single-molecule detection using fabricated integrated on-chip devices. Provided herein is a composition, comprising: (a) a substrate; (b) a structured nucleic acid particle coupled to the substrate, wherein a biological entity is coupled to the structured nucleic acid particle; and (c) a fluorescent detection agent, wherein the fluorescent detection agent comprises an affinity reagent attached to another structured nucleic acid particle, wherein the affinity reagent is bound to the biological entity.

24 Claims, 10 Drawing Sheets

(56) References Cited

U.S. PATENT DOCUMENTS

| | | |
|---|---|---|
| 8,951,781 B2 | 2/2015 | Reed et al. |
| 9,193,996 B2 | 11/2015 | Buermann et al. |
| 9,275,871 B2 | 3/2016 | Sandhu |
| 9,330,932 B1 | 5/2016 | Sills et al. |
| 9,340,416 B2 | 5/2016 | Maune et al. |
| 9,466,504 B1 | 10/2016 | Sills et al. |
| 9,528,984 B2 | 12/2016 | Mitra |
| 9,606,058 B2 | 3/2017 | Rothberg et al. |
| 9,678,012 B2 | 6/2017 | Rothberg et al. |
| 9,717,685 B2 | 8/2017 | Shih et al. |
| 9,796,749 B2 | 10/2017 | Yin et al. |
| 9,880,175 B2 | 1/2018 | Mitra |
| 9,921,157 B2 | 3/2018 | Rothberg et al. |
| 9,975,916 B2 | 5/2018 | Yin et al. |
| 10,099,920 B2 | 10/2018 | Shen et al. |
| 10,175,248 B2 | 1/2019 | Mitra |
| 10,330,598 B2 | 6/2019 | Schleipen et al. |
| 10,351,909 B2 | 7/2019 | Drmanac et al. |
| 10,473,654 B1 | 11/2019 | Mallick |
| 10,550,145 B2 | 2/2020 | Han et al. |
| 10,571,473 B2 | 2/2020 | Mitra |
| 10,604,543 B2 | 3/2020 | Yin et al. |
| 10,605,730 B2 | 3/2020 | Rothberg et al. |
| 10,712,274 B2 | 7/2020 | Rothberg et al. |
| 10,741,382 B2 | 8/2020 | Sills et al. |
| 10,775,305 B2 | 9/2020 | Rothberg et al. |
| 10,829,816 B2 | 11/2020 | Staker et al. |
| 10,845,308 B2 | 11/2020 | Rothberg et al. |
| 10,895,534 B2 | 1/2021 | Finkelstein et al. |
| 10,921,317 B2 | 2/2021 | Mallick |
| 10,948,488 B2 | 3/2021 | Mallick |
| 11,125,748 B2 | 9/2021 | Gopinath et al. |
| 11,203,612 B2 * | 12/2021 | Gremyachinskiy ......................... G01N 33/54353 |
| 11,603,383 B2 * | 3/2023 | Gremyachinskiy .. C12Q 1/6837 |
| 11,692,217 B2 * | 7/2023 | Aksel .................. C12Q 1/6832 435/6.11 |
| 11,935,311 B2 * | 3/2024 | Egertson ............... C12Q 1/6834 |
| 11,993,807 B2 * | 5/2024 | Aksel .................. C12Q 1/6876 |
| 2003/0049626 A1 | 3/2003 | Jendoubi |
| 2003/0054408 A1 | 3/2003 | Ravi et al. |
| 2003/0143569 A1 | 7/2003 | Abrams |
| 2003/0170613 A1 | 9/2003 | Straus |
| 2004/0023413 A1 | 2/2004 | Opalsky |
| 2004/0091931 A1 | 5/2004 | Gold |
| 2004/0209383 A1 | 10/2004 | Yin et al. |
| 2005/0054118 A1 | 3/2005 | Lebrun |
| 2005/0095577 A1 | 5/2005 | Yang et al. |
| 2005/0287523 A1 | 12/2005 | Letant et al. |
| 2006/0035220 A1 | 2/2006 | Tashiro et al. |
| 2006/0160234 A1 | 7/2006 | Lopez-Avila et al. |
| 2006/0263769 A1 | 11/2006 | Luo et al. |
| 2007/0003959 A1 | 1/2007 | Ehben et al. |
| 2007/0188750 A1 | 8/2007 | Lundquist et al. |
| 2007/0218503 A1 | 9/2007 | Mitra |
| 2008/0032310 A1 | 2/2008 | Shannon et al. |
| 2009/0018028 A1 | 1/2009 | Lindsay et al. |
| 2009/0161100 A1 | 6/2009 | Minot et al. |
| 2009/0214591 A1 | 8/2009 | Manucharyan et al. |
| 2009/0247414 A1 | 10/2009 | Obradovic et al. |
| 2009/0311774 A1 | 12/2009 | Chiou et al. |
| 2010/0069621 A1 | 3/2010 | Maune et al. |
| 2010/0081134 A1 | 4/2010 | Mirkin et al. |
| 2010/0111768 A1 | 5/2010 | Banerjee et al. |
| 2010/0129819 A1 | 5/2010 | Hu et al. |
| 2010/0151472 A1 | 6/2010 | Nolan et al. |
| 2011/0065807 A1 | 3/2011 | Radovic-Moreno et al. |
| 2011/0263688 A1 | 10/2011 | Barany et al. |
| 2012/0077688 A1 | 3/2012 | Bergo et al. |
| 2012/0141502 A1 | 6/2012 | Dixon et al. |
| 2013/0224859 A1 | 8/2013 | Bachelet |
| 2014/0087963 A1 | 3/2014 | Johnston et al. |
| 2015/0004193 A1 | 1/2015 | Chang et al. |
| 2015/0104880 A1 | 4/2015 | Tagawa et al. |
| 2015/0160204 A1 | 6/2015 | Mitra |
| 2015/0185199 A1 | 7/2015 | Joo et al. |
| 2015/0330974 A1 | 11/2015 | Staker et al. |
| 2016/0046984 A1 | 2/2016 | Nguyen et al. |
| 2016/0060687 A1 | 3/2016 | Zhu et al. |
| 2016/0102344 A1 | 4/2016 | Niemeyer et al. |
| 2016/0160272 A1 | 6/2016 | Mir |
| 2016/0161472 A1 | 6/2016 | Jungmann |
| 2016/0167413 A1 | 6/2016 | Furuya |
| 2016/0310926 A1 | 10/2016 | Sun et al. |
| 2017/0044245 A1 | 2/2017 | Meng et al. |
| 2017/0081713 A1 | 3/2017 | Kim et al. |
| 2017/0191051 A1 | 7/2017 | Nikiforov |
| 2017/0283868 A1 | 10/2017 | Beechem et al. |
| 2017/0327888 A1 | 11/2017 | Ong et al. |
| 2017/0356030 A1 | 12/2017 | Boyanov et al. |
| 2018/0044663 A1 | 2/2018 | Yan |
| 2018/0148514 A1 | 5/2018 | Williams |
| 2019/0032050 A1 | 1/2019 | Guo et al. |
| 2019/0233880 A1 | 4/2019 | Mir |
| 2019/0195869 A1 | 6/2019 | Fan et al. |
| 2019/0323002 A1 | 10/2019 | Gopinath et al. |
| 2019/0352342 A1 | 11/2019 | Cocquerel-Deproy et al. |
| 2020/0025752 A1 | 1/2020 | Gopinath et al. |
| 2020/0025757 A1 | 1/2020 | Gopinath et al. |
| 2020/0082914 A1 | 3/2020 | Patel et al. |
| 2020/0090785 A1 | 3/2020 | Patel et al. |
| 2020/0232994 A1 | 7/2020 | Mitra |
| 2020/0286584 A9 | 9/2020 | Patel et al. |
| 2020/0318101 A1 | 10/2020 | Mallick et al. |
| 2021/0278400 A1 | 1/2021 | Mallick |
| 2021/0032775 A1 | 2/2021 | Golpinath et al. |
| 2021/0101930 A1 | 4/2021 | Gremyachinskiy et al. |
| 2021/0132053 A1 | 5/2021 | Chandradoss et al. |
| 2021/0223238 A1 | 7/2021 | Mallick |
| 2021/0239705 A1 | 8/2021 | Mallick |
| 2021/0355483 A1 | 11/2021 | Chee et al. |
| 2022/0017567 A1 | 1/2022 | Gremyachinskiy et al. |
| 2022/0050049 A1 | 2/2022 | Indermuhle et al. |
| 2022/0333215 A1 | 10/2022 | Xu et al. |
| 2023/0221243 A1 | 7/2023 | Indermuhle et al. |

FOREIGN PATENT DOCUMENTS

| | | |
|---|---|---|
| WO | WO-0146675 A2 | 6/2001 |
| WO | WO-02086081 A2 | 10/2002 |
| WO | WO 2005/065814 A1 | 7/2005 |
| WO | WO-2006135527 A2 | 12/2006 |
| WO | WO-2007117444 A2 | 10/2007 |
| WO | WO-2008016644 A1 | 2/2008 |
| WO | WO-2007120208 A3 | 8/2008 |
| WO | WO-2007123744 A3 | 11/2008 |
| WO | WO-2009012343 A2 | 1/2009 |
| WO | WO-2010065531 A1 | 6/2010 |
| WO | WO-2014078855 A1 | 5/2014 |
| WO | WO-2015097077 A2 | 7/2015 |
| WO | WO-2016174525 A1 | 11/2016 |
| WO | WO-2017127762 A1 | 7/2017 |
| WO | WO-2018102759 A1 | 6/2018 |
| WO | WO-2019036055 A2 | 2/2019 |
| WO | WO-2019059961 A1 | 3/2019 |
| WO | WO-2019133892 A1 | 7/2019 |
| WO | WO-2019195633 | 10/2019 |
| WO | WO 2019/211631 A1 | 11/2019 |
| WO | WO-2019236749 A2 | 12/2019 |
| WO | WO-2020106889 A1 | 5/2020 |
| WO | WO-2020108588 A1 | 6/2020 |
| WO | WO-2020223368 A1 | 11/2020 |
| WO | WO-2021074087 A1 | 4/2021 |
| WO | WO 2021/087402 A1 | 5/2021 |
| WO | WO 2020/254684 A1 | 12/2021 |

OTHER PUBLICATIONS

Anonymous. List of protein hydrodynamic diameters. Dynamic Biosensors. May 17, 2017, XP055857934, Available at https://www.dynamic-biosensors.com/project/list-of-protein-hydrodynamic-diameters/. Retrieved on Nov. 4, 2021.

(56) References Cited

OTHER PUBLICATIONS

Co-pending U.S. Appl. No. 17/534,405, inventor Mallick; Parag, filed on Nov. 23, 2021.
EP19781106.0 Extended European Search Report dated Nov. 19, 2021.
Hung, Albert M., et al. Large-area spatially ordered arrays of gold nanoparticles directed by lithographically confined DNA origami. Nature nanotechnology 5.2 (2010): 121-126.
Rusmini, Federica et al. Protein immobilization strategies for protein biochips. Biomacromolecules vol. 8,6 (2007): 1775-89. doi:10.1021/bm061197b.
U.S. Appl. No. 16/791,456 Final Office Action dated Jan. 21, 2022.
U.S. Appl. No. 17/390,666 Office Action dated Jan. 28, 2022.
Extended European Search Report for Application No. 20798234.9, 10 pages, Jun. 19, 2023.
Chandrasekaran, "Programmable DNA scaffolds for spatially-ordered protein assembly", Nanoscale, vol. 8, No. 8, Jan. 1, 2016, pp. 4436-4446, United Kingdom.
Nangreave et al., "DNA origami: a history and current perspective", Current Opinion in Chemical Biology, 2010, 14:608-615; available online Jul. 17, 2010.
Rinker et al., "Self-assembled DNA nanostructures for distance-dependent multivalent ligand- protein binding", Nature Nanotechnology, vol. 3, Jul. 2008, pp. 418-422, published online Jun. 22, 2008.
Asseline, U. et al. "Development and Applications of Fluorescent Oligonucleotides" Curr. Org. Chem. (2006) 10:491-518.
Bauer et al., "Anything You Can Do, I Can Do Better: Can Aptamers Replace Antibodies in Clinical Diagnostic Applications?", Molecules 24:4377 (2019).
Bruno, "Predicting the Uncertain Future of Aptamer-Based Diagnostics and Therapeutics", Molecules2015, 20, 6866-6887; doi:10.3390/molecules20046866.
Chen et al., "Protein Microarrays", BioTechniques, vol. 40, Issue 4, Apr. 2006, pp. 423-429.
Choi, Youngeun et al. "A new reporter design based on DNA origami nanostructures for quantification of short oligonucleotides using microbeads", Scientific Reports, vol. 9, No. 1, Mar. 18, 2019.
Clever, G.H. et al. "DNA-Metal Base Pairs" Angew. Chem. Int. Ed. (2007) 46:6226-6236.
Cox, W.G. et al. "Fluorescent DNA Hybridization Probe Preparation Using Amine Modification and Reactive Dye Coupling" Biotechniques (2004) 36:114-122.
Evanko, D. et al. "Hybridization Chain Reaction" Nat. Methods (2004) 1:186-187.
Galimidi, R.P. et al. "Intra-Spike Crosslinking Overcomes Antibody Evasion by HIV-1" Cell (2015) 160:433-446.
Gardner, A.F. et al. "Therminator DNA Polymerase: Modified Nucleotides and Unnatural Substrates" Front. Mol. Biosci. (2019) 6:28.
Garmendia, C. et al. "The Bacteriophage Phi29 DNA Polymerase, a Proofreading Enzyme" J. Bio. Chem. (1992) 267:2594-2599.
Gyssels, E. et al. "Interstrand Cross-Linking of Nucleic Acids: From History to Recent and Future Applications" Modified Nucleic Acids in Biology and Medicine (2016) pp. 339-369.
He et al., "In situ synthesis of protein arrays", Current Opinions in Biotechnology 19: 4-9 (2008).
He, et al. Fluorescence aptameric sensor for strand displacement amplification detection of cocaine. Analytical chemistry 82.4 (2010): 1358-1364.
Itzkovitz, S. et al. "Validating Transcripts with Probes and Imaging Technology" Nat. Methods (2011) 8:512-519.
Janssen, et al. Nucleic acids for ultra-sensitive protein detection. Sensors (Basel). Jan. 21, 2013;13(1):1353-84.
Krufczik, M. et al. "Combining Low Temperature Fluorescence DNA-Hybridization, Immunostaining, and Super-Resolution Localization Microscopy for Nano-Structure Analysis of ALU Elements and Their Influence on Chromatin Structure" Int. J. Mol. Sci. (2017) 18:1005-1020.

Li Weiping et al., "Multiplex electrochemical origami immunodevice based on cuboid silver-paper electrode and metal ions tagged nanoporous silver chitosan", (2014) Biosensors & Bioelectronics, vol. 56, pp. 167-173.
Lian et al., "Ultrasensitive detection of biomolecules with fluorescent dye-doped nanoparticles", Analytical Biochemistry, vol. 334, 2004, pp. 135-144.
Lundberg, E.P. et al. "A New Fixation Strategy for Addressable Nano-Network Building Blocks" Chem. Comm. (2010) 46:3714-3716.
Musumeci, et al. Fluorescence sensing using DNA aptamers in cancer research and clinical diagnostics. Cancers 9.12 (2017): 174.
Nakamura, S. et al. "Creation of DNA Array Structure Equipped with Heat Resistance by Ultrafast Photocrosslinking" J. Chem. Technol. Biotechnol. (2013) 89:1086-1090.
Nam et al., "Nanoparticle-Based Bio-Bar Codes for the Ultraseneitive Detection of Proteins", Science 301:1884, Sep. 26, 2003.
O'Flaherty, D.K. et al. "Site-Specific Covalent Capture of Human 06-alkylguanine-DNA-alkyltransferase Using Single-Stranded Intrastrand Cross-Linked DNA" Org. Biomol. Chem. (2016) 15:189-196.
Rajendran, A. et al. "Photo-Cross-Linking-Assisted Thermal Stability of DNA Origami Structures and Its Application for Higher-Temperature Self-Assembly" JACS (2011) 133:14488-14491.
Randolph, J.B. et al. "Stability, Specificity, and Fluorescence Brightness of Mulitply-Labeled Fluorescent DNA Probes" Nuc. Acids Res. (1997) 25:2923-2929.
Sacca et al., "Orthogonal Protein Decoration of DNA Origami", Agnew. Chem. Intl. Ed. 49:9378, 2010.
Sacca et al., "Orthogonal Protein Decoration of DNA Origami", Supporting Information, Agnew. Chem. Intl. Ed. 49:9378, 2010.
Sakamoto et al., "Magnetically Promoted Rapid Immunoreactions Using Functionalized Fluorescent Magnetic Beads: A Proof of Principle", Clinical Chemistry 60(4) : 610-620 et al. (2014).
Schweitzer et al. Immunoassays with rolling circle DNA amplification: a versatile platform for ultrasensitive antigen detection. Proceedings of the National Academy of Sciences. USA. 97(18) (Aug. 2000):10113-10119.
Sinkeldam, R.W. et al. "Fluorescent Analogs of Biomolecular Building Blocks: Design, Properties and Applications" Chem. Rev. (2010) 110:2579-2619.
Sun, H. et al. "Coumarin-Induced DNA Ligation, Rearrangement to DNA Interstrand Crosslinks, and Photorelease of Coumarin Moiety" Chem BioChem (2016) 17:1-9.
Tagawa, M. et al. "Stabilization of DNA Nanostructures by Photo-Cross-Linking" Soft Matter (2011) 7:10931-10934.
Tsourkas et al., "Hybridization kinetics and thermodynamics of molecular beacons", Nucleic Acids Research, 2003, vol. 31, No. 4, pp. 1319-1330.
Wang, L. et al. "DNA Nanostructures in Cell Biology and Medicine" DNA Nanotechnology for Bioanalysis (2017) pp. 99-127.
Wojcezewski et al., "Fluorescent Oligonucleotides- Versatile Tools as Probes and Primers for DNA and RNA Analysis", Snylett No. 10:1667-1678 (1999).
Zakeri, B. et al., "Peptide tag forming a rapid covalent bond to a protein, through engineering a bacterial adhesin" PNAS 109 (12): E690-E697 (2012).
Zlauddin et al., "Microarray of cells expressing defined cDNAs", Science, 411:107 (2001).
Jaekel, A. et al., "Manipulating Enzymes Properties with DNA Nanostructures" Molecules 24(20):3694 (2019).
Jensen, J.O. et al. "Nanoengineered Bioplatforms Based on DNA Origami [Point of View]" Proceedings of the IEEE 102:1046-1049 (2014).
Kolb, H.C. et al., "Click Chemistry: Diverse Chemical Function from a Few Good Reactions" Angewandte Chemie International Edition. 40 (11): 2004ñ2021 (2001).
Spicer, C.D. et al. "Achieving Controlled BiomoleculeñBiomaterial Conjugation" Chem. Rev. (2018) 118(16):7702-7743.
Stawicki, C.M. et al., "Modular fluorescent nanoparticle DNA probes for detection of peptides and proteins" Scientific Reports 11:19921 (2021) [doi.org/10.1038/s41598-021-99084-4].

(56) References Cited

OTHER PUBLICATIONS

Vauquelin, G. et al., "Exploring avidity: understanding the potential gains in functional affinity and target residence time of bivalent and heterobivalent ligands" British Journal of Pharmacology 168:1771-1785 (2013).
Zhang, P. et al., "Capturing transient antibody conformations with DNA origami epitopes" Nature Communications 11:3114 (2020).
Zhao, Z. et al., "Organizing DNA origami tiles into larger structures using preformed scaffold frames" NanoLetters 11:2997-3002 (2011).
3-Aminopropyl)triethoxysilane. Wikipedia.org. Apr. 5, 2019 (Apr. 5, 2019), entire document esp p. 1 (https://en.wikipedia.org/w/index.php?title=(3-Aminopropyl)triethoxysilaneoldid=891131780).
Arnold et al. "The majority of immunogenic epitopes generate CD44- T cells that are dependent on MHC class II-bound peptide-flanking residues," J Immunol, Jul. 15, 2002 (Jul. 15, 2002), vol. 169, No. 2, pp. 739-749.
Ayoglu, et al., Autoantibody Profiling in Multiple Sclerosis Using Arrays of Human Protein Fragments, Molecular & Cellular Proteomics, (12)9 Sep. 1, 2013 (Sep. 1, 2013), pp. 2657-2672, XP055294116, US ,ISSN: 1535-9476, DOI: 10.1074/mcp.M112.026757.
Blatch, et al. The tetratricopeptide repeat: a structural motif mediating protein-protein interactions. Bioessays Nov. 1999;21(11):932-939.
Buenrostro, et al. Quantitative analysis of RNA-protein interactions on a massively parallel array for mapping biophysical and evolutionary landscapes. Nat Biotechnol. Jun. 2014; 32(6): 562-568.
Bunka et al. "Production and characterization of RNA aptamers specific for amyloid fibril epitopes," J Biol Chem, Sep. 18, 2007 (Sep. 18, 2007), vol. 282, No. 47, pp. 34500-34509.
Buus, et al. High-resolution mapping of linear antibody epitopes using ultrahigh-density peptide microarrays. Molecular & Cellular Proteomics 11.12 (2012): 1790-1800.
Choung, et al. Determination of B-Cell Epitopes in Patients with Celiac Disease: Peptide Microarrays. PloS one vol. 11(1) e0147777. Jan. 29, 2016, doi:10.1371/journal.pone.0147777.
Co-pending U.S. Appl. No. 17/390,666, inventor Mallick; Parag, filed on Jul. 30, 2021.
Co-pending U.S. Appl. No. 17/424,435, inventors Klein; Joshua et al., filed on Jul. 20, 2021.
Co-pending U.S. Appl. No. 17/496,742, inventors Gremyachinskiy; Dmitriy et al., filed on Oct. 7, 2021.
Domenyuk, et al. Plasma Exosome Profiling of Cancer Patients by a Next Generation Systems Biology Approach. Sci Rep. 2017; 7: 42741.
EP17877076.4 The Extended European Search Report dated Aug. 11, 2020.
EP18846671.8 Extended European Search Report dated Apr. 23, 2021.
Fodor, et al. Light-Directed, Spatially Addressable Parallel Chemical Synthesis. Science , vol. 251, 767-773, 1991.
Ford et al. "Degenerate recognition of T cell epitopes: impact of T cell receptor reserve and stability of peptide:MHC complexes," Mol Immunol, Feb. 1, 2004 (Feb. 1, 2004), vol. 40, No. 14-15, pp. 1019-1025.
Hung, et al. Large-area spatially ordered arrays of gold nanoparticles directed by lithographically confined DNA origami. Nat Nanotechnol. Feb. 2010;5(2):121-6. doi: 10.1038/nnano.2009.450. Epub Dec. 20, 2009.
Hunniger, et al. Just in time-selection: A rapid semiautomated SELEX of DNA aptamers using magnetic separation and BEAMing. Anal Chem. Nov. 4, 2014;86(21):10940-7.
Kang, H. The prevention and handling of the missing data. Korean journal of anesthesiology vol. 64,5 (2013): 402-6. doi:10.4097/kjae.2013.64.5.402.
Laurenson, et al. Development of peptide aptamer microarrays for detection of HPV16oncoproteins in cell extracts, Analytical Biochemistry, Academic Press, Amsterdam, NL, vol. 410, No. 2, Oct. 30, 2010 (Oct. 30, 2010), pp. 161-170, XP028146256,ISSN: 0003-2697,DOI: 10.1016/J.AB.2010.10.038.
Lin et al. Development of a novel peptide microarray for large-scale epitope mapping of food allergens, Journal of Allergy and Clinical Immunology, Elsevier, Amsterdam, Nl, vol. 124, No. 2, Aug. 1, 2009 (Aug. 1, 2009), pp. 315-322.e3, XP026390934, ISSN: 0091-6749,DOI: 10.1016/J.JACI.2009.05.024.
Lutz, et al. Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.
McKay, et al. Click Chemistry in Complex Mixtures: Bioorthogonal Bioconjugation. Chem Biol. Sep. 18, 2014; 21(9): 1075-1101.
Meldal, et al. Cu-catalyzed azide-alkyne cycloaddition. Chem Rev. Aug. 2008;108(8):2952-3015. doi: 10.1021/cr0783479.
Nonobe et al. A tabu search approach to the constraint satisfaction problem as a general problem solver. Eur. J. Oper. Res. 106 (1998): 599-623.
Patronov et al. "Peptide binding prediction for the human class Ii Mhc allele HLA-DP2: a molecular docking approach," BMC Struct Biol, Jul. 14, 2011 (Jul. 14, 2011), vol. 11, No. 32, pp. 1-10.
PCT/US17/64322 International Search Report and Written Opinion dated Apr. 25, 2018.
PCT/US18/00364 International Search Report and Written Opinion dated Mar. 22, 2019.
PCT/US2019/025909 International Search Report and Written Opinion dated Jun. 14, 2019.
PCT/US2019/035654 International Search Report and Written Opinion dated Nov. 25, 2019.
PCT/US2019/062482 International Search Report and Written Opinion dated Mar. 3, 2020.
PCT/US2020/030501 International Search Report and Written Opinion dated Aug. 11, 2020.
Price, et al., On silica peptide microarrays for high-resolution mapping of antibody epitopes and diverse protein-protein interactions, Nature Medicine, vol. 18, No. 9, Aug. 19, 2012, pp. 1434-1440, XP055793803, New York ISSN: 1078-8956, DOI: 10.1038/nm.2913Retrieved from the Internet: URL:http://www.nature.com/articles/nm.2913.
Reineke, et al. Epitope mapping protocols. Preface. Methods in molecular biology (Clifton, N.J.) vol. 524 (2009): v-vi.
Reyes et al. "Critical role of HLA-DR11" binding peptides' peripheral flanking residues in fully-protective malaria vaccine development," Biochem Biophys Res Commun, May 23, 2017 (May 23, 2017), vol. 489, No. 3, pp. 339-345.
Riccelli, et al. Hybridization of single-stranded DNA targets to immobilized complementary DNA probes: comparison of hairpin versus linear capture probes. Nucleic acids research vol. 29,4 (2001): 996-1004. doi:10.1093/nar/29.4.996.
Richer, et al., Epitope identification from fixed-complexity random-sequence peptide microarrays, Molecular & cellular proteomics, vol. 14, No. 1, Nov. 3, 2014, pp. 136-147.
Rothemund, et al. Folding DNA to create nanoscale shapes and patterns. Nature. Mar. 16, 2006;440(7082):297-302.
Sant'Angelo et al. "Recognition of core and flanking amino acids of MHC class II-bound peptides by the T cell receptor," Eur J Immunol, Sep. 1, 2002 (Sep. 1, 2002), vol. 32, No. 9, pp. 2510-2520.
She, et al. Comprehensive and quantitative mapping of RNA-protein interactions across a transcribed eukaryotic genome. Proc Natl Acad Sci U S A. Apr. 4, 2017; 114(14): 3619-3624.
Sjoberg et al. Validation of affinity reagents using antigen microarrays, NEWBIOTECHNOLOGY, vol. 29, No. 5, Jun. 1, 2012 pp. 555-563, XP055793929,NLISSN: 1871-6784, DOI: 10.1016/j.nbt.2011.11.009.
Speltz, et al. Design of Protein-Peptide Interaction Modules for Assembling Supramolecular Structures in Vivo and in Vitro. ACS Chem Biol. Sep. 18, 2015;10(9):2108-15. doi: 10.1021/acschembio.5b00415. Epub Jul. 17, 2015.
Stöhr, et al. A 31-residue peptide induces aggregation of tau's microtubule-binding region in cells. Nat Chem. Sep. 2017; 9(9): 874-881. Published online Apr. 3, 2017.doi: 10.1038/nchem.2754.

(56) References Cited

OTHER PUBLICATIONS

Tessler, L. Digital Protein Analysis: Technologies for Protein Diagnostics and Proteomics through Single-Molecule Detection (2011). All Theses and Dissertations (ETDs). 346 https://openscholarship.wustl.edu/etd/346.
U.S. Appl. No. 16/659,132 Notice of Allowance dated Jan. 14, 2021.
U.S. Appl. No. 16/659,132 Office Action dated Oct. 8, 2020.
U.S. Appl. No. 16/788,536 Notice of Allowance dated Dec. 9, 2020.
U.S. Appl. No. 16/788,536 Office Action dated Mar. 10, 2020.
U.S. Appl. No. 16/788,536 Office Action dated Sep. 24, 2020.
U.S. Appl. No. 16/791,456 Office Action dated Jul. 6, 2021.
U.S. Appl. No. 17/062,405 Final Office Action dated Aug. 24, 2021.
U.S. Appl. No. 17/062,405 Notice of Allowance dated Sep. 30, 2021.
U.S. Appl. No. 17/062,405 Office Action dated Apr. 14, 2021.
U.S. Appl. No. 17/191,632 Examiner's Interview Summary dated Nov. 9, 2021.
U.S. Appl. No. 17/191,632 Final Office Action dated Sep. 17, 2021.
U.S. Appl. No. 17/191,632 Office Action dated May 12, 2021.
U.S. Appl. No. 16/426,917 Notice of Allowance dated Oct. 1, 2019.
Wilson, et al. Single-Step Selection of Bivalent Aptamers Validated by Comparison with SELEX Using High-Throughput Sequencing. PLoS One. 2014; 9(6): e100572.
Zandian, Arash et al. Whole-Proteome Peptide Microarrays for Profiling Autoantibody Repertoires within Multiple Sclerosis and Narcolepsy. Journal of proteome research 16(3) 2017: 1300-1314. doi:10.1021/acs.jproteome.6b00916.
Beck, et al., "Trends in Glycosylation, Glycoanalysis and Glycoengineering of Therapeutic Antibodies and Fc-Fusion Proteins," Current Pharmaceutical Biotechnology, 2008, vol. 9, pp. 482-501.
Gopinath, et al., "Optimized Assembly and Covalent Coupling of Single-Molecule DNA Origami Nanoarrays," ACS Nano, 2014, vol. 8, No. 12, pp. 12030-12040.
Guan, et al., "Generation of acetyllysine antibodies and affinity enrichment of acetylated peptides," Nature Protocols, 2010, vol. 5, No. 9, pp. 1583-1595.
Guo, et al., "Immunoaffinity Enrichment and Mass Spectrometry Analysis of Protein Methylation," Molecular & Cellular Proteomics, 2014, vol. 13, No. 1, pp. 372-387.
Hattori, et al., "Next-generation antibodies for post-translational modifications," Current Opinion in Structural Biology, Aug. 2018, vol. 51, pp. 141-148.
Kaufmann, et al., "Use of antibodies for detection of phosphorylated proteins separated by two-dimensional gel electrophoresis," Proteomics, 2001, vol. 1, pp. 194-199.
Kershner, et al., "Placement and orientation of individual DNA shapes on lithographically patterned surfaces," Nature Nanotechnology, Sep. 2009, vol. 4, pp. 557-561.
Mimnaugh, et al.,"The measurement of ubiquitin and ubiquitinated proteins," Electrophoresis, 1999, vol. 20, pp. 418-428.
Office Action in CA3135206, mailed on Oct. 17, 2024, 4 pages.
Goldman et al., "Avidin: A Natural Bridge for Quantum Dot—Antibody Conjugates," Journal of the American Chemical Society, 2002, vol. 124, pp. 6378-6382.
Goldman et al., "Multiplexed Toxin Analysis Using Four Colors of Quantum Dot Fluororeagents," Analytical Chemistry, 2004, vol. 76, pp. 684-688.
Hoff et al., "Nanoscale Protein Patterning by Imprint Lithography," Nano Letters, 2004, vol. 4, No. 5, pp. 853-857.
Kuzuya et al., "Precisely Programmed and Robust 2D Streptavidin Nanoarrays by Using Periodical Nanometer—Scale Wells Embedded in DNA Origami Assembly," ChemBioChem, 2009, vol. 10, pp. 1811-1815.
Liang et al., "An oligonucleotide microarray for microRNA expression analysis based on labeling RNA with quantum dot and nanogold probe," Nucleic Acids Research, 2005, vol. 33, No. 2, 8 pages.
Niemeyer et al., "Supramolecular Nanocircles Consisting of Streptavidin and DNA," Angewandte Chemie International Edition, 2000, vol. 39, No. 17, pp. 3056-3059.
Olsnes, S., "The history of ricin, abrin and related toxins," Toxicon, 2004, pp. 361-370.
Pires et al., "A rapid magnetic particle-based enzyme immunoassay for human cytomegalovirus glycoprotein B quantification," Journal of Pharmaceutical and Biomedical Analysis, 2018, vol. 156, pp. 372-378.
Purschke et al., "A DNA Spiegelmer to staphylococcal enterotoxin B," Nucleic Acids Research, 2003, vol. 31, No. 12, pp. 3027-3032.
Slaughter et al., "Detection of enzyme polymorphism by using monoclonal antibodies," Proceedings of the National Academy of Sciences, Feb. 1981, vol. 78, No. 2, pp. 1124-1128.
Tesh et al., "The pathogenic mechanisms of Shiga toxin and the Shiga-like toxins," Molecular Microbiology, 1991, vol. 5, No. 8, pp. 1817-1822.
Wang et al., "Antibody Structure, Instability, and Formulation," Journal of Pharmaceutical Sciences, Jan. 2007, vol. 96, No. 1, pp. 1-26.
Zhang et al., "The Three-dimensional Crystal Structure of Cholera Toxin," Journal of Molecular Biology, 1995, vol. 251, pp. 563-573.

\* cited by examiner

METHODS AND SYSTEMS FOR INTEGRATED ON-CHIP SINGLE-MOLECULE DETECTION

CROSS-REFERENCE

This application is a continuation application of International Patent application No. PCT/US2020/030501, filed Apr. 29, 2020, which claims the benefit of U.S. Provisional Application No. 62/840,209, filed Apr. 29, 2019, each of which is incorporated herein by reference in its entirety.

BACKGROUND OF THE INVENTION

Biological assays may be used for applications such as genome sequencing or protein expression. It may be beneficial to tailor the design of biological assays for the fast, high-confidence identification of a large number of small amounts of different biological materials. However, such requirements may introduce challenges in the form of competing constraints on the design and fabrication of chips, flow cells, and detection systems used for such assays. For example, the large number of objects to be detected may impose constraints on the amount of material that can be used for each object and on the density at which these objects can be loaded on a substrate of reasonable size. These limitations in turn may imply that only limited amount of signal is available for detection and that the signal of neighboring objects becomes difficult to differentiate. Further, the limited signal amount emitted by each object can negatively impact a detection time needed to detect the objects.

SUMMARY OF THE INVENTION

The present disclosure provides methods and systems for performing single-molecule detection using fabricated integrated on-chip devices. Using disclosed methods and systems, single-molecule detection can be performed while achieving advantages such as: a reduction in the scanning time required by using a large number of light sensors for parallel imaging without moving parts during imaging, a reduction in noise levels by reducing the number of components in the imaging system, an improved resolution arising from detecting one object on each sensor, decreased crosstalk between neighboring object signals, and improved detection sensitivity arising from improved light collection enabled by microscale or nanoscale features on the imaging sensors.

In an aspect, the present disclosure provides a method for on-chip detection of an array of biological, chemical, or physical entities, comprising: (a) providing an array of light sensing devices; (b) immobilizing the array of biological, chemical, or physical entities on a substrate of the array of light sensing devices; (c) exposing the array of biological, chemical, or physical entities to electromagnetic radiation sufficient to excite the array of biological, chemical, or physical entities, thereby producing an emission signal of the array of biological, chemical, or physical entities; (d) using the array of light sensing devices, acquiring pixel information of the emission signal of the array of biological, chemical, or physical entities without scanning the array of light sensing devices across the array of biological, chemical, or physical entities; and (e) detecting the array of biological, chemical, or physical entities based at least in part on the acquired pixel information.

In some embodiments, the electromagnetic radiation sufficient to excite the array of biological, chemical, or physical entities comprises one or more wavelengths of light. In some embodiments, the array of biological, chemical, or physical entities comprises biological, chemical, or physical entities selected from the group consisting of: (i) a single structured nucleic acid particle (SNAP); (ii) a single SNAP with at least one fluorescent label; (iii) a DNA origami; (iv) a DNA origami with at least one fluorescent label; (v) a single protein (antibody, antigen, peptide, aptamer, or other proteins); (vi) a single protein (antibody, antigen, peptide, aptamer, or other proteins) bound to a single SNAP; (vii) a single protein (antibody, antigen, peptide, aptamer, or other proteins) bound to a single DNA origami, one or more fluorescent probes bound to a biological, chemical, or physical entity of (i)-(vii); (ix) one or more nanoparticles (e.g., organic, inorganic, or biological); (x) one or more nanoparticles with optical properties (e.g., quantum dots); (xi) one or more formulations of dendrimers; and (xii) a combination thereof.

In some embodiments, the array of light sensing devices comprises one or more device features selected from the group consisting of: (i) a surface coating to promote adhesion of specific biological, chemical, or physical entities (e.g., $ZrO_2$, silane, or thiols); (ii) a surface coating to prevent nonspecific binding of specific biological, chemical, or physical entities (e.g., phosphate, phosphonate, PEG-silane, or PEG-thiols); (iii) a differential surface coating to promote binding of a first type of biological, chemical, or physical entities in some locations and to prevent non-specific binding in other locations; (iv) a single-layer surface coating; (v) a multiple-layer surface coating; (vi) a surface coating deposited by atomic layer deposition (ALD), molecular layer deposition (MLD), chemical layer deposition (CVD), physical layer deposition (PLD) (e.g., evaporation), spin coating, dipping, or a combination thereof; (vii) a surface coating patterned by lithography and/or etching processes; (viii) a surface coating with one or more optical properties (e.g., bandpass filters, polarization filters, anti-reflection, fluorescent, or reflective coatings); (ix) a compartment of each pixel with nanowell-like structures to prevent crosstalk (e.g., opaque walls); (x) a compartment of each pixel with nanowell-like structures to increase fluorescent light collection (e.g., photo-sensitive walls); and (xi) a combination thereof.

In some embodiments, the array of light sensing devices comprises one or more flow cells (e.g., fabricated directly on top of the array of light sensing pixels).

In some embodiments, the array of light sensing devices comprises one or more instruments selected from the group consisting of: (i) an instrument configured for detection of an array of immobilized biological, chemical, or physical entity without scanning a detector of the instrument; (ii) an instrument configured for detection of an array of immobilized biological, chemical, or physical entity without any lens of a detector of the instrument; (iii) an instrument configured for detection of an array of immobilized biological, chemical, or physical entity without a focusing mechanism of a detector of the instrument; (iv) an instrument configured for parallel excitation of immobilized fluorescent markers (e.g., configured to use four-beam interference to create a two-dimensional sine wave pattern); and (v) a combination thereof.

In some embodiments, the array of light sensing devices is made of material compatible with complementary metal-oxide semiconductor (CMOS) processing, and wherein the array of light sensing devices is configured to be functionalized.

In some embodiments, the array of light sensing devices is fabricated using one or more process steps selected from the group consisting of: (i) differential functionalization of an active surface of the array of light sensing devices; (ii) integration of nanowells to prevent cross-talk; (iii) integration of nanowells to increase light collection; (iv) assembly of flow cell directly on array of light sensing devices; and (v) a combination thereof.

In some embodiments, a dimension and/or pitch of individual pixels of the array of light sensing devices is matched to a dimension and/or pitch of the array of biological, chemical, or physical entities.

In some embodiments, the array of light sensing devices comprises a coating comprising materials selected from the group consisting of: a metal (e.g., gold); a metal oxide (e.g., $ZrO_2$); and a metal nitride (e.g., TiN).

In some embodiments, the array of light sensing devices comprises a surface chemistry selected from the group consisting of: silanes (e.g., APTES); phosphates; phosphonates (e.g., (Aminomethyl)phosphonic acid or free phosphate); and thiols (e.g., Thiol-PEG-Amine or mPEG-Thiol).

In some embodiments, individual pixels of the array of light sensing devices are surrounded by a microwell or nanowell or other barrier between adjacent pixels to prevent crosstalk between pixels and/or to increase light collection. In some embodiments, the microwell or nanowell comprises walls that are opaque to light at an emission wavelength of the array of biological, chemical, or physical entities (e.g., a metal, such as Al or Ti). In some embodiments, the microwell or nanowell comprises walls made of one or more layers of material to convert photons to electrons (e.g., a silicon p-n junction); and/or one or more layers of material to collect generated electrons (e.g., a metal, such as Al or Ti).

In another aspect, the present disclosure provides a device for on-chip detection of an array of biological, chemical, or physical entities, comprising (a) an array of light sensing devices; and (b) an array of biological, chemical, or physical entities, wherein the array of biological, chemical, or physical entities is immobilized on a substrate of the array of light sensing devices; wherein the array of light sensing devices is configured to acquire pixel information of the array of biological, chemical, or physical entities without scanning the array of light sensing devices across the array of biological, chemical, or physical entities.

In some embodiments, the array of biological, chemical, or physical entities comprises biological, chemical, or physical entities selected from the group consisting of: (i) a single structured nucleic acid particle (SNAP); (ii) a single SNAP with at least one fluorescent label; (iii) a DNA origami; (iv) a DNA origami with at least one fluorescent label; (v) a single protein (antibody, antigen, peptide, aptamer, or other proteins); (vi) a single protein (antibody, antigen, peptide, aptamer, or other proteins) bound to a single SNAP; (vii) a single protein (antibody, antigen, peptide, aptamer, or other proteins) bound to a single DNA origami, one or more fluorescent probes bound to a biological, chemical, or physical entity of (i)-(vii); (ix) one or more nanoparticles (e.g., organic, inorganic, or biological); (x) one or more nanoparticles with optical properties (e.g., quantum dots); (xi) one or more formulations of dendrimers; and (xii) a combination thereof.

In some embodiments, the array of light sensing devices comprises one or more device features selected from the group consisting of: (i) a surface coating to promote adhesion of specific biological, chemical, or physical entities (e.g., $ZrO_2$, silane, or thiols); (ii) a surface coating to prevent nonspecific binding of specific biological, chemical, or physical entities (e.g., phosphate, phosphonate, PEG-silane, or PEG-thiols); (iii) a differential surface coating to promote binding of a first type of biological, chemical, or physical entities in some locations and to prevent non-specific binding in other locations; (iv) a single-layer surface coating; (v) a multiple-layer surface coating; (vi) a surface coating deposited by atomic layer deposition (ALD), molecular layer deposition (MLD), chemical layer deposition (CVD), physical layer deposition (PLD) (e.g., evaporation), spin coating, dipping, or a combination thereof; (vii) a surface coating patterned by lithography and/or etching processes; (viii) a surface coating with one or more optical properties (e.g., bandpass filters, polarization filters, anti-reflection, fluorescent, or reflective coatings); (ix) a compartment of each pixel with nanowell-like structures to prevent cross-talk (e.g., opaque walls); (x) a compartment of each pixel with nanowell-like structures to increase fluorescent light collection (e.g., photo-sensitive walls); and (xi) a combination thereof.

In some embodiments, the array of light sensing devices comprises one or more flow cells (e.g., fabricated directly on top of the array of light sensing pixels, or assembled/prepared postfabrication).

In some embodiments, the array of light sensing devices comprises one or more instruments selected from the group consisting of: (i) an instrument configured for detection of an array of immobilized biological, chemical, or physical entity without scanning a detector of the instrument; (ii) an instrument configured for detection of an array of immobilized biological, chemical, or physical entity without any lens of a detector of the instrument; (iii) an instrument configured for detection of an array of immobilized biological, chemical, or physical entity without a focusing mechanism of a detector of the instrument; (iv) an instrument configured for parallel excitation of immobilized fluorescent markers (e.g., configured to use four-beam interference to create a two-dimensional sine wave pattern); and (v) a combination thereof.

In some embodiments, the array of light sensing devices is made of material compatible with complementary metal-oxide semiconductor (CMOS) processing, and wherein the array of light sensing devices is configured to be functionalized.

In some embodiments, the array of light sensing devices is fabricated using one or more process steps selected from the group consisting of: (i) differential functionalization of an active surface of the array of light sensing devices; (ii) integration of nanowells to prevent cross-talk; (iii) integration of nanowells to increase light collection; (iv) assembly of flow cell directly on array of light sensing devices; and (v) a combination thereof.

In some embodiments, a dimension and/or pitch of individual pixels of the array of light sensing devices is matched to a dimension and/or pitch of the array of biological, chemical, or physical entities.

In some embodiments, the array of light sensing devices comprises a coating comprising materials selected from the group consisting of: a metal (e.g., gold); a metal oxide (e.g., $ZrO_2$); and a metal nitride (e.g., TiN).

In some embodiments, the array of light sensing devices comprises a surface chemistry selected from the group consisting of: silanes (e.g., APTES); phosphates; phosphonates (e.g., (Aminomethyl)phosphonic acid or free phosphate); and thiols (e.g., Thiol-PEG-Amine or mPEG-Thiol).

In some embodiments, individual pixels of the array of light sensing devices are surrounded by a microwell or nanowell to prevent crosstalk between pixels and/or to increase light collection. In some embodiments, the microwell or nanowell comprises walls that are opaque to light at an emission wavelength of the array of biological, chemical, or physical entities (e.g., a metal, such as Al or Ti). In some embodiments, the microwell or nanowell comprises walls made of one or more layers of material to convert photons to electrons (e.g., a silicon p-n junction); and/or one or more layers of material to collect generated electrons (e.g., a metal, such as Al or Ti).

In some embodiments, the present disclosure provides a system comprising: (a) a device of the present disclosure; and (b) a non-transitory computer-readable storage medium comprising machine-executable code that, upon execution by one or more computer processors, implements a method for on-chip detection of an array of biological, chemical, or physical entities, the method comprising: (i) using the array of light sensing devices, acquiring pixel information of the array of biological, chemical, or physical entities without scanning the array of light sensing devices across the array of biological, chemical, or physical entities; and (ii) detecting the array of biological, chemical, or physical entities based at least in part on the acquired pixel information.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
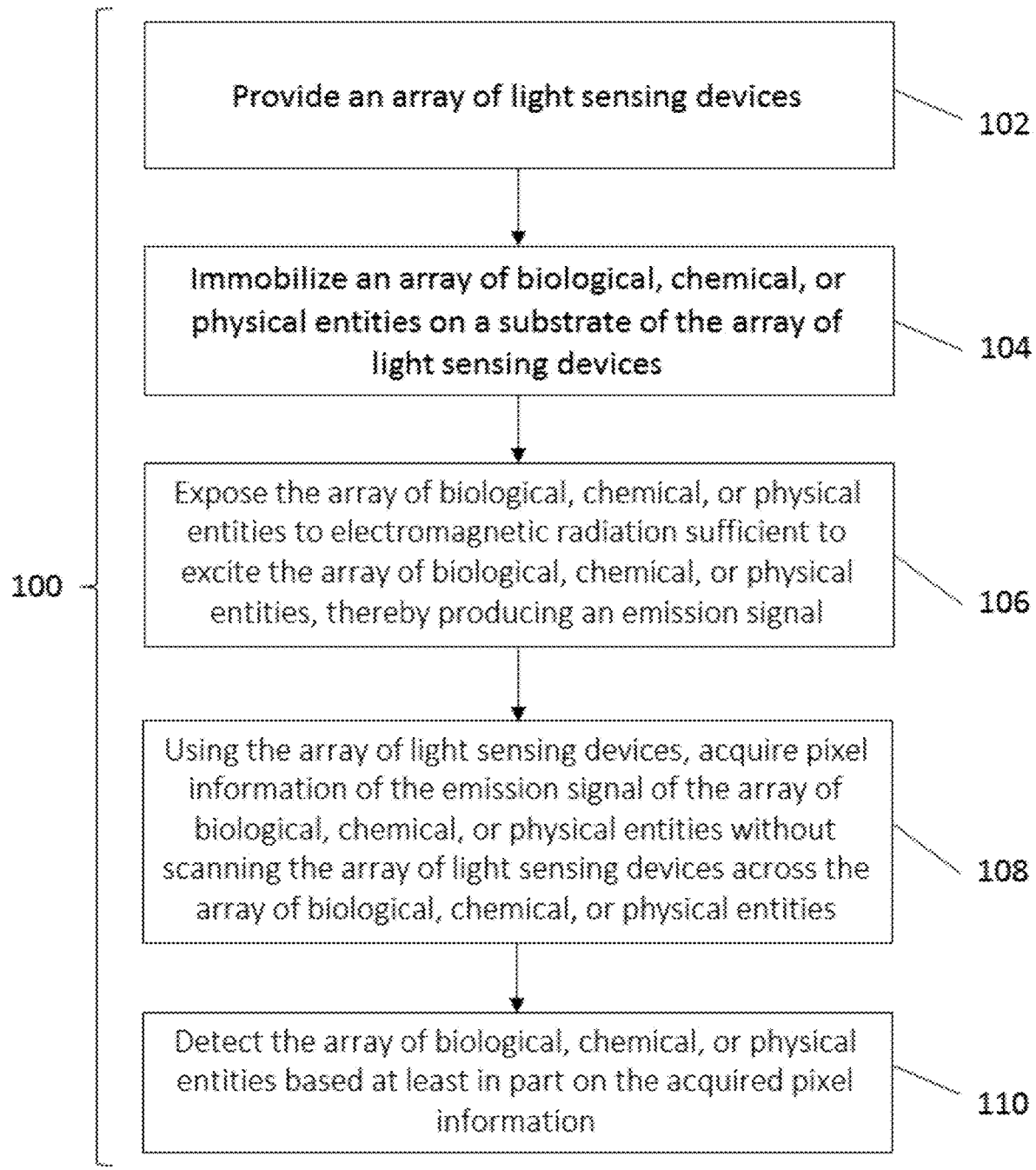
FIG. 1 illustrates an example workflow of a method for performing single-molecule detection using fabricated integrated on-chip devices, in accordance with disclosed embodiments.

Biological assays may be used for applications such as genome sequencing or protein expression. It may be beneficial to tailor the design of biological assays for the fast, high-confidence identification of a large number of small amounts of different biological materials. However, such requirements may introduce challenges in the form of competing constraints on the design and fabrication of chips, flow cells, and detection systems used for such assays. For example, the large number of objects to be detected may impose constraints on the amount of material that can be used for each object and on the density at which these objects can be loaded on a substrate of reasonable size. These limitations in turn may imply that only limited amount of signal may be available for detection and that the signal of neighboring objects becomes difficult to differentiate. Further, the limited signal amount emitted by each object can negatively impact a detection time needed to detect the objects.

Thanks to its many advantages (variety of probes, simple binding mechanism, optical detection), fluorescent labeling became the method of choice for many bio-assays. Often, the particles or molecules to be detected are immobilized on a flat substrate and detection may be performed with a fluorescent microscope. However, this approach may be limited by the microscope resolution, the intensity of the fluorescent signal emitted by the label, the cross talk between the signals of neighboring objects, the noise level and the time needed to scan large arrays of immobilized objects.

The present disclosure provides methods and systems for performing single-molecule detection using fabricated integrated on-chip devices. Using disclosed methods and systems, single-molecule detection can be performed while achieving advantages such as: a reduction in the scanning time required by using a large number of light sensors for parallel imaging without moving parts during imaging, a reduction in noise levels by reducing the number of components in the imaging system, an improved resolution arising from detecting one object on each sensor, decreased crosstalk between neighboring object signals, and improved detection sensitivity arising from improved light collection enabled by microscale or nanoscale features on the imaging sensors.

In assays with fluorescent detection, one or more objects (often very large arrays of them) may be immobilized on a surface, and this surface may be scanned with a microscope to detect any fluorescent signal from the immobilized objects. The microscope itself may comprise a digital camera configured to record, store, and analyze the data collected during the scan. These cameras may comprise an array of light sensing devices, such as charge coupled device (CCD) sensors, complementary metal-oxide-semiconductor (CMOS) sensors, charge injection device (CID) sensors, or JOT image sensors (Quanta).

Using systems and methods of the present disclosure, the objects to be imaged may be immobilized directly on the surface of the array of light sensing devices. Since such devices may be made out of CMOS-compatible materials, their imaging side can be differentially functionalized, and biological, chemical, or physical entities can then be bound to specific locations. In some embodiments, one biological, chemical, or physical entity to be detected is bound on each light sensing device (pixel) of such an array.

Using systems and methods of the present disclosure, the light path between the object to be imaged and the light sensing device can be advantageously reduced, thereby reducing the noise and distortions created along this light path by optical or flow cell components.

Using systems and methods of the present disclosure, each pixel of the light sensing array can be advantageously used to image one object. In comparison, for example, due to resolution limits, a camera used in a microscope may be expected to use at least four pixels per object. In some embodiments, each pixel may have a size of, for example, about 100 nm, about 200 nm, about 300 nm, about 400 nm, about 500 nm, about 600 nm, about 700 nm, about 800 nm, about 900 nm, about 1 µm, about 1.2 µm, about 1.5 µm, about 1.7 µm, about 2 µm, about 2.5 µm, about 3 µm, about 3.5 µm, about 4 µm, about 4.5 µm, about 5 µm, about 6.5 µm, about 7.4 µm, about 8 µm, about 9 µm, about 10 µm, or about 11 µm. The light sensing array may have a size of about 100 kilopixels, about 200 kilopixels, about 300 kilopixels, about 400 kilopixels, about 500 kilopixels, about 600 kilopixels, about 700 kilopixels, about 800 kilopixels, about 900 kilopixels, about 1 megapixels, about 1.2 megapixels, about 1.4 megapixels, about 1.6 megapixels, about 1.8 megapixels, about 2 megapixels, about 2.5 megapixels, about 3 megapixels, about 3.5 megapixels, about 4 megapixels, about 5 megapixels, about 6 megapixels, about 8 megapixels, about 10 megapixels, about 15 megapixels, about 20 megapixels, about 30 megapixels, about 50 megapixels, about 100 megapixels, about 200 megapixels, about 500 megapixels, about 1 gigapixel, about 2 gigapixels, about 5 gigapixels, or about 10 gigapixels.

Using systems and methods of the present disclosure, the substrate on which the biological, chemical, or physical entities are immobilized may not need to be scanned, thereby saving time, operation costs, and wear on the expensive parts of the instrument.

Referring to FIG. 1, in an aspect, the present disclosure provides a method 100 for on-chip detection of an array of biological, chemical, or physical entities, comprising: providing an array of light sensing devices (as in step 102); immobilizing the array of biological, chemical, or physical entities on a substrate of the array of light sensing devices (as in step 104); exposing the array of biological, chemical, or physical entities to electromagnetic radiation sufficient to excite the array of biological, chemical, or physical entities, thereby producing an emission signal of the array of biological, chemical, or physical entities (as in step 106); using the array of light sensing devices, acquiring pixel information of the emission signal of the array of biological, chemical, or physical entities without scanning the array of light sensing devices across the array of biological, chemical, or physical entities (as in step 108); and (d) detecting the array of biological, chemical, or physical entities based at least in part on the acquired pixel information (as in step 110).

Methods and systems of the present disclosure may comprise or be configured to allow immobilization of one or more biological, chemical, or physical entities on at least one pixel of a light sensor array. For example, biological, chemical, or physical entities may be selected from: (i) a single structured nucleic acid particle (SNAP); (ii) a single SNAP with at least one fluorescent label; (iii) a DNA origami; (iv) a DNA origami with at least one fluorescent label; (v) a single protein (antibody, antigen, peptide, aptamer, or other proteins); (vi) a single protein (antibody, antigen, peptide, aptamer, or other proteins) bound to a single SNAP; (vii) a single protein (antibody, antigen, peptide, aptamer, or other proteins) bound to a single DNA origami, one or more fluorescent probes bound to a biological, chemical, or physical entity of (i)-(vii); (ix) one or more nanoparticles (e.g., organic, inorganic, or biological); (x) one or more nanoparticles with optical properties (e.g., quantum dots); (xi) one or more formulations of dendrimers; and (xii) a combination thereof.

Methods and systems of the present disclosure may comprise one or more device features. For example, the one or more device features may be selected from: (i) a surface coating (e.g. $ZrO_2$, silane, or thiols) to promote adhesion of specific biological, chemical, or physical entities; (ii) a surface coating (e.g. phosphate or phosphonate, PEG-silane, or PEG-thiols) to prevent nonspecific binding of specific biological, chemical, or physical entities; (iii) a differential surface coating to promote binding of a first type of biological, chemical, or physical entities in some locations and to prevent non-specific binding in other locations; (iv) a single-layer surface coating; (v) a multiple-layer surface coating; (vi) a surface coating deposited by atomic layer deposition (ALD), molecular layer deposition (MLD), chemical layer deposition (CVD), physical layer deposition (PLD) (e.g., evaporation), spin coating, dipping, or a combination thereof; (vii) a surface coating patterned by lithography and/or etching processes; (viii) a surface coating with one or more optical properties (e.g., bandpass filters, polarization filters, anti-reflection, fluorescent, reflective coatings); (ix) a compartment of each pixel with nanowell-like structures to prevent cross-talk (nanowells with opaque walls) and/or increase fluorescent light collection (nanowells with photo-sensitive walls); and (x) a combination thereof.

Methods and systems of the present disclosure may comprise one or more flow cells. For example, the one or more flow cells may comprise a flow cell fabricated directly on top of an array of light sensing pixels.

Methods and systems of the present disclosure may comprise one or more instruments. For example, the one or more instruments may be selected from: (i) an instrument configured for detection of an array of immobilized biological, chemical, or physical entity without scanning a detector of the instrument; (ii) an instrument configured for detection of an array of immobilized biological, chemical, or physical entity without any lens of a detector of the instrument; (iii) an instrument configured for detection of an array of immobilized biological, chemical, or physical entity without a focusing mechanism of a detector of the instrument; (iv) an instrument configured for parallel excitation of immobilized fluorescent markers (e.g., configured to use four-beam interference to create a two-dimensional sine wave pattern); and (v) a combination thereof.

As an example, methods and systems of the present disclosure may comprise immobilization of SNAPs on 300-nm functionalized spots with a 1.625-μm pitch. The dimensions of the functionalized spots and/or the pitch may be chosen, for example, to be close to the dimensions of suitable image sensing arrays (e.g., commercially available image sensing arrays). In some embodiments, surfaces of sensing arrays are able to be functionalized because they are made of material compatible with complementary metal-oxide semiconductor (CMOS) processing.

Methods and systems of the present disclosure may comprise one or more process steps. For example, the one or more process steps may be selected from: (i) differential functionalization of an active surface of the array of light sensing devices; (ii) integration of nanowells to prevent cross-talk; (iii) integration of nanowells to increase light collection; (iv) assembly of flow cell directly on array of light sensing devices; and (v) a combination thereof.

The dimensions of each individual pixel of the light sensing device, which may be a commercially available device, may match the dimensions of the arrays (e.g., SNAP arrays) on the chips quite well. For example, a typical pixel may have an area of 1.4 μm×1.4 μm (e.g., 14 megapixels corresponds to 6.6×4.6 mm$^2$). In comparison, the immobilization spots may be about 0.3 μm in diameter with a pitch of 1.625 μm. The density of the arrays can be increased, for example, by reducing the pitch to 0.975 μm or even 0.650 μm, but the size of the pixel on commercially available light sensing devices may also expect to be reduced in the future. In principle, this design may be extended to much larger sensor arrays, including those with hundreds or even thousands of megapixels (e.g., 100 megapixels to 1 gigapixels such as the Canon 120MXS CMOS sensor).

The light sensing devices may acquire image or pixel information at an imaging rate of, for example, about 0.1, about 0.5, about 1, about 2, about 3, about 4, about 5, about 10, about 20, about 30, about 40, about 50, about 60, 70, 80, 90, about 100, about 200, about 300, about 400, about 500, about 600, about 700, about 800, about 900, about 1000, about 1100, about 1200, about 1300, about 1400, about 1500, about 1600, about 1700, about 1800, about 1900, about 2000, about 2500, about 5000, about 7500, about 10000, or about 20000 frames per second frames per second (fps). The light sensing devices may perform signal amplification, such as by using one or two amplifiers for each pixel. The signal amplification may be performed by components of the light sensing devices without using a separate amplification circuit, or by using a separate amplification circuit, or by a combination thereof. The array of light sensing devices may comprise for example, sCMOS sensors having one or two readout circuits per column of pixels.

A typical coating used on the immobilization spots, or between them, may include one or more dielectrics, one or more plastics, one or more types of glass, one or more nitrides, one or more metals (e.g., gold), one or more metal oxidex (e.g. $ZrO_2$), and/or one or more metal nitrides (TiN) in layer thicknesses varying from a few angstroms to several nanometers. A total number of coating layers of 1, 2, 3, 4, 5, 6, 7, 8, 9, 10, about 12, about 14, about 16, about 18, about 20, about 25, about 30, about 40, about 50, about 60, about 70, about 80, about 90, or about 100 coating layers may be used.

Typical surface chemistries used on the immobilization spots, or between them, may include silanes (e.g., (3-Aminopropyl)triethoxysilane, APTES), phosphates or phosphonates (e.g., (Aminomethyl)phosphonic acid, free phosphate) and thiols (e.g., Thiol-PEG-Amine, mPEG-Thiol), in thicknesses ranging from a few angstroms to a few nanometers. In some cases, a surface may be coated in a metal or metal oxide (e.g., gold, hafnium, aluminum, $Al_2O_3$, $ZrO_2$, $TiO_2$). Surface ligands or functional groups may be applied to surfaces as appropriate based upon the surface material (e.g., silanes for silica or glass, phosphates or phosphonates for $ZrO_2$).

Surfaces, including all areas in physical contact with a fluid may comprise a functionality, mask, adsorbent, texture, microstructure, capture agent, catalyst, deposit, coating, or other surface alteration. The application of a functionality, mask, adsorbent, texture, microstructure, capture agent, catalyst, deposit, coating, or other surface alteration may include altering hydrophobicity, altering hydrophilicity, altering amphipathicity, altering surface tension or surface energy, altering the physical, chemical, electrical, mechanical, or optical characteristics of the fluidic channel, affecting fluid flow or altering fluid properties, increasing or decreasing heat transfer or mass transfer, capturing or adsorbing species from a fluid, preventing adhesion of species from a fluid, performing chemical reactions, and other operations.

Figure 2:
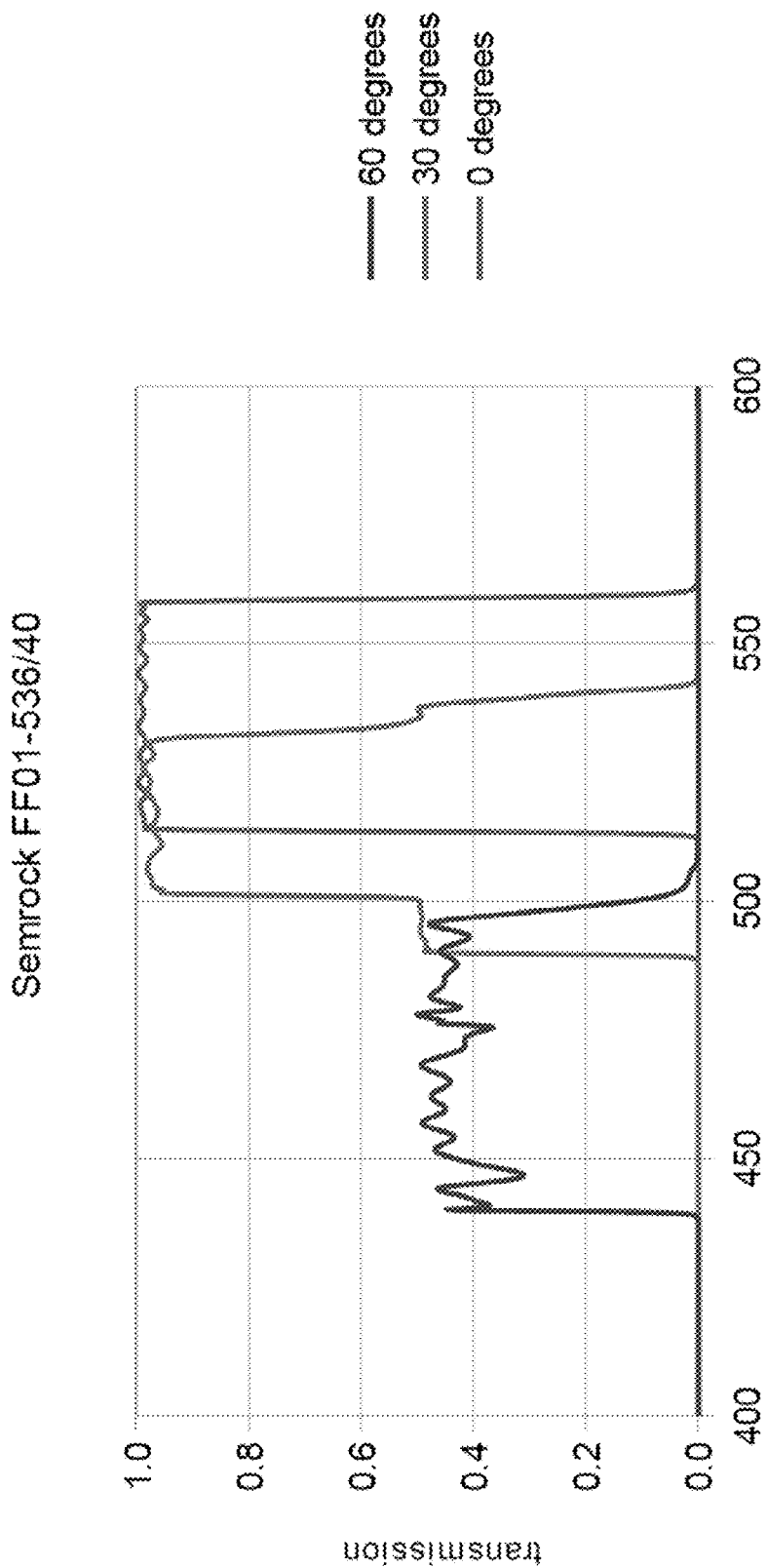
FIG. 2 illustrates a plot for transmission of a fluorescein or Alexa 488 emission filter vs. wavelength (nm) in a dry environment, in accordance with disclosed embodiments.

In some embodiments, each pixel may be surrounded by a microwell or nanowell to prevent crosstalk between pixels and/or to increase light collection. To prevent crosstalk, the wall(s) of these wells may comprise at least one layer opaque to light (e.g., in a wavelength range at which the biological, chemical, or physical entities to be detected are emitting); an example of such a layer may be a metal (e.g., Al or Ti). The layer opaque to light may comprise, for example, a dye. Since bandpass filter transmission may be a function of angle of incidence, at large angles of incidence, the bandpass filter may have low transmission at the dye's emission wavelengths, thereby reducing crosstalk between adjacent pixels. For example, FIG. 2 shows a plot for transmission of a fluorescein or Alexa 488 emission filter vs. wavelength (nm) in a dry environment, generated using Semrock's "MyLight" software. In water, the details may change, but the effect may be similar. The passing band for the filter may comprise a bandwidth of, for example, about 10 nm, about 20 nm, about 30 nm, about 40 nm, about 50 nm, about 60 nm, about 70 nm, about 80 nm, about 90 nm, about 100 nm, about 120 nm, or about 150 nm. In some embodiments, the filters comprise multi-band filters. The passing band for the filter may comprise a band center value of, for example, about 100 nm, about 120 nm, about 140 nm, about 160 nm, about 180 nm, about 200 nm, about 220 nm, about 240 nm, about 260 nm, about 280 nm, about 300 nm, about 320 nm, about 340 nm, about 360 nm, about 380 nm, about 400 nm, about 420 nm, about 440 nm, about 460 nm, about 480 nm, about 500 nm, about 520 nm, about 540 nm, about 560 nm, about 580 nm, about 600 nm, about 620 nm, about 640 nm, about 660 nm, about 680 nm, about 700 nm, about 720 nm, about 740 nm, about 760 nm, about 780 nm, about 800 nm, about 820 nm, about 840 nm, about 860 nm, about 880 nm, about 900 nm, about 920 nm, about 940 nm, about 960 nm, about 980 nm, or about 1,000 nm. The excitation light (e.g., electromagnetic radiation sufficient to excite the array of biological, chemical, or physical entities to produce an emission signal) may have an incidence angle of about 90 degrees, about 80 degrees, about 70 degrees, about 60 degrees, about 50 degrees, about 40 degrees, about 30 degrees, about 20 degrees, or about 10 degrees from a surface (e.g., sidewall) of the array of biological, chemical, or physical entities. To increase light collection, these microwell or nanowell walls may contain one or more layers of material to convert photon to electrons (e.g. a silicon p-n junction) and one or more layers of material to collect the generated electrons (e.g., a metal such as Al or Ti).

In some instances, it may be desirable to produce a microarray or nanoarray wherein a plurality of biological, chemical, or physical entities are spatially distributed over and stably associated with the surface of a solid support such that each individual biological, chemical, or physical entity may be spatially separated from each other biological, chemical, or physical entity.

In some embodiments this disclosure provides methods of producing an array of spatially separated biological, chemical, or physical entities, a method may comprise: obtaining a solid support with attachment sites, obtaining a sample comprising biological, chemical, or physical entities, obtaining seeds, each with a functional group, covalently attaching each biological, chemical, or physical entity to a single seed via the functional group, growing each attached seed to a SNAP (Structured Nucleic Acid Particles) of desired size, attaching the SNAPs to the attachment sites of the array, thereby producing a regular array of biological, chemical, or physical entities. In some instances, SNAPs can be any type of DNA based nanoparticle, such as rolling circle amplification-based nanoparticles, plasmids, or DNA origami nanoparticles.

For example, methods of producing an array of entities such as proteins may begin with the attachment of a protein to an oligonucleotide primer via a linker. The primer can be then annealed to a circular DNA template, and rolling circle amplification can be performed to produce a SNAP (indicated in this example as a DNA cluster). The SNAP can be then deposited onto a chip. In this example, the negative charge of the DNA backbone can interact with positively charged features of an array, such that the SNAP becomes immobilized on the array.

As another example, methods of producing an array of entities may begin with a primer having a linker initiating rolling circle amplification with a circular DNA template. The resulting SNAP (indicated in this example as a DNA cluster) thus comprises a linker, which can then be conjugated to a protein. The SNAP can be then deposited onto a chip. In this example, the negative charge of the DNA backbone can interact with positively charged features of an array, such that the SNAP becomes immobilized on the array.

As another example, methods of producing an array of entities may begin with a primer initiating rolling circle amplification with a circular DNA template. The resulting SNAP (indicated in this example as a DNA cluster) can then be joined with a crosslinker, which can then be conjugated with a protein, to result in a SNAP which may be crosslinked to a protein. The SNAP can be then deposited onto a chip. In this example, the negative charge of the DNA backbone can interact with positively charged features of an array, such that the SNAP becomes immobilized on the array.

SNAPs may be created, for example by rolling circle amplification or other acceptable method. These SNAPs can be then deposited onto a chip. For example, the negative charge of the DNA backbone can interact with positively charged features of an array, such that the SNAP becomes immobilized on the array. Separately, proteins can be modified with chemical handles which can bind a chemical moiety which can be on the SNAPs. The handled proteins can then be applied to the SNAPs, such that they covalently attach to the SNAPs.

In some embodiments this disclosure provides arrays of single molecules and methods and kits for producing arrays of single molecules. In some embodiments this disclosure provides arrays of biological, chemical, or physical entities and methods and kits for producing arrays of biological, chemical, or physical entities. In some examples, an array of biological, chemical, or physical entities may comprise an ordered series of biological, chemical, or physical entities arrayed on a solid support. In other examples, an array of biological, chemical, or physical entities may comprise an irregular array of biological, chemical, or physical entities.

In some examples, biological, chemical, or physical entities on an array may be separated by less than 10 nm, about 10 nm, 20 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 µm, 1.2 µm, 1.4 µm, 1.6 µm, 1.8 µm, 2 µm, 2.5 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 25 µm, 30 µm, 40 µm, 50 µm, 75 µm, 100 µm, 200 µm, 300 µm, 400 µm, 500 µm, or more than 500 µm. In some examples, biological, chemical, or physical entities on an array may be separated by at least about 10 nm, 20 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 µm, 1.2 µm, 1.4 µm, 1.6 µm, 1.8 µm, 2 µm, 2.5 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 25 µm, 30 µm, 40 µm, 50 µm, 75 µm, 100 µm, 200 µm, 300 µm, 400 µm, 500 µm, or more than about 500 µm. In some examples, biological, chemical, or physical entities on an array may be separated by no more than 500 µm, 400 µm, 300 µm, 200 µm, 100 µm, 75 µm, 50 µm, 40 µm, 30 µm, 25 µm, 20 µm, 19 µm, 18 µm, 17 µm, 16 µm, 15 µm, 14 µm, 13 µm, 12 µm, 11 µm, 10 µm, 9 µm, 8 µm, 7 µm, 6 µm, 5 µm, 4 µm, 3 µm, 2.5 µm, 2 µm, 1.8 µm, 1.6 µm, 1.4 µm, 1.2 µm, 1 µm, 950 nm, about 900 nm, 850 nm, 800 nm, 750 nm, 700 nm, 650 nm, 600 nm, 550 nm, 500 nm, 450 nm, 400 nm, 350 nm, 300 nm, 250 nm, 200 nm, 180 nm, 160 nm, 140 nm, 120 nm, 100 nm, 90 nm, 80 nm, 70 nm, 60 nm, 50 nm, 40 nm, 30 nm, 20 nm, 10 nm, or less than about 10 nm. In some cases, biological, chemical, or physical entities on the array may be separated by between about 50 nm and about 1 µm, about 50 nm and about 500 nm, about 100 nm and about 400 nm, about 200 nm and about 300 nm, about 500 nm and about 10 µm, about 50 nm and about 1 µm, or about 300 nm and about 1 µm. In some cases, the spacing of biological, chemical, or physical entities on the array may be determined by the presence of attachment sites arrayed on a solid support.

In some embodiments an array may be created on a solid support. The solid support may be any solid surface to which molecules can be covalently or non-covalently attached. Non-limiting examples of solid substrates include slides, surfaces of elements of devices, surface coatings of elements of devices, membranes, flow cells, wells, chambers, and macrofluidic chambers. Solid supports used herein may be flat or curved, or can have other shapes, and can be smooth or textured. In some cases, solid support surfaces may contain microwells. In some cases, substrate surfaces may contain nanowells. In some cases, solid support surfaces may contain one or more microwells in combination with one or more nanowells. In some embodiments, the solid support can be composed of glass, carbohydrates such as dextrans, plastics such as polystyrene or polypropylene, polyacrylamide, latex, silicon, metals such as gold, chromium, titanium, or tin, titanium oxide, tin oxide, or cellulose. In some examples, the solid support may be a slide or a flow cell.

A flow cell may be coupled to a solid support. In some embodiments, a flow cell joined to a solid support. In some embodiments, a solid support may be incorporated into a flow cell. In some embodiments, a solid support for binding a plurality of attached molecules may be directly fabricated on a substrate material (e.g., glass, silica, fused silica, quartz). A fabricated substrate may be formed into a flow cell by the enclosure of the solid support area with a cover piece. A flow cell may comprise a fluidic device with one or more ports that permit passage of fluids into and/or out of the flow cell device. The fluidic device may be configured to permit passage of one or more fluids across or through the solid support.

Flow cells of the present disclosure may be designed for fluid transfer and control at various length scales, including macrofluidic and microfluidic length scales. A flow cell may be a particular shape including square, rectangular, oval, or circular. A flow cell may be designed to be a fixed or removable piece of a larger fluid transfer system, with a shape, size, or footprint that may be customized to the needs of the larger fluid transfer system. A flow cell may have a particular length, width, or height depending upon the application of the fluid. A flow cell may have a length, width, or height of about 1 centimeter (cm), 10 cm, 15 cm, 20 cm, 30 cm, 40 cm, 50, or about 100 cm. A fluidic device may have a length, width, or height of at least about 1 cm, 10 cm, 15 cm, 20 cm, 30 cm, 40 cm, 50 cm, or about 100 cm or more. A flow cell may have a length, width, or height of no more than about 100 cm, 50 cm, 40 cm, 30 cm, 20 cm, 15 cm, 10 cm, or 1 cm or less.

In some embodiments, a solid support may be characterized by a thickness or depth. The thickness of a solid support may be uniform or may vary over the body of the solid support. The thickness of the solid support may be altered by a fabrication, forming or machining process. In some cases, a solid support may have a thickness of about 1 micrometer ($\mu m$), 10 $\mu m$, 50 $\mu m$, 100 $\mu m$, 250 $\mu m$, 500 $\mu m$, 750 $\mu m$, 1 millimeter (mm), 5 mm, 1 centimeter (cm), 10 cm or more. In some cases, a substrate may have a thickness of at least about 1 micrometer ($\mu m$), 10 $\mu m$, 50 $\mu m$, 100 $\mu m$, 250 $\mu m$, 500 $\mu m$, 750 $\mu m$, 1 millimeter (mm), 5 mm, 1 centimeter (cm), 10 cm or more. In some cases, a solid support may have a thickness of no more than about 10 cm, 1 cm, 5 mm, 1 mm, 750 $\mu m$, 500 $\mu m$, 250 $\mu m$, 100 $\mu m$, 50 $\mu m$, 10 $\mu m$, 1 $\mu m$ or less.

In some embodiments, surfaces of the solid support may be modified to allow or enhance covalent or non-covalent attachment of molecules such as the SNAPs described herein. The solid support and process for molecule attachment are preferably stable for repeated binding, washing, imaging and eluting steps. In some cases, surfaces may be modified to have a positive or negative charge. In some cases, surfaces may be functionalized by modification with specific functional groups, such as maleic or succinic moieties, or derivatized by modification with a chemically reactive group, such as amino, thiol, or acrylate groups, such as by silanization. Suitable silane reagents include aminopropyltrimethoxysilane, aminopropyltriethoxysilane and 4-aminobutyltriethoxysilane. The surfaces may be functionalized with N-Hydroxysuccinimide (NHS) functional groups. Glass surfaces can also be derivatized with other reactive groups, such as acrylate or epoxy, using, e.g., epoxysilane, acrylatesilane or acrylamidesilane.

In some embodiments, the solid support may be modified to reduce non-specific attachment of SNAPs to the solid support. In some embodiments, the solid support may be modified to reduce non-specific attachment of biological entities and/or chemical entities to the solid support. In some embodiments, the solid support may be passivated. In some further embodiments, the surface of the solid support may be passivated. In some embodiments, the passivation layer may include diamond-like carbon, hexa-methyldisilizane, Teflon, fluorocarbon, a polymer such as polyethylene glycol (PEG) and/or Parylene. In some embodiments, a solid support may be passivated by the attachment of Polyethylene glycol (PEG) molecules across the solid support. In some embodiments, a solid support may be passivated using salmon sperm DNA, glycols, albumin, or a combination of the above. In some embodiments, a solid support may be passivated using one or more components selected from the group consisting of salmon sperm DNA, glycols, and albumin. In some embodiments, a solid support may be passivated using a blocking reagent such as nitrocellulose or phosphates. In some embodiments, passivation components may be exposed to a surface. In some embodiments, passivation components may not be covalently bound to a surface. In some embodiments, passivation materials may be not covalently bound to the solid support. In some embodiments, passivating materials may reduce the instance of non-specific binding of undesired molecules to the solid support surface.

Using processes and systems of the present disclosure, surface functionalization and passivation may be performed, which may be advantageous because functionalizing and passivating molecules can be localized to specific surface areas based upon a surface material and chemistry. For example, silanated surface functionalizations can be bound to silica surfaces while phosphate passivating groups can be bound to metal oxide surfaces. Surface functionalizations and surface passivations may be bound to a surface covalently and may be less susceptible to degradation via hydrolysis or other mechanisms. This may lead to more stable and effective coatings in functional and passivated areas on a surface under a wider variety of conditions and over a longer period of time.

Further, the processes provided herein may create coatings of substantially uniform thickness and may be less susceptible to poorly-controlled layer growth. Inorganic, metal, or metal oxide surfaces may enable precision functional and passivated coatings using covalently bound functional groups such as silanes, phosphates, or phosphonates. A number of phosphate or phosphonate-containing molecules (e.g., $HPO_3^{2-}$, (aminomethyl)phosphonic acid, PEG-phosphonate) may be easily deposited from solution or vapor phase on metal or metal oxide (e.g., Au or $ZrO_2$) surfaces in a self-limited fashion (e.g., formation of self-assembled monolayers, SAMs). Metal or metal oxide/phosphate or phosphonate coatings may be limited to forming SAMs, so process uniformity may be easily controlled. Likewise, silane compounds (e.g., 3-aminopropyl) trimethoxysilane (APTMS), APTES, mercaptosilane) may be deposited from solution or vapor phase on a substrate such as silica or fused silica in a self-limited fashion.

Certain metals or metal oxides (e.g., Au or $ZrO_2$) may interact strongly with phosphates and phosphonates, so processes and systems of the present disclosure may also be used to prepare patterned areas of directly-immobilized biomolecules, such as DNA, RNA, phosphopeptides, and phosphoproteins, without the need for additional surface modifications after a metal or metal oxide coating may be prepared. Silicon and silica substrates may interact strongly with silanes so processes and systems of the present disclosure may also be used to prepare patterned areas of directly-immobilized biomolecules, such as DNA, RNA, phosphopeptides, and phosphoproteins, without the need for additional surface modifications after the substrate may be prepared.

Through patterning, silane processes (and other material-specific coating processes) may be compatible with metal or metal oxide-coated surfaces. For example, a Si or $SiO_2$ substrate can be coated with $ZrO_2$, which can be selectively etched to produce a surface with patterned areas of $SiO_2$ and $ZrO_2$. Silane chemistry may be used to selectively functionalize or passivate the $SiO_2$ regions, then phosphate or phosphonate chemistry may be used to functionalize or passivate the $ZrO_2$ regions, or vice versa. In some cases, a substrate surface may be completely functionalized or completely passivated. In other cases, specific areas of a fluidic surface may be functionalized and other areas may be passivated.

In some embodiments, processes and systems of the present disclosure may comprise passivation or functionalization for specific target molecules or particle immobilization. Different passivated or functionalized regions of metal or metal oxide (e.g., Au or $ZrO_2$) can be prepared with reagents such as phosphates, phosphonates, and their derivatives. For example, passivating or functionalizing using phosphate or phosphonate may include one or more of: direct immobilization of phosphate- or phosphonate-containing (bio)molecules (e.g., DNA); amine-terminated phosphates and phosphonates (e.g., (Aminomethyl)phosphonic acid [CAS:1066-51-9]); Aminoalkyl phosphates, phosphonates, or related molecules or compounds with varying alkyl chain length, such as (Aminoethyl)phosphonic acid and (Aminopropyl)phosphonic acid); Carboxy-terminated phosphates and phosphonates, including Carboxyalkyl phosphates, phosphonates, or related molecules or compounds, such as (Carboxymethyl)phosphonic acid [CAS:4408-78-0] and related carboxyalkylphosphonates with varying alkyl chain length; Phospholipids and alkyl-terminated phosphates and phosphonates, such as alkylphosphonic acids, or related molecules or compounds (e.g., octadecylphosphonic acid (ODPA) [CAS:4724-47-4] and related alkylphosphonates with varying alkyl chain length); and thiol-terminated phosphates and phosphonates, such as Thiophospate [CAS: 10489-48-2] or related molecules or compounds with varying chain lengths, side groups, and/or compositions.

Different passivated or functionalized regions of silicon, silica, or glass substrates (e.g., fused silica) can be prepared with reagents such as silanes, organosilanes, and their derivatives. For example, passivating or functionalizing using silanes or organosilanes may include one or more of: amine-terminated silanes (e.g., (3-aminopropyl)triethoxysilane [CAS:919-30-2]; (3-aminopropyl)trimethoxysilane [CAS: 13822-56-5]); amine-terminated silanes with secondary amines (e.g., N-(6-aminohexyl)aminomethyl triethoxysilane [15129-36-9]; N-(2-aminoethyl)-3-aminopropyl triethoxysilane [CAS 5089-72-5]; N-(2-aminoethyl)-3-aminopropyl triethoxysilane [CAS 1760-24-3]; halogenated or hydrogenated silanes (e.g., chloro-dimethylsilane [CAS: 1066-35-9]; 4-bromobutyl trimethoxysilane [CAS 226558-82-3]; 7-bromoheptyl trimethoxysilane; 5-bromopentyl trimethoxysilane [773893-02-0]; 3-bromopropyl trimethoxysilane [CAS 51826-90-5]; 11-bromoundecyl trimethoxysilane [CAS 17947-99-8]; 3-chloroisobutyl trimethoxysilane [17256-27-8]; 2-(chloromethyl)allyl trimethoxysilane [CAS 39197-94-9] or triethoxy silane [CAS: 2487-90-3]); silanes with alkyl sidechains or varying length (e.g., trimethoxypropylsilane [CAS: 1067-25-0]); thiol-terminated silanes (e.g., (3-mercaptopropyl)trimethoxysilane [CAS: 4420-74-0]); epoxidated silanes (e.g., 2-(3,4-epoxycyclohexyl)ethyl triethoxysilane [CAS 10217-34-2]; 2-(3,4-epoxycyclohexyl)ethyl trimethoxysilane [CAS 3388-04-3]; 5,6-epoxyhexyl triethoxysilane [CAS 86138-01-4]; (3-glycidoxypropyl) triethoxysilane [CAS 2602-34-8]; (3-glycidoxypropyl) trimethoxysilane [CAS: 2530-83-8]; 2-(3,4-epoxycyclohexyl)ethylmethyl diethoxysilane [CAS 14857-35-3]; (3-glycidoxypropyl)methyl diethoxysilane [CAS 2897-60-1]; (3-glycidoxypropyl)methyl dimethoxysilane [CAS 65799-47-5]; (3-glycidoxypropyl)dimethyl ethoxysilane [CAS 17963-04-1]; ester-functionalized silanes (e.g., acetoxymethyl triethoxysilane [CAS 5630-83-1]; acetoxymethyl trimethoxysilane [CAS 65625-39-0]; 2-[(acetoxy (polyethyleneoxy)propyl]triethoxysilane; 3-acetoxypropyl trimethoxysilane [CAS 59004-18-1]; benzoyloxypropyl trimethoxysilane [CAS 76241-02-6]; 10-(carbomethoxy) decyldimethyl methoxysilane [CAS 1211488-83-3]; 2-(carbomethoxy)ethyl trimethoxysilane; triethoxysilylpropoxy (polyethyleneoxy)dodecanoate [1041420-54-5]; and silanes with other reactive sidechains (e.g., triethoxy-vinylsilane [CAS: 78-08-0]), or related molecules or compounds with varying chain lengths, side groups, and/or compositions.

A surface functionalization may comprise organic chains containing reactive groups. The reactive groups may be located at a position within a chain, including at a terminal position (e.g., a terminal carboxylic acid group), within a chain (e.g., a secondary amine), or pendant to an atom within a chain (e.g., a non-terminal carboxylic acid group). In some cases, an organic chain may comprise more than one functional group (e.g., a primary amine and a secondary amine). In some cases, an organic chain may include more than one functional group to create more than one chemical property (e.g., two differing types of reactivity; chemical reactivity and hydrophobicity). In some cases, a surface functionalization may comprise more than one functional group to increase the likelihood of a chemical process occurring (e.g., primary and secondary amines to increase the likelihood of reaction with an amine group).

In some embodiments, processes and systems of the present disclosure may comprise passivating groups or blocking groups to prevent binding (e.g., to small molecules, peptides, proteins, nucleic acids, and nanoparticles). Passivating agents may include organic or inorganic coatings such as metals, metal oxides, and ionic compounds. Surface passivating agents may bond with or adsorb to active sites or defects on the surface of a fabricated substrate, thereby blocking adhesion of other molecules to active sites or defects. A surface passivating agent may be applied as a coating, a monolayer or may specifically react at sites that require passivating. A surface passivating agent may be applied via a liquid or gas phase reaction, or a liquid or gas phase deposition. A blocking group may include a group that prevents other molecules from binding to a surface by physically blocking or repelling other molecules from approaching a surface. Blocking molecules may include steric blockers such as branched polymers (e.g., PEG) or long-chain alkyls. Blocking molecules may include molecules that create repulsion by electrical or magnetic fields, such as ionic chains or polymers or magnetic nanoparticles.

Different passivated or blocked regions of a metal or metal oxide (e.g. Au or $ZrO_2$) can be prepared with reagents such as phosphates, phosphonates, and their derivatives. For example, passivating or blocking using phosphate or phosphonate may include one or more of: free phosphate or hydrogen phosphate, or dihydrogen phosphate; Phosphate-terminated PEG reagents (with various lengths and branching); Bis- or tris-phosphates or phosphonates (di- and tri-phosphonates) (e.g., molecules of varying compositions that have two or more terminal phosphates or phosphonate groups linked by a particular size or composition of alkyl, amide, ester, carboxylic acid, alcohol, carbonyl, or other chemical moieties), such as etidronic acid [CAS:25211-86-3] and Nitrilotri(methylphosphonic acid) [CAS:6419-19-8]. In some cases, a passivating or blocking group may be deposited in step-wise fashion on a metal or metal oxide surface by first depositing a compound such as a phosphate or phosphonate (e.g., an epoxy-terminated phosphate), then reacting the epoxy group with a reactive group on a blocking molecule (e.g. an amine-terminated PEG molecule). In other cases, a passivating agent or blocking group may be deposited in a single step.

Different passivated regions of a silicon, silica, or glass substrates (e.g., fused silica) can be prepared with reagents such as silanes, organosilanes, and their derivatives. For example, passivating using silanes or organosilanes may include one or more of: silane ($SiH_4$) or halogenated silanes (e.g., $SiCl_3H$); silane-terminated PEG reagents (with various lengths and branching); disilanes, trisilanes, or larger oligomerized silanes (e.g., 2 or more bonded silicon atoms with hydrogenated, halogenated, or alkyl side groups); or silanes with alkyl side groups (e.g., butylsilane). In some cases, a passivating or blocking group may be deposited in step-wise fashion on an inorganic substrate surface such as silicon, silica, or glass substrate, by first depositing a compound such as a silane or organosilane (e.g., an epoxy-terminated silane), then reacting an epoxy group with a reactive group on a blocking molecule (e.g. an amine-terminated PEG molecule). In other cases, a passivating agent or blocking group may be deposited in a single step.

In some embodiments, the solid support may be modified across the entire surface to which molecules are to be attached. In other embodiments, the solid support may contain regions which are modified to allow attachment of molecules and regions which are not modified, or regions which are modified to decrease attachment of molecules and regions which are not modified, or regions which are modified to increase attachment of molecules and regions which are modified to decrease attachment of molecules. In some cases, attachment sites may be created in an array, for example an ordered array.

An ordered array of attachment sites may be created by, for example, photolithography, Dip-Pen nanolithography, nanoimprint lithography, nanosphere lithography, cluster lithography, nanopillar arrays, nanowire lithography, scanning probe lithography, thermochemical lithography, thermal scanning probe lithography, local oxidation nanolithography, molecular self-assembly, stencil lithography, double-beam interference lithography, or electron-beam lithography. Attachment sites in an ordered array may be located such that each attachment site may be less than an average of 20 nanometers (nm), or about 20 nm, about 50 nm, about 75 nm, about 100 nm, about 125 nm, about 150 nm, about 175 nm, about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, about 700 nm, about 725 nm, about 750 nm, about 775 nm, about 800 nm, about 825 nm, about 850 nm, about 875 nm, about 900 nm, about 925 nm, about 950 nm, about 975 nm, about 1000 nm, about 1025 nm, about 1050 nm, about 1075 nm, about 1100 nm, about 1125 nm, about 1150 nm, about 1175 nm, about 1200 nm, about 1225 nm, about 1250 nm, about 1275 nm, about 1300 nm, about 1325 nm, about 1350 nm, about 1375 nm, about 1400 nm, about 1425 nm, about 1450 nm, about 1475 nm, about 1500 nm, about 1525 nm, about 1550 nm, about 1575 nm, about 1600 nm, about 1625 nm, about 1650 nm, about 1675 nm, about 1700 nm, about 1725 nm, about 1750 nm, about 1775 nm, about 1800 nm, about 1825 nm, about 1850 nm, about 1875 nm, about 1900 nm, about 1925 nm, about 1950 nm, about 1975 nm, about 2000 nm, or more than an average of 2000 nm from any other attachment site. In some cases, the solid support may comprise a random or non-ordered array of attachment sites. The spacing of an ordered or non-ordered array of attachment sites may be calculated as an average spacing between detected attachment sites as determined by a suitable methods, such as a method that permits direct detection of attachment sites (e.g., fluorescent microscopy or surface plasmon resonance) or an analytical method that permits indirect detection of attachment sites (e.g., spectroscopic quantitation of surface functional groups).

In some cases, the spacing of attachment sites on the solid support may be selected depending on the size of the SNAPs to be used. For example, the spacing of the attachment sites may be selected such that the distance between the edges of any two attachment sites may be greater than the diameter of the SNAP used.

In some cases, the size of the attachment sites on the solid support may be selected depending on the size of the SNAPs to be used. For example, the size of the attachment sites may be selected such that the diameter of each attachment sites may be less than the diameter of the SNAP used.

In some cases, the attachment sites may be provided in microwells or nanowells.

In some cases, functional groups may be present in a random spacing and may be provided at a concentration such that functional groups are on average at least about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm, or more than 100 nm from any other functional group.

All materials chosen for a solid support may be chosen to exhibit negligible levels of autofluorescence. Autofluorescence may be characterized at a particular wavelength or range of wavelengths. For example, autofluorescence may be characterized in the ultraviolet, visible, and/or infrared region of the electromagnetic spectrum. A material may be chosen if it has a negligible fluorescence in a range from about 1 nm to 100 nm, 1 nm to 400 nm, 100 nm to 700 nm, 400 nm to 700 nm, 400 nm to 1000 nm, 400 nm to 5000 nm, 700 nm to 1000 nm, 700 nm to 5000 nm, or from about 1 nm to about 5000 nm.

In some cases, the solid support may be optically opaque. In some cases, the solid support may be optically clear at one or more wavelengths. In some cases, the solid support may be partially, optically clear, or may be optically clear in some regions. For example, a solid support may be optically opaque in regions that are not functionalized, and optically clear in regions that are functionalized.

The solid support may be indirectly functionalized. For example, the solid support may be PEGylated and a functional group may be applied to all or a subset of the PEG molecules.

In some cases, the efficiency of attachment of the SNAPs to the solid support may be high. In some cases, the efficiency of attachment of the SNAPs to the solid support may be moderate. In some cases, the efficiency of attachment of the SNAPs to the solid support may be low. The efficiency of the attachment of the SNAPs to the solid support may be influenced by many factors, including, but not limited to: sequence of clusters, size of SNAPs relative to size of a corresponding binding patch (e.g., large clusters may not bind well to very small patches), the extent to which SNAPs have had their structure modified in such a way so as to influence their binding, age of SNAPs, storage conditions of a buffer or buffers that come into contact with SNAPs, storage conditions of SNAPs, pH or other properties of solvent in which the binding is hoping to be achieved can massively affect, percentages of positive cations, and temperature. In some cases, the reliability of attachment of the SNAPs to the solid support may be high. In some cases, the reliability of attachment of the SNAPs to the solid support may be moderate. In some cases, the reliability of attachment of the SNAPs to the solid support may be low.

In some embodiments, a portion or all of the solid support may be optically opaque. In some cases, a portion or all of the solid support may be optically clear at one or more wavelengths. In some cases, a portion or all of the solid support may be partially optically clear, or may be optically clear in some regions. For example, an optical coating on the solid support may be optically opaque in regions that are not functionalized, and optically clear in regions that are functionalized.

An example method for producing a solid support and integrated light sensing devices with attachment sites arrayed at desired intervals may begin with providing a substrate. In some embodiments, the substrate may be an array of light sensing devices (e.g., a commercially available array of light sensing devices). The substrate may comprise, for example, a CCD light sensing array, a CMOS devices light sensing array, a light sensing array with a combination of CCD and CMOS devices, a charge injection device (CID) light sensing array, or a JOT image sensor. In some embodiments, the substrate may be glass. In particular, in some embodiments, the substrate may be amorphous glass, fused silica, or quartz, among other examples. In some embodiments, the substrate may be silicon. In some embodiments, the thickness of the substrate may be less than 100 microns, 100 microns, 150 microns, 200 microns, 300 microns, 400 microns, 500 microns, 600 microns, 700 microns, 800 microns, 900 microns, 1 millimeter, 2 millimeters, or more than 2 millimeters.

Initially, the substrate may be cleaned, such as with a piranha cleaning. In some embodiments, a substrate may be cleaned using a strong acid so as to clean the substrate without etching the substrate. In some embodiments, the substrate may be cleaned using a detergent. Alternatively, the substrate may be cleaned with solvent, sonication or with plasma such as $O_2$ or $N_2$ plasma, or with a combination thereof.

Once the substrate has been cleaned, a chrome layer may be deposited on the backside of the substrate. Deposition methods may include, for example, evaporation or sputtering. In some embodiments, a backside chrome evaporation may not be applied when a substrate is opaque. A backside chrome evaporation may have a thickness of one Angstrom, two Angstroms, 10 Angstroms, 10 nanometers, 20 nanometers, 30 nanometers, 40 nanometers, 50 nanometers, 60 nanometers, 70 nanometers, 80 nanometers, 90 nanometers, 100 nanometers, 150 nanometers, 200 nanometers, 250 nanometers, 300 nanometers, 400 nanometers, 500 nanometers, or more than 500 nanometers. Alternatively, other metals can be used for deposition on the backside of the substrate, such as Aluminum, Tungsten, and/or Titanium, among other examples. Alternatively, dielectric mirrors can be used for deposition on the backside of the substrate.

Further, fiducials may be created on the front side of the substrate. Fiducials may be created by adding at least one layer of material and by patterning this at least one layer. In some embodiments, such material can be chrome, and/or such materials may be other metals like tungsten or gold. Alternatively, dielectric mirrors could be used as a material for fiducials. Alternatively, metal oxide could be used for the fiducials as for example $ZrO_2$. The patterning of such materials can be performed in a variety of ways. A first way to pattern the fiducial material may be to deposit a blanket layer of the material, then to protect this material in selected areas and remove the material in the areas where it is not protected. This can for example be achieved by coating the front side of the substrate with photosensitive material (e.g. photoresist), patterning this photoresist by exposing it to UV light through a mask and then developing it. The etching of the fiducial material can then be performed by wet etch (for example acid) or dry etch (for example Reactive Ion Etching, RIE). Alternatively, the photoresist may be deposited and patterned first. In some embodiments where the photoresist may be deposited and patterned first, areas are defined that are free of such photoresist and then the fiducial material may be deposited on top of the photoresist. The photoresist may then be removed (for example, in a solvent bath with sonication) and the fiducial material may be left on the areas that were initially free of photoresist (e.g., using a lift-off technique). Alternatively, fiducials may be created by removing material from the substrate in selected areas, for example by patterning a layer of photoresist on the front side of the substrate and then by dry etching the substrate in the areas that are not coated with photoresist. In an another alternative, fiducials may be defined by modifying the substrate locally (for example by laser melting and/or fractioning). Fiducials may come in a variety of shapes, lines, and/or orientations. In some embodiments, a pattern of fiducials may be applied to the substrate. In yet another embodiment, the shape of fiducials may vary in order to code information about their location on the surface of the substrate.

Once a pattern of fiducials may be created on the front side of the substrate, this front side may be differentially coated to define features where the biological objects of interest (for example, nucleic acid clusters covalently attached to a protein) may be immobilized. In a first embodiment, the surface may be differentially patterned with two silanes, for example HMDS or a PEG-silane in the field and APTES on the immobilization spots. This differential patterning may be achieved by, for example, depositing an initial HMDS layer on the surface, followed by a lift-off layer, followed by an optional anti-reflective layer, and followed by a photoresist layer. In some embodiments, an anti-reflective layer may not be provided when an opaque substrate is being used.

Once the photoresist may be applied, a second lithography step may be provided. In particular, desired features may be provided. In some embodiments, desired features may have a length of approximately 300 nm. In some embodiments, features may have a length of less than 50 nm, 100 nm, 150 nm, 200 nm, 250 nm, 300 nm, 350 nm, 400 nm, 450 nm, 500 nm, 600 nm, 700 nm, or more than 700 nm. In some further embodiments, one or more layers deposited on the surface to perform this second lithography may not be etched by the developing step of this second lithography (for example, the antireflective coating).

In embodiments where a backside coating may be provided, the backside coating may be removed, such as through the use of a wet etch or dry etch etc. Further, a directional reactive ion etch (RIE) may be provided so as to remove layers that haven't been removed by the lithography step (for example the antireflective coating).

Once the holes have been provided, cleaning may be performed. As seen in FIG. 2, an oxygen plasma cleaning and activation step may be provided. Once the chip has been cleaned, an amino-silane deposition may be provided. Once the amino-silane deposition may be provided, portions of the chip manufacture may be lifted-off, such as using hot DMF. Further, a sonication step may be performed. The resulting chip may be used in flow cells for assessments of biological assays.

In an alternative embodiment, the surface may be differentially patterned with a silane layer and a metal layer (for example, (3-Aminopropyl)triethoxysilane (APTES) on the immobilization spots and chrome in the field). In another embodiment, the surface may be differentially patterned with a silane layer and a metal oxide layer (for example a PEG-silane layer in the field and a $ZrO_2$ layer on the immobilization spots). In yet another embodiment, the surface may be differentially patterned with a silane layer on the immobilization spots (for example, acyl protein thioesterases (APTS)) and a metal oxide layer (for example a $ZrO_2$) and a PEG-phosphonic acid layer in the field.

The biological, chemical, or physical entities of this disclosure may be any biological, chemical, or physical entities for which spatial separation may be desired. In some embodiments, the biological, chemical, or physical entities are proteins. In some cases, the proteins may be proteins from a cell or tissue homogenate, from a biological fluid, or from an environmental sample. In some cases, the biological, chemical, or physical entities may be antibodies. In some embodiments the biological, chemical, or physical entities are nucleic acids. For example, the biological, chemical, or physical entities may be DNAs, RNAs, mRNAs, tRNAs, or miRNAs. In some embodiments the biological, chemical, or physical entities are carbohydrates. In some embodiments, the biological, chemical, or physical entities are complex polymers. In some embodiments the biological, chemical, or physical entities are small molecules, for example chemical compounds rather than complex polymers.

The biological, chemical, or physical entities of this disclosure may be attached to seeds. These seeds are molecules which can be used as a starting 'seed' to grow a larger polymeric molecule. The seed may be a monomer capable of being grown into a polymer, or may comprise a monomer capable of being grown into a polymer. Generally, the seeds are molecules which can be covalently attached to the molecules. The seeds may have a polarity such that only one functional group of the seed may be able to bind to a molecule of the molecules to be separated, while another one or more functional groups of the seed can form the starting point for a polymer.

Examples of monomers which may be present in the seeds include, but are not limited to, oligonucleotides, carbohydrates, proteins, amyloids, fibrils, and tetratricopeptide repeats. In some cases the seeds are small molecules.

The seeds may comprise a monomer and a functional group able to bind to a biological, chemical, or physical entity to be separated. Examples of such functional groups may include, but are not limited to, amines, thiols, carboxylic acids, triple bonds, double bonds, epoxides, alkynes, alkenes, cycloalkynes, azides, cyclo-octynes, cycloalkynes, norbornenes, tetrazines, cyclooctanes, epoxides, and hydroxyls. In some cases, the seed may comprise a functional group that is compatible with a click chemistry. In some cases, the seed may also comprise a linker or spacer between the seed and the functional group. In some cases, the linker or spacer may comprise a photo-cleavable bond. In some cases, the seed may comprise an oligonucleotide conjugated to an amine group on the 5' terminal. In some cases, the seed may comprise an oligonucleotide conjugated to a click chemistry component on the 5' terminal.

In some cases, bioconjugation may be used to form a covalent bond between two molecules, at least one of which may be a biomolecule. Bioconjugation may be formed but not limited to via chemical conjugation, enzymatic conjugation, photo-conjugation, thermal-conjugation, or a combination thereof. (Spicer, C. D., Pashuck, E. T., & Stevens, M. M., Achieving Controlled Biomolecule—Biomaterial Conjugation. Chemical Reviews, 2018, 118, Pgs. 7702-7743, and Greg T. Hermanson, "Bioconjugate Techniques", Academic Press; $3^{rd}$ Edition, 2013, herein incorporated by reference for this disclosure). In some cases, both the seed and the biological (e.g. SNAP), chemical, or physical entity may be functionalized. Functionalizing both partners may improve the efficiency or speed of a conjugation reaction. For example, a sulfhydryl group (—SH) or amine (—$NH_2$) of a chemically active site of a seed, biological, chemical, or physical entity may be functionalized to allow for greater reactivity or efficiency of a conjugation reaction. Any of a variety of sulfhydryl-reactive (or thiol-reactive) or amine conjugation chemistries may be used to couple chemical moieties to sulfhydryl or amine groups. Examples include, but are not limited to, use of haloacetyls, maleimides, aziridines, acryloyls, arylating agents, vinylsulfones, pyridyl disulfides, TNB-thiols and/or other sulfhydryl-reactive/amine-reactive/thiol-reactive agents. Many of these groups conjugate to sulfhydryl groups through either alkylation (e.g., by formation of a thioether or amine bond) or disulfide exchange (e.g., by formation of a disulfide bond). More strategies and detail regarding reactions for bioconjugation are described down below and may be extended to other appropriate biomolecules.

Bioconjugation can be accomplished in part by a chemical reaction of a chemical moiety or linker molecule with a chemically active site on the biomolecule. The chemical conjugation may proceed via an amide formation reaction, reductive amination reaction, N-terminal modification, thiol Michael addition reaction, disulfide formation reaction, copper(I)-catalyzed alkyne-azide cycloaddition (CuAAC) reaction, strain-promoted alkyne-azide cycloaddtion reaction (SPAAC), Strain-promoted alkyne-nitrone cycloaddition (SPANC), invers electron-demand Diels-Alder (IEDDA) reaction, oxime/hydrazone formation reaction, free-radical polymerization reaction, or a combination thereof. Enzyme-mediated conjugation may proceed via transglutaminases, peroxidases, sortase, SpyTag-SpyCatcher, or a combination thereof. Photoconjugated and activation may proceed via photoacrylate cross-linking reaction, photo thiol-ene reaction, photo thiol-yne reaction, or a combination thereof. In some cases, conjugation may proceed via noncovalent interactions, these may be through self-assembling peptides, binding sequences, host-guest chemistry, nucleic acids, or a combination thereof.

In some cases, site-selectivity methods may be employed to modify reaction moieties of biomolecules to increase conjugation efficiency, ease of use, reproducibility. Three common strategies are typically employed for site-selective bioconjugation (i) Modification strategies that can select a single motif among many, rather than targeting a generic reactive handle. This may be determined by surrounding a sequence, local environment, or subtle differences in reactivity. The ability of enzymes to modify a specific amino acid within a protein sequence or a glycan at a single position are particularly prominent. Reactions that display exquisite chemo-selectivity also fall within this category, such as those that target the unique reactivity of the protein N-terminus or the anomeric position of glycans. (ii) The site-specific incorporation of unnatural functionalities, by hijacking native biosynthetic pathways may be utilized. (iii) The installation of unique reactivity via chemical synthesis may be utilized. The complete or partial synthesis of peptides and oligonucleotides may be widespread, particularly using solid-phase approaches. These techniques allow access to sequences of up to 100 amino acids or 200 nucleotides, with the ability to install a wide variety of functionalized monomers with precise positional control.

In some cases, chemical conjugation techniques may be applied for creating biomaterial—biomolecule conjugates. Functional groups used for bioconjugation may be native to the biomolecule or may be incorporated synthetically. In the illustrations below, R and R' may be a biomolecule (for example, but not limited to: SNAP, proteins, nucleic acids, carbohydrates, lipids, metabolites, small molecules, monomers, oligomers, polymers) and/or a solid support.

In some cases, reductive amination may be utilized for bioconjugation. Amines can react reversibly with aldehydes to form a transient imine moiety, with accompanying elimination of water. This reaction takes place in rapid equilibrium, with the unconjugated starting materials being strongly favored in aqueous conditions due to the high concentration of water. However, in a second step the unstable imine can be irreversibly reduced to the corresponding amine via treatment with sodium cyanoborohydride. This mild reducing reagent enables the selective reduction of imines even in the presence of unreacted aldehydes. As a result, irreversible conjugation of a biomolecule can gradually occur to a biomaterial of interest. In contrast, stronger reducing agents such as sodium borohydride are also able to reduce aldehydes. This two-step reductive amination process can also be utilized for the modification of ketones. For example, reductive amination has therefore been primarily used for the modification of sodium periodate-treated alginate and chitosan scaffolds. The order of reactivity may also be reversed for the attachment of reducing sugars, by exploiting the terminal aldehyde/ketone generated in the open-chain form. This strategy, for example, may be exploited to mimic the glucosylation, glycosylation, and/or galactosylation patterns of native collagen in ECM, via reductive amination of maltose and lactose respectively.

In some cases, isothiocyanates of a biomolecule or solid support may be utilized for bioconjugation. For example, isothiocyanate of a biomolecule may react with nucleophiles such as amines, sulfhydryls, the phenolate ion of tyrosine side chains or other biomolecules to form a stable bond between two molecules.

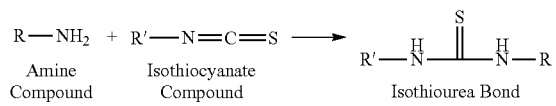

In some cases, an isocyanate of a biomolecule or solid support may be utilized for bioconjugation. For example, isocyanates can react with amine-containing molecules to form stable isourea linkages.

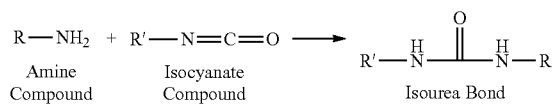

In some cases, an acyl azide of a biomolecule or solid support may be utilized for bioconjugation. For example, acyl azide are activated carboxylate groups that can react with primary amines to form amide bonds.

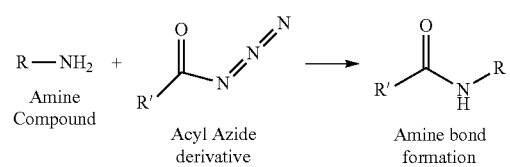

In some cases, an amide of a biomolecule or solid support may be utilized for bioconjugation. For example, the use of reactive N-hydroxysuccinimide (NHS) esters may be particularly widespread. While NETS-esters can be preformed, often they are instead generated in situ through the use of N-(3-(dimethylamino)propyl)-N'-ethylcarbodiimide (EDC) coupling chemistry and coupled directly to the species of interest. Although formation of the activated NETS-ester may be favored under mildly acidic conditions (pH ~5), subsequent amide coupling may be accelerated at higher pHs at which the amine coupling partner may be not protonated. One-step modification at an intermediate pH of ~6.5 may be possible. Conjugation may be typically undertaken by first forming the active NHS-ester at pH 5, before raising the pH to ~8 and adding the amine coupling partner in a two-step procedure. In some cases, water-soluble derivative sulfo-NHS may be utilized as an alternative. In some cases, NETS esters of a biomolecule can react and couple with tyrosine, serine, and threonine —OH groups as opposed to N-terminal α-amines and lysine side-chain ε-amines.

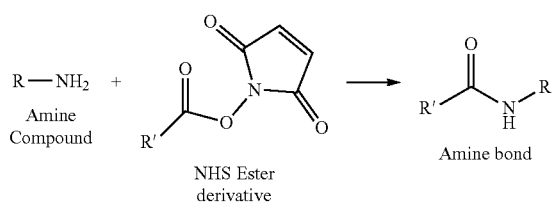

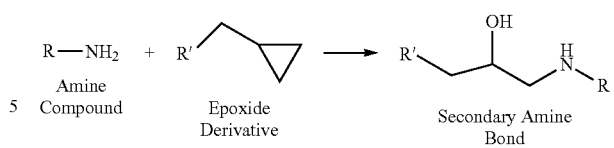

In some cases, a sulfonyl chloride of a biomolecule or solid support may be utilized for bioconjugation. For example, reaction of a sulfonyl chloride compound with a primary amine-containing molecule proceeds with loss of the chlorine atom and formation of a sulfonamide linkage.

In some cases, a carbonate of a biomolecule or solid support may be utilized for bioconjugation. For example, carbonates may react with nucleophiles to form carbamate linkages, disuccinimidyl carbonate, can be used to activate hydroxyl-containing molecules to form amine-reactive succinimidyl carbonate intermediates. In some cases, this carbonate activation procedure can be used in coupling polyethylene glycol (PEG) to proteins and other amine-containing molecules. In some cases, nucleophiles, such as the primary amino groups of proteins, can react with the succinimidyl carbonate functional groups to give stable carbamate (aliphatic urethane) bonds

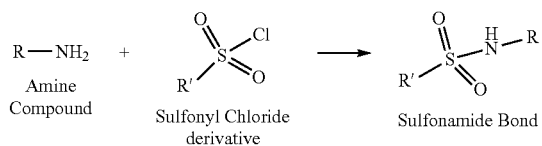

In some cases, a tosylate ester of a biomolecule or solid support may be utilized for bioconjugation. For example, reactive groups comprising tosylate esters can be formed from the reaction of 4-toluenesulfonyl chloride (also called tosyl chloride or TsCl) with a hydroxyl group to yield the sulfonyl ester derivative. The sulfonyl ester may couple with nucleophiles to produce a covalent bond and may result in a secondary amine linkage with primary amines, a thioether linkage with sulf-hydryl groups, or an ether bond with hydroxyls.

In some cases, a carbonyl of a biomolecule or solid support may be utilized for bioconjugation. For example, carbonyl groups such as aldehydes, ketones, and glyoxals can react with amines to form Schiff base intermediates which are in equilibrium with their free forms. In some cases, the addition of sodium borohydride or sodium cyanoborohydride to a reaction medium containing an aldehyde compound and an amine-containing molecule will result in reduction of the Schiff base intermediate and covalent bond formation, creating a secondary amine linkage between the two molecules.

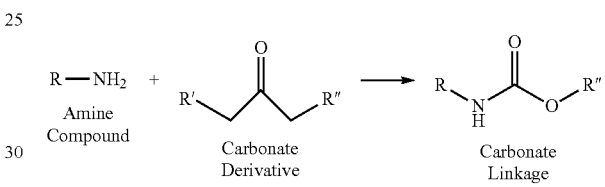

In some cases, an aryl halide of a biomolecule or solid support may be utilized for bioconjugation. For example, aryl halide compounds such as fluorobenzene derivatives can be used to form covalent bonds with amine-containing molecules like proteins. Other nucleophiles such as thiol, imidazolyl, and phenolate groups of amino acid side chains can also react to form stable bonds with a biomolecule or solid support. In some cases, fluorobenzene-type compounds have been used as functional groups in homobifunctional crosslinking agents. For example, their reaction with amines involves nucleophilic displacement of the fluorine atom with the amine derivative, creating a substituted aryl amine bond.

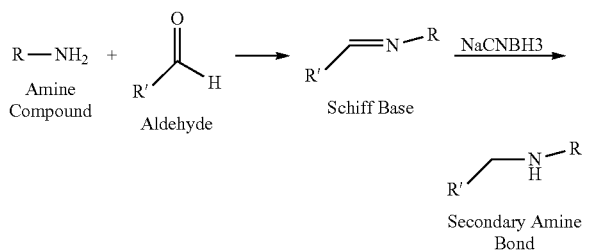

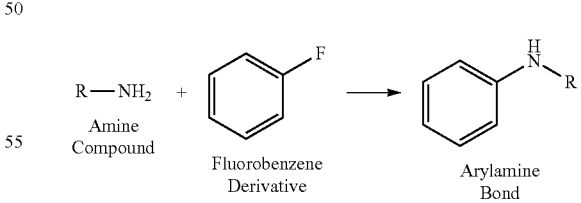

In some cases, an epoxide or oxirane of a biomolecule or solid support may be utilized for bioconjugation. For example, an epoxide or oxirane group of a biomolecule may react with nucleophiles in a ring-opening process. The reaction can take place with primary amines, sulfhydryls, or hydroxyl groups to create secondary amine, thioether, or ether bonds, respectively.

In some cases, an imidoester of a biomolecule or solid support may be utilized for bioconjugation. For example, the α-amines and ε-amines of proteins may be targeted and crosslinked by reacting with homobifunctional imidoesters. In some cases, after conjugating two proteins with a bifunctional imidoester crosslinker, excess imidoester functional groups may be blocked with ethanolamine.

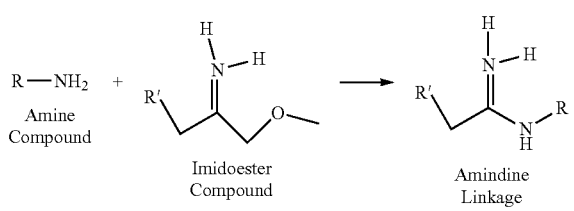

In some cases, carbodiimides may be utilized for bioconjugation. Generally, carbodiimides are zero-length crosslinking agents that may be used to mediate the formation of an amide or phosphoramidate linkage between a carboxylate group and an amine or a phosphate and an amine, respectively. Carbodiimides are zero-length reagents because in forming these bonds no additional chemical structure may be introduced between the conjugating molecules. In some cases, N-substituted carbodiimides can react with carboxylic acids to form highly reactive, O-acylisourea derivatives. This active species may then react with a nucleophile such as a primary amine to form an amide bond. In some cases, sulfhydryl groups may attack the active species and form thioester linkages. In some cases, hydrazide-containing compounds can also be coupled to carboxylate groups using a carbodiimide-mediated reaction. Using bifunctional hydrazide reagents, carboxylates may be modified to possess terminal hydra-zide groups able to conjugate with other carbonyl compounds.

In some cases, a biomolecule containing phosphate groups, such as the 5' phosphate of oligonucleotides, may also be conjugated to amine-containing molecules by using a carbodiimide-mediated reaction. For example, the carbodiimide of a biomolecule may activate the phosphate to an intermediate phosphate ester similar to its reaction with carboxylates. In the presence of an amine, the ester reacts to form a stable phosphoramidate bond.

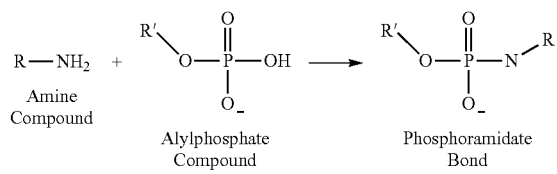

In some cases, an acid anhydride of a biomolecule or solid support may be utilized for bioconjugation. Anhydrides are highly reactive toward nucleophiles and are able to acylate a number of the important functional groups of proteins and other biomolecules. For example, protein functional groups able to react with anhydrides include but not limited to the α-amines at the N-terminals, the ε-amine of lysine side chains, cysteine sulfhydryl groups, the phenolate ion of tyrosine residues, and the imid-azolyl ring of histidines. In some cases, the site of reactivity for anhydrides in protein molecules may be modification of any attached carbohydrate chains. In some cases, in addition to amino group modification in a polypeptide chain, glycoproteins may be modified at their polysaccharide hydroxyl groups to form esterified derivatives.

In some cases, a fluorophenyl ester of a biomolecule or solid support may be utilized for bioconjugation. Fluorophenyl esters can be another type of carboxylic acid derivative that may react with amines consists of the ester of a fluorophenol compound, which creates a group capable of forming amide bonds with proteins and other molecules. In some cases, fluorophenyl esters may be: a pentafluorophenyl (PFP) ester, a tetrafluorophenyl (TFP) ester, or a sulfotetrafluoro-phenyl (STP) ester. In some cases, fluorophenyl esters react with amine-containing molecules at slightly alkaline pH values to give the same amide bond linkages as NHS esters.

In some cases, hydroxymethyl phosphine of a biomolecule or solid support may be utilized for bioconjugation. Phosphine derivatives with hydroxymethyl group substitutions may act as bioconjugation agents for coupling or crosslinking purposes. For example, tris(hydroxymethyl) phosphine (THP) and β-[tris(hydroxymethyl)phos-phino] propionic acid (THPP) are small trifunctional compounds that spontaneously react with nucleophiles, such as amines, to form covalent linkages.

In some cases, the thiol reactivity of a biomolecule or solid support may be utilized for bioconjugation. For example, the thiol group of cysteine may be the most nucleophilic functional group found among the 20 proteinogenic amino acids. Through careful control of pH, selective modification over other nucleophilic residues such as lysine can be readily achieved. Another example, thiol modification of oligonucleotides may be used to enable derivatization, though the ease with which alternative reactive handles with enhanced chemical orthogonality can be installed has limited use for biomaterial-conjugation. Further, the conjugate addition of thiols to α,β-unsaturated carbonyls, also known as Michael addition, may be used to form polypeptide conjugates in the fields of tissue engineering, functional materials, and protein modification. In general, reaction rates and conjugation efficiencies are primarily controlled by three factors and may be modified as needed: (i) the $pK_a$ of the thiol; (ii) the electrophilicity of the Michael-acceptor; (iii) the choice of catalyst. Regarding (i): the thiolate anion may be the active nucleophile during Michael addition, and the propensity of the thiol to undergo deprotonation may determine thiolate concentration and thus reaction rates. For example, the lower $pK_a$ of aromatic thiols, when compared to their aliphatic counterparts, leads to a higher rate of reaction rate a weak base may be used to catalyze the. As a result, local structure can significantly alter conjugation efficiency, particularly for polypeptide substrates. The $pK_a$ and reactivity of cysteine containing peptides can be altered significantly through rational choice of surrounding amino acids, the presence of positively charged amino acids, such as lysine and arginine, acts to lower the thiol $pK_a$ and thus enhance reactivity. Regarding (ii): the Michael-acceptor becomes more electron deficient it becomes more activated toward nucleophilic attack, and thus reaction rates increase. Within the most widely utilized acceptors in the biomaterial field, a trend of reactivity can be generalized as maleimides>vinyl sulfones>acrylates>acrylamides>methacrylates. Regarding (iii) Michael additions can be accelerated by either basic or nucleophilic catalysis (although both act by increasing the concentration of the active thiolate).

In some cases, the unique nucleophilicity of thiols can be exploited for selective reaction with a number of alternative electrophiles, which allow efficient and selective biomolecule attachment to be achieved. For example, one such group are α-halocarbonyls, with iodoacetamide based reagents finding particular utility. Higher thiol selectivity may be achieved using less electrophilic bromo and even chloro derivatives, though reactivity may be also drastically reduced. More recently, methylsulfonyl heteroaromatic derivatives have emerged as promising reagents for thiol-specific conjugation. In other cases, alternative thiol-reactive handles, such as disulfide-bridging pyridazinediones, carbonylacrylic reagents, and cyclopropenyl ketones may be utilized for bioconjugation.

In some cases, sulfhydryl of a biomolecule or solid support may be utilized for bioconjugation. In some cases, three forms of activated halogen derivatives can be used to create sulfhydryl-reactive compounds: haloacetyl, benzyl halides, and alkyl halides. In each of these compounds, the halogen group may be easily displaced by an attacking nucleophilic substance to form an alkylated derivative with loss of HX (where X is the halogen and the hydrogen comes from the nucleophile). Haloacetyl compounds and benzyl halides typically are iodine or bromine derivatives, whereas the halo-mustards mainly employ chlorine and bromine forms. Iodoacetyl groups have also been used successfully to couple affinity ligands to chromatography supports.

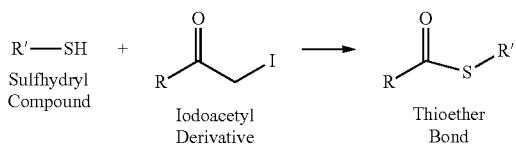

In some cases, a maleimide of a biomolecule or solid support may be utilized for bioconjugation. The double bond of maleimides may undergo an alkylation reaction with sulfhydryl groups to form stable thioether bonds.

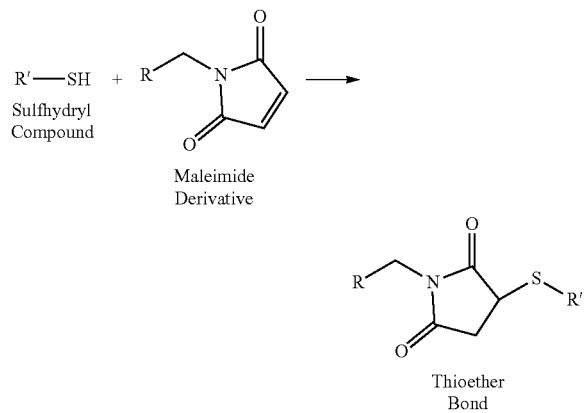

In some cases, an aziridine of a biomolecule or solid support may be utilized for bioconjugation. The highly hindered nature of this heterocyclic ring gives it strong reactivity toward nucleophiles. For example, sulfhydryls will react with aziridine-containing reagents in a ring-opening process, forming thioether bonds. The simplest aziridine compound, ethylenimine, can be used to transform available sulfhydryl groups into amines. In some cases, substituted aziridines may be used to form homobifunctional and trifunctional crosslinking agents.

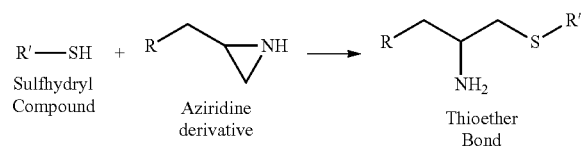

In some cases, thiol-maleimide reactions are particularly useful for undertaking conjugation at low concentrations or when requiring extremely high efficiencies due to the value of the biomolecule substrate. The use of maleimides in bioconjugation may be further enhanced by the ease with which they may be introduced into a wide range of scaffold materials, through the modification of amines with the difunctional reagent succinimidyl 4-(N-maleimidomethyl) cyclohexane-1-carboxylate, more commonly referred to by its abbreviation SMCC. For example, this reagent has been widely used to first introduce a maleimide reactive handle on a biomaterial of choice and then to enable the attachment of both peptides and growth factors to produce bioactive scaffolds.

In some cases, an acryloyl of a biomolecule or solid support may be utilized for bioconjugation. The reactive double bonds are capable of undergoing additional reactions with sulfhydryl groups. In some cases, the reaction of an acryloyl compound with a sulfhydryl group occurs with the creation of a stable thioether bond. In some cases, the acryloyl has found use in the design of the sulfhydryl-reactive fluorescent probe, 6-acryloyl-2-dimethylaminonaphthalene.

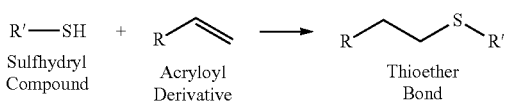

In some cases, an aryl group of a biomolecule or solid support may be utilized for bioconjugation with a sulfhydryl group. Although aryl halides are commonly used to modify amine-containing molecules to form aryl amine derivatives, they also may react quite readily with sulfhydryl groups. For example, fluorobenzene-type compounds have been used as functional groups in homobifunctional crosslinking agents. Their reaction with nucleophiles involves bimolecular nucleophilic substitution, causing the replacement of the fluorine atom with the sulfhydryl derivative and creating a substituted aryl bond. Conjugates formed with sulfhydryl groups are reversible by cleaving with an excess of thiol (such as DTT).

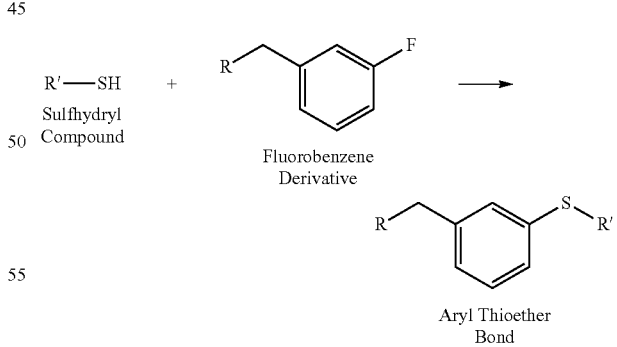

In some cases, the disulfide group of a biomolecule or solid support may be utilized for bioconjugation. In some cases, compounds containing a disulfide group are able to participate in disulfide exchange reactions with another thiol. The disulfide exchange (also called interchange) process involves attack of the thiol at the disulfide, breaking the —S—S— bond, with subsequent formation of a new mixed disulfide comprising a portion of the original disulfide compound. The reduction of disulfide groups to sulfhydryls in proteins using thiol-containing reductants proceeds through the intermediate formation of a mixed disulfide. In some cases, crosslinking or modification reactions may use disulfide exchange processes to form disulfide linkages with sulfhydryl-containing molecules.

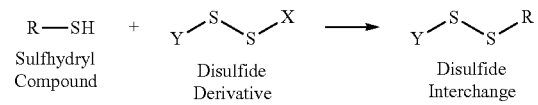

In some cases, disulfide bonds may be utilized for bioconjugation. For example, the use of disulfide exchange reactions may be favored for introducing peptides or proteins of interest. The most commonly used reagents in tissue engineering are based upon reactive pyridylthio-disulfides, which undergo rapid thiol-exchange to release the poorly nucleophilic and spectroscopically active 2-mercaptopyridine. Additionally, due to the reversible nature of disulfide bond formation, cleavage can be controlled with temporal precision by the addition of reducing agents such as dithiothreitol (DTT) or glutathione.

In some cases, a pyridyl dithiol functional group may be used in the construction of crosslinkers or modification reagents for bioconjugation. Pyridyl disulfides may be created from available primary amines on molecules through the reaction of 2-iminothiolane in tandem with 4,4'-dipyridyl disulfide. For instance, the simultaneous reaction among a protein or other biomolecule, 2-iminothiolane, and 4,4'-dipyri-dyl disulfide yields a modification containing reactive pyridyl disulfide groups in a single step. A pyridyl disulfide will readily undergo an interchange reaction with a free sulfhydryl to yield a single mixed disulfide product.

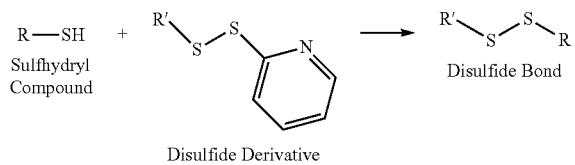

In some cases, sulfhydryl groups activated with the leaving group 5-thio-2-nitrobenzoic acid can be used to couple free thiols by disulfide interchange similar to pyridyl disulfides, as described herein. The disulfide of Ellman's reagent readily undergoes disulfide exchange with a free sulfhydryl to form a mixed disulfide with concomitant release of one molecule of the chromogenic substance 5-sulfido-2-nitroben-zoate, also called 5-thio-2-nitrobenzoic acid (TNB). The TNB-thiol group can again undergo interchange with a sulfhydryl-containing target molecule to yield a disulfide crosslink. Upon coupling with a sulfhydryl compound, the TNB group is released.

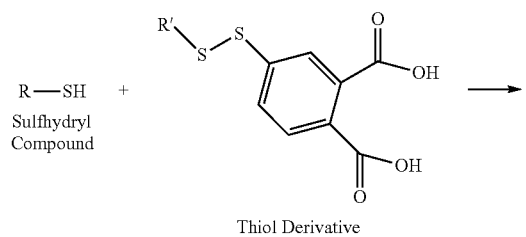

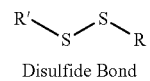

In some cases, disulfide reduction may be performed using thiol-containing compounds such as TCEP, DTT, 2-mercaptoethanol, or 2-mercaptoethylamine.

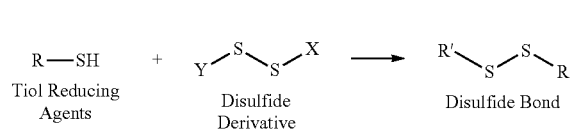

In some cases, a vinyl sulfone group of a biomolecule or solid support may be utilized for bioconjugation. For example, the Michael addition of thiols to activated vinyl sulfones to form biomolecule-material conjugates have been used to demonstrate that cysteine capped peptides could cross-link vinyl-sulfone functionalized multiarm PEGs to form protease responsive hydrogels, enabling cell invasion during tissue growth. In some cases, in addition to thiols, vinyl sulfone groups can react with amines and hydroxyls under higher pH conditions. The product of the reaction of a thiol with a vinyl sulfone gives a single stereoisomer structure. In addition, crosslinkers and modification reagents containing a vinyl sulfone can be used to activate surfaces or molecules to contain thiol-reactive groups.

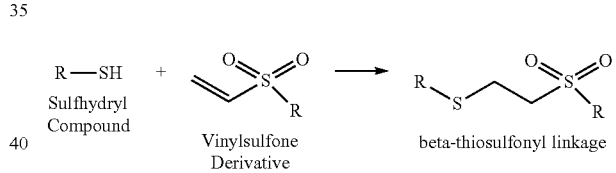

In some cases, thiol-containing biomolecules can interact with metal ions and metal surfaces to form dative bonds for bioconjugation. In some cases, oxygen- and nitrogen-containing organic or biomolecules may be used to chelate metal ions, such as in various lanthanide chelates, bifunctional metal chelating compounds, and FeBABE. In addition, amino acid side chains and prosthetic groups in proteins frequently form bioinorganic motifs by coordinating a metal ion as part of an active center.

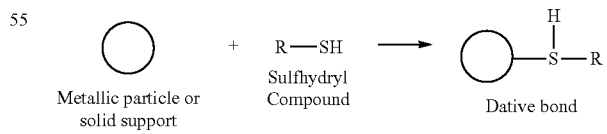

In some cases, thiol organic compounds may be used routinely to coat metallic surfaces or particles to form biocompatible layers or create functional groups for further conjugation of biomolecules. For instance, thiol-containing aliphatic/PEG linkers have been used to form self-assembled monolayers (SAMs) on planar gold surfaces and particles.

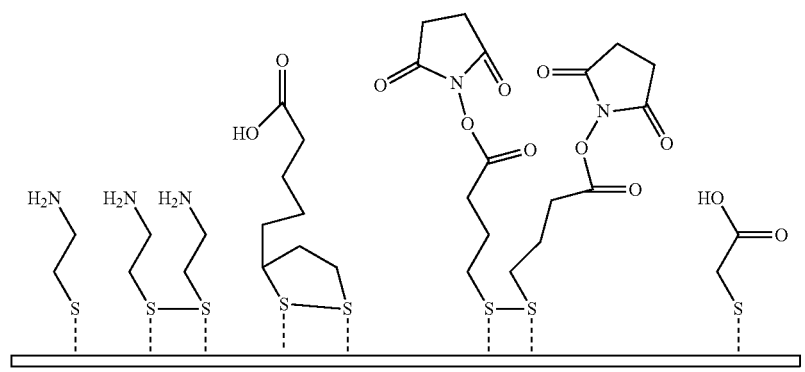

In some cases, a number of alternative coupling systems may be used for biomolecule functionalization. These include the use of O-nitrophenyl esters (which possess reduced stability in aqueous conditions) or 1,1'-carbonyldiimidazole (CDI) to form amine-bridging carbamate linkages rather than amides. Hydrazines can also be used in place of amines during EDC/NHS mediated couplings. Hydrazine-functionalized peptides can be coupled to biomaterials in a single step at pH 5-6. In doing so, a degree of site-selectivity can be achieved over lysine residues present. This approach has been successfully implemented by Madl and co-workers to conjugate reactive groups to alginate hydrogels, enabling indirect functionalization with growth factors and adhesion peptides.

In some cases, N-terminal modification of a biomolecule may be utilized for bioconjugation. For example, 2-pyridinecarboxaldehyde modified acrylamide hydrogels may react specifically with the N-terminus of ECM proteins, forming a cyclic imidazolidinone product with the adjacent amide bond and enabling the orientated display of these key bioinstructive motifs.

In some cases, acrylates, acrylamides, and methacrylates of a biomolecule or solid support may be utilized for bioconjugation. In some cases, thiol-ynes of a biomolecule or solid support may be utilized for bioconjugation.

In some cases, thiol-reactive conjugation such as native chemical ligation (NCL) can be utilized to attach peptides and proteins to biomaterial scaffolds via peptide bond formation. For example, a peptide having a C-terminal thioester reacts with an N-terminal cysteine residue in another peptide to undergo a trans-thioesterification reaction, which results in the formation of an intermediate thioester with the cysteine thiol.

In some cases, strong binding of (strept)avidin may be used for the small molecule biotin for bioconjugation. In some cases, (strept)avidin and biotin may be attached to a biomolecule or solid support for bioconjugation. In some cases, modification reagents can add a functional biotin group to proteins, nucleic acids, and other biomolecules. In some cases, depending on the functionality present on the biotinylation compound, specific reactive groups on antibodies or other proteins may be modified to create a (strept) avidin binding site. Amines, carboxylates, sulfhydryls, and carbohydrate groups can be specifically targeted for biotinylation through the appropriate choice of biotin derivative. In some cases, photoreactive biotinylation reagents are used to add nonselectively a biotin group to molecules containing no convenient functional groups for modification. In some cases, biotin-binding proteins can be immobilized onto surfaces, chromatography supports, microparticles, and nanoparticles for use in coupling biotinylated molecules. In some cases, a series of (strept)avidin-biotin interactions can be built upon each other to utilize the multivalent nature of each tetrameric (strept)avidin molecule and enhance the detection capability for the target. In some cases, amine-reactive biotinylation reagents that may contain reactive groups off biotin's valeric acid side chain are able to form covalent bonds with primary amines in proteins and other molecules. In some cases, NHS esters spontaneously react with amines to form amide linkages whereas carboxylate-containing biotin compounds can be coupled to amines via a carbodiimide-mediated reaction using EDC. In some cases, NHS—iminobiotin can be used to label amine-containing molecules with an iminobiotin tag, providing reversible binding potential with avidin or streptavidin. In some cases, Sulfo-NHS—SS-biotin (also known as NHS—SS-biotin) may be sulfosuccinimidyl-2-(biotinamido)ethyl-1,3-dithiopropionate, a long-chain cleavable biotinylation reagent that can be used to modify amine-containing proteins and other molecules. In some cases, 1-biotinamido-4-[4'-(maleimidomethyl) cyclohexane-carboxamido]butane, a biotinylation reagent containing a maleimide group at the end of an extended spacer arm reacts with sulfhydryl groups in proteins and other molecules to form stable thioether linkages. In some cases, N-[6-(biotinamido)hexyl]-3'-(2'-pyridyldithio)propionamide where the reagent contains a 1,6-diaminohexane spacer group which is attached to biotin's valeric acid side chain, the terminal amino group of the spacer may be further modified via an amide linkage with the acid precursor of SPDP to create a terminal, sulfhydryl-reactive group. The pyridyl disulfide end of biotin-HPDP may react with free thiol groups in proteins and other molecules to form a disulfide bond with loss of pyridine-2-thione.

In some cases, a carboxylate of a biomolecule or solid support may be utilized for bioconjugation. In some cases, diazomethane and other diazoalkyl derivatives may be used to label caroxylate groups. In some cases, N,N'-Carbonyl diimidazole (CDI) may be used to react with carboxylic acids under nonaqueous conditions to form N-acylimidazoles of high reactivity. An active carboxylate can then react with amines to form amide bonds or with hydroxyl groups to form ester linkages. In addition, activation of a styrene/4-vinylbenzoic acid copolymer with CDI may be used to immobilize an enzyme lysozyme or other biomolecule through its available amino groups to the carboxyl groups on to a matrix.

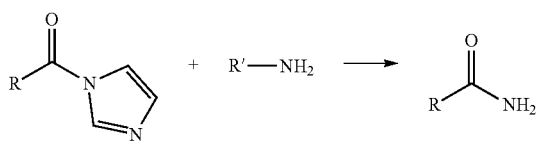

In some cases, carbodiimides function as zero-length crosslinking agents capable of activating a carboxylate group for coupling with an amine-containing compound for bioconjugation or a solid support. In some cases, carbodiimides are used to mediate the formation of amide or phosphoramidate linkages between a carboxylate and an amine or a phosphate and an amine.

In some cases, N,N'-disuccinimidyl carbonate or N-hydroxysuccinimidyl chloroformate may be utilized in bioconjugation. N,N'-Disuccinimidyl carbonate (DSC) consists of a carbonyl group containing, in essence, two NHS esters. The compound may be highly reactive toward nucleophiles. In aqueous solutions, DSC will hydrolyze to form two molecules of N-hydroxysuccinimide (NHS) with release of one molecule of $CO_2$. In nonaqueous environments, the reagent can be used to activate a hydroxyl group to a succinimidyl carbonate derivative. DSC-activated hydroxylic compounds can be used to conjugate with amine-containing molecules to form stable crosslinked products.

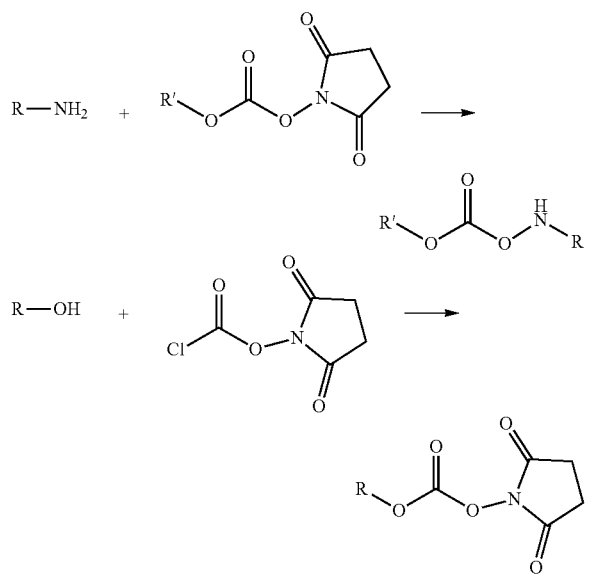

In some cases, sodium periodate can be used to oxidize hydroxyl groups on adjacent carbon atoms, forming reactive aldehyde residues suitable for coupling with amine- or hydrazide-containing molecules for bioconjugation. For example, these reactions can be used to generate crosslinking sites in carbohydrates or glyco-proteins for subsequent conjugation of amine-containing molecules by reductive amination.

In some cases, enzymes may be used to oxidize hydroxyl-containing carbohydrates to create aldehyde groups for bioconjugation. For example, the reaction of galactose oxidase on terminal galactose or N-acetyl-d-galactose residues proceeds to form C-6 aldehyde groups on polysaccharide chains. These groups can then be used for conjugation reactions with amine- or hydrazide-containing molecules.

In some cases, reactive alkyl halogen compounds can be used to specifically modify hydroxyl groups in carbohydrates, polymers, and other biomolecules for bioconjugation.

In some cases, an aldehyde or ketone of a biomolecule or solid support may be used for bioconjugation. For example, derivatives of hydrazine, especially the hydrazide compounds formed from carboxylate groups, can react specifically with aldehyde or ketone functional groups in target biomolecules. To further stabilize the bond between a hydrazide and an aldehyde, the hydrazone may be reacted with sodium cyanoborohydride to reduce the double bond and form a secure covalent linkage.

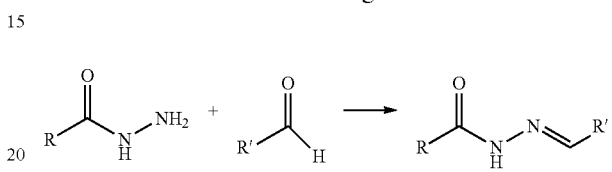

In some cases, an aminooxy group of a biomolecule or solid support may be used for bioconjugation. For example, the chemoselective ligation reaction that occurs between an aldehyde group and an aminooxy group yields an oxime linkage (aldoxime) that has been used in many bioconjugation reactions, as well as in the coupling of ligands to insoluble supports including surfaces. This reaction may be also quite efficient with ketones to form an oxime called a ketoxime.

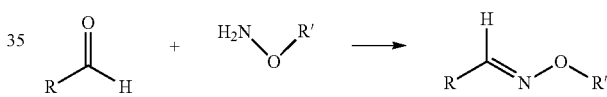

In some cases, cycloaddition reactions may be utilized for bioconjugation. In cycloaddition reactions for bioconjugation, two or more unsaturated molecules are brought together to form a cyclic product with a reduction in the degree of unsaturation, these reaction partners required are typically absent from natural systems, and so the use of cycloadditions for conjugation requires the introduction of unnatural functionality within the biomolecule coupling partner.

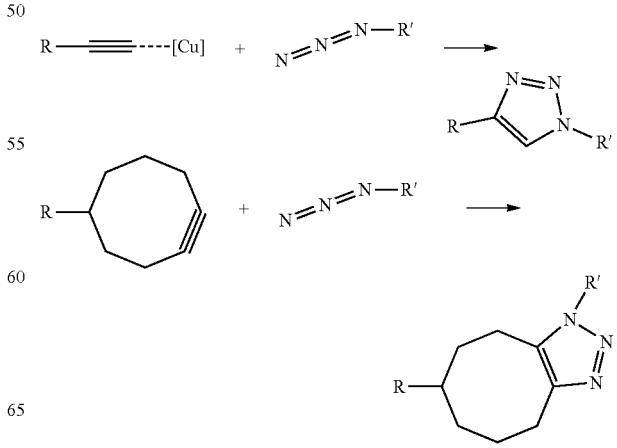

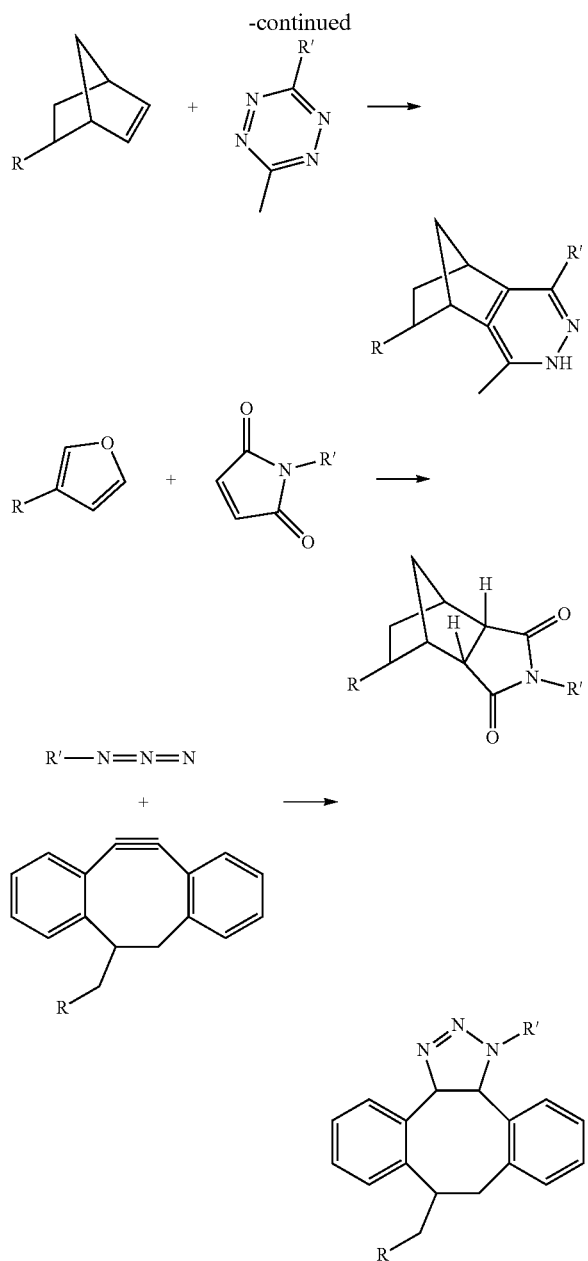

In some cases, Copper-Catalyzed Azide—Alkyne Cycloadditions may be utilized for bioconjugation. In some cases, the (3+2) cycloaddition between an azide and alkyne proceeds spontaneously at high temperatures (>90° C.), producing a mixture of two triazole isomers. In some cases, this reaction proceeds at room temperature, ambient, oxygenated, and/or aqueous environments. In some cases, for example, the formation of peptide—material conjugates by CuAAC, using alkyne-capped peptides to form hydrogels with azide-functionalized PEG. In some cases, CuAAC has been widely used to functionalize scaffolds with alkyne and azide functionalized peptides and carbohydrates, in part due to the ease with which the amino acids azidolysine and homopropargylglycine can be introduced by solid-phase peptide synthesis. In some cases, To achieve biomaterial conjugation via CuAAC, the required copper(I) catalyst can either be added directly, or generated in situ by reduction of an initial copper(II) complex, most commonly using ascorbic acid. The addition of a reducing agent further reduces the sensitivity of the CuAAC ligation to oxygen. Although no additional ligand is necessary for triazole formation, the addition of tertiary amine based ligands may be used.

In some cases, Strain-Promoted Azide—Alkyne Cycloadditions (SPAAC) may be utilized for bioconjugation. In some cases, highly strained cyclooctynes react readily with azides to form triazoles under physiological conditions, without the need for any added catalyst. In some cases, in addition to the use of SPAAC for peptide conjugation, a number of prominent reports have used SPAAC to conjugate protein substrates to cyclooctyne functionalized biomaterials via the introduction of an unnatural azide motif into the protein coupling partner. In some cases, for example, this may be achieved by including maleimide functionalization of native cysteines present in bone morphogenetic protein-2 (BMP-2), via enzyme-mediated N-terminal modification of IFN-γ, or via codon reassignment with the unnatural amino acid 4-azidophenylalanine in a number of protein substrates. In some cases, supramolecular host—guest interactions can also be used to promote azide—alkyne cycloaddition. For example, by bringing two reactive partners into close proximity within the cavity of a cucurbit[6]uril host, efficient cycloaddition could be achieved on the surface of proteins, this strategy may be extended to other appropriate biomolecules.

In some cases, inverse-electron demand Diels—Alder reactions (IEDDA) may be utilized for bioconjugation. For example, the inverse-electron demand Diels—Alder (IEDDA) reaction between 1,2,4,5-tetrazines and strained alkenes or alkynes may be employed. A wide range of suitable derivatives for undertaking biomolecule conjugation have been reported, for example, a series of increasingly strained (and thus reactive) trans-cyclooctenes may be utilized. In some cases, functionalized norbornene derivatives may be utilized for undertaking IEDDA reactions. In some cases, triazines may be utilized. In some cases, spirohexene may be utilized. These strategies may be extended to other appropriate biomolecules. In some cases, hetero-Diels-Alder cycloaddition of maleimides and furans may be utilized for bioconjugation. For example, the coupling of furan-functionalized RGDS peptides to maleimide-functionalized PEG-hydrogels may be utilized, this strategy may be extended to other appropriate biomolecules. In some cases, furan-functionalized hyraluronic acid hydrogels can be cross-linked with a dimaleimide-functionalized peptide via Diels-Alder cycloaddition. MMP-cleavable peptides enable the migration of seeded cancer through the gel.

In some cases, oxime and hydrazone formation may be utilized for bioconjugation. In some cases, the stable attachment of peptides and DNA to biomaterials via hydrazone formation can be achieved via difunctional cross-linking, this strategy may be extended to other appropriate biomolecules. In some cases, the attachment of ketone or aldehyde modified green fluorescent protein (GFP) or metallothionein to hydroxylamine-functionalized synthetic polymers may be extended to other appropriate biomolecules. For example, protein cross-linked hydrogels were produced through oxime modification at both the protein N- and C-termini.

In some cases, the Diels-Alder reaction consists of the covalent coupling of a diene with an alkene to form a six-membered ring complex for bioconjugation.

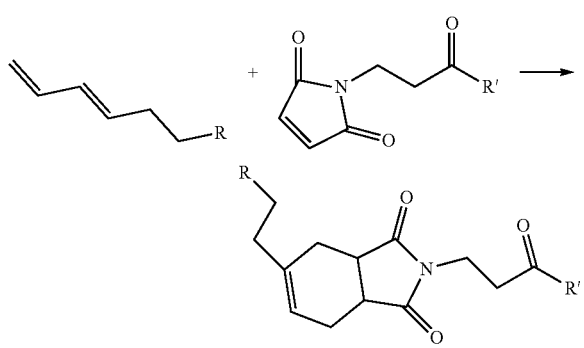

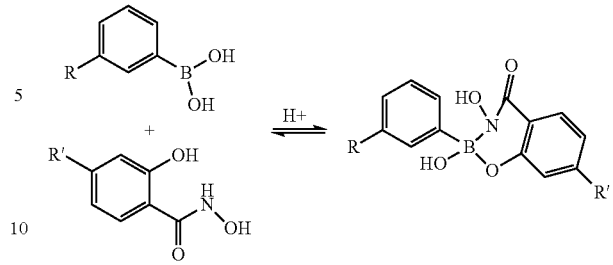

In some cases, transition metal complexes may be utilized for bioconjugation. The nature of late transition metals may make a transition metal complex well suited to the manipulation of unsaturated and polarizable functional groups (olefins, alkynes, aryl iodides, arylboronic acids, etc.). For example, Pd(0)-functionalized microspheres may mediate allyl carbamate deprotections and Suzuki-Miyaura cross-coupling in the cytoplasm. In other examples, a ruthenium catalyst may be used to mediate allyl carbamate deprotection of a caged fluorophore inside living cells. In some cases, applications of palladium-based applications in cell culture include copper-free Sonagashira coupling, extracellular Suzuki coupling on the surface of E. coli cells, and conjugation of thiol groups with allyl selenosulfate salts. In some cases, olefin metathesis may be utilized for bioconjugation. For example, with ruthenium complexes, S-allylcysteine can be easily introduced into proteins by a variety of methods, including conjugate addition of allyl thiol to dehydroalanine, direct allylation of cysteine, desulfurization of allyl disulfide, or metabolic incorporation as a methionine surrogate in methionine auxotrophic E. coli.

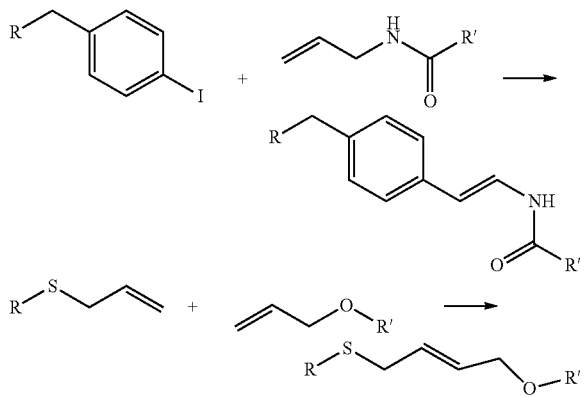

In some cases, complex formation with boronic acid derivatives may be used for bioconjugation. For example, boronic acid derivatives are able to form ring structures with other molecules having neighboring functional groups consisting of 1,2- or 1,3-diols, 1,2- or 1,3-hydroxy acids, 1,2- or 1,3-hydroxylamines, 1-2- or 1,3-hydroxyamides, 1,2- or 1,3-hydroxyoximes, as well as various sugars or biomolecules containing these species.

In some cases, enzyme-mediated conjugation may be utilized for bioconjugation. For example, the transglutaminase enzyme family catalyzes the formation of isopeptide bonds between the primary amine of lysine side chains and the amide bonds of a complementary glutamine residue, this strategy may be extended to other appropriate biomolecules. In other cases, peroxidase-mediated conjugation may be utilized for bioconjugation. For example, horse radish peroxidase (HRP) may be utilized to oxidize a wide range of organic substrates such as phenol group of tyrosine to generate a highly reactive radical or quinone intermediate that undergoes spontaneous dimerization, resulting in the formation of an ortho carbon-carbon bond between two tyrosine residues, this strategy may be extended to other appropriate biomolecules. In some cases, short peptide tags may be utilized for bioconjugation. These peptide tags may be as short as 5 amino acids long and may be appended to a peptide or protein substrate which allows for their subsequent modification.

In some cases, polymerization of low molecular weight monomers may be utilized for bioconjugation. Polymerization may be classified as proceeding via one of two mechanisms, either chain-growth or step-growth. During chain-growth polymerization, monomers are added at the "active" end of a growing polymer chain, resulting in the formation of high molecular weight materials even at low conversions. During step-growth polymerizations short oligomer chains couple to form polymeric species, requiring high conversions in order to reach high molecular weights. Both techniques can be used to form biomolecule—polymer conjugates. The polymerization of acrylate and methacrylate monomers has proven particularly fruitful. For example, acrylate and methacrylate modified peptides and glycans can be readily polymerized. Similarly, availability of the synthetic oligonucleotide phosphoramidite building block "Acrydite", free-radical polymerization remains one of the most common methods through which to form DNA and RNA functionalized biomaterials. By undertaking polymerization in the presence of a comonomer, the density of biomolecule presentation can be easily tuned, allowing potential difficulties from steric hindrance to be overcome. Initiation of polymerization can be triggered by a number of means, including heat, UV and visible light, redox reactions, and electrochemistry. Acrylate modified proteins can also undergo polymerization to produce functional materials, while retaining biological activity. In some cases living radical polymerizations (LRPs) may be utilized for bioconjugation. For example, the most commonly used LRPs for the formation of bioconjugates include atom-transfer radical polymerization (ATRP), reversible addition-fragmentation chain transfer (RAFT) polymerization, and nitroxide-mediated polymerization (NMP).

In some cases, photoconjugation may be utilized for bioconjugation. In some cases, polymerization may be initiated by the production of a radical species, which then propagates through bond formation to create an active polymer chain. The initiation step can be induced via a number of stimuli, with thermal decomposition, redox activation, and electrochemical ionization of an initiating species being among the most common. Alternatively, many initiators can be activated via light-induced photolytic bond breakage (type I) or photoactivated abstraction of protons from a co-initiator (type II). Photoinitiation offers the benefits of being applicable across a wide temperature range, using narrow and tunable activation wavelengths dependent on the initiator used, rapidly generating radicals, and the ability to control polymerization by removing the light source. Importantly, the tolerance of polymerizations to oxygen may be greatly enhanced, enabling polymerization in the presence of cells and tissues. The incorporation of acrylate-functionalized peptides and proteins during photopolymerization may be used as a method for producing biomaterial conjugates. Alternatively, the photoinitiated attachment of polypeptides to pendant vinyl groups on preformed materials has also been widely reported and more recently used for 3D patterning via two-photon excitation. A wide range of photoinitiators may be used in photoconjugation conjugations. For example, but not limited to, Eosin Y, 2,2-dimethoxy-2-phenyl-acetophenone, Igracure D2959, lithium phenyl-2,4,6-trimethylbenzoylphosphinate, and riboflavin may be used as photoinitiators. Photoinitiators generally absorb light to initiate the photoreaction processes. In some cases, photoconjugation may utilize a photo thiol-ene reaction. Thiols can also react with alkenes via a free-radical mechanism. A thiol radical first reacts with an alkene to generate a carbon-centered radical, which can then abstract a proton from another thiol and thus propagate the reaction. Photo thiol-ene reactions may be accelerated by electron-rich alkenes, which generate unstable carbon-radical intermediates able to rapidly abstract thiol-hydrogens. Exceptions to this rule are norbornene derivatives, in which reactivity may be driven instead by the release of ring strain upon thiol addition. This leads to a general trend in reactivity of norbornene>vinyl ether>propenyl>allyl ether>acrylate>maleimide. Norbornenes and allyloxycarbonyls (alloc groups) have been particularly widely used for peptide/protein-biomaterial functionalization, due to the almost negligible contribution of chain transfer and their ease of introduction during peptide synthesis, respectively. For example, an alloc group, typically used as an orthogonal lysine protecting group during solid-phase peptide synthesis, may be an efficient photo thiol-ene reactive handle. In other examples, norbornene photo thiol-ene reactions may be used for the tethering and spatial patterning of bioactive peptides and growth factor proteins. In addition to the most commonly used alloc and norbornene reactive groups, other alkenes have also been used for biomaterial functionalization. For example, codon reassignment has been used to site-specifically incorporate allyl-cysteine residues into proteins, which can subsequently undergo conjugation through the use of photo thiol-ene reactions. Alternatively, acrylates can undergo mixed-mode photopolymerizations in the presence of cysteine capped peptides, while allyl disulfide structures have recently been shown to undergo reversible and controlled exchange of conjugated thiols.

In some cases, aryl azide or halogenate aryl azides of a biomolecule or solid support may be utilized for bioconjugation.

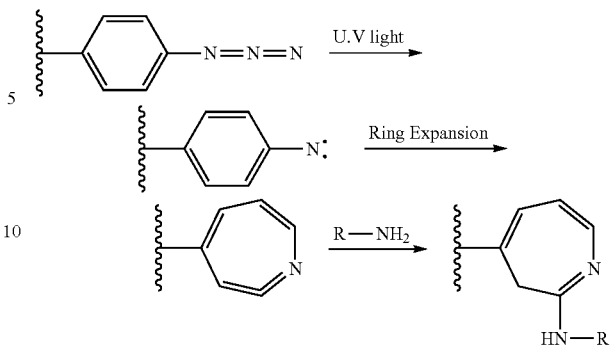

In some cases, photoreactive group benzophenone may be utilized for bioconjugation.

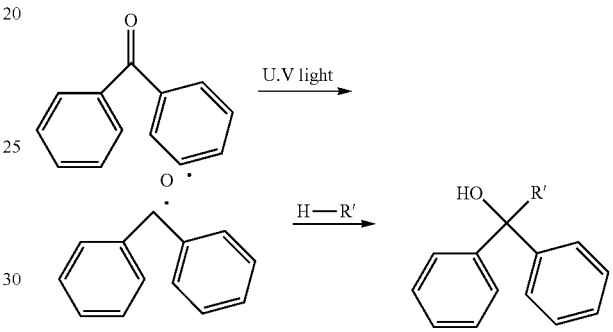

In some cases, photoreactive group anthraquinone may be utilized for bioconjugation.

In some cases, photo thiol-yne reactions may be utilized for bioconjugation. Most examples of photo thiol-yne reactions have exploited simple propargyl-ether or -amine reactive handles.

In some cases, photocaging and activation of reactive functionalities may be utilized for bioconjugation. Generally, a transient reactive species may be formed whether it be an acrylate or thiol derived radical. In some cases, photocaging may be used to mask or protect a functional group until it may be desirable for it to be exposed. In some cases, the most widely utilized cages are based around o-nitrobenzyl and coumarin chromophores. For example, nitrobenzyl-capped cysteine residues may be decaged by irradiation with 325 nm UV light, the released thiol may then react with maleimide-functionalized peptides via Michael addition, to generate a patterned hydrogel able to guide cell migration. In some cases, 6-bromo-hydroxycoumarins may be used for thiol-caging. In some cases, photoaffinitiy probes may be utilized for bioconjugation where a highly reactive intermediate upon irradiation, which then reacts rapidly with the nearest accessible functional group with high spatial precision. In some cases, the most commonly used are phenylazides, benzophenones, and phenyl-diazirines. In some cases, photocaged cycloadditions may be used. For example, the UV irradiation of tetrazoles has been shown to generate a reactive nitrile-imine intermediate which can undergo rapid cycloaddition with electron-deficient alkenes such as acrylates or acrylamides. In some cases, the nitrile-imine side-reactivity with thiols may be utilized for site-specifically conjugate cysteine containing proteins to tetrazole functionalized surfaces.

In some cases, noncovalent interactions may be utilized for bioconjugation. In some cases, noncovalent binding plays a vital role in cells, controlling biomolecular interfaces and influencing protein-protein interactions, DNA-DNA complexation, DNA-protein interfaces, protein localization, and more. In some cases, noncovalent sequences which display a binding affinity for the biomolecule of interest, allow for postfabrication modification or for native biomolecules to be simply sequestered from the surroundings within biological samples. The most commonly used binding sequences are short peptides between 7 and 20 amino acids in length, derived from a variety of sources, including known protein binding domains present in vivo or determined through techniques such as phage display. In some cases, short oligonucleotides known as aptamers can also be used to bind a variety of protein substrates, including the cytokines vascular endothelial growth factor (VEGF) and platelet derived growth factor (PDGF), as well as cell surface proteins such as epidermal growth factor receptor (EGFR). In some cases, binding sequences can also be introduced into a biomaterial with affinity for native biopolymers, such as heparin. In some cases, by first inducing biopolymer binding, the adsorption of an added or endogenous growth factor or signaling protein to a biomaterial scaffold can then be controlled. In some cases, binding affinity at the amino acid level can also be exploited to enable peptide and protein conjugation to certain biomaterial substrates. For example, the binding of unnatural catechol-based amino acids can be used to induce binding to metal oxide containing bioglasses and metallic implants, enabling the bioactivity of these important technologies to be enhanced.

In some cases, self-assembling peptides may be utilized for bioconjugation. For example, native peptides and proteins adopt a series of secondary structures, including β-sheets and α-helices, which can both stabilize individual sequences and control interprotein aggregation. In some cases, self-assembling peptides have been used extensively to assemble hydrogels and fibrous materials. In many of these structures, biological epitopes or functional groups can be appended to some or all of the peptide building blocks during peptide synthesis, to add the desired bioactivity into the system. Peptide-ligands ranging from simple adhesion motifs, to laminin derived epitopes, and growth factor mimetics have all been displayed on the surface of self-assembled fibrils. Alternatively, glycopeptides can be assembled in order to recruit extracellular signaling proteins and growth factors, mimic glycosylation patterns within hyaluronic acid, or investigate optimal sulfonation ratios in glycosaminoglycan scaffolds. In some cases, self-assembling domains can also be added to full-length proteins, leading to the incorporation of pendant functionality during hydrogel formation. In some cases, the propensity of peptides to form secondary structures has also been exploited within nonself-assembling scaffolds. This may be achieved by mixing a self-assembling peptide into a covalent hydrogel, composed of either a noninteracting polymer such as interpenetrating networks of PEG or systems where additional charge interactions further stabilize the final construct, for example between positively charged peptides and negatively charged alginate gels. As an alternative, pendant helical groups can be attached to a covalent material and used to drive the noncovalent attachment of bioactive groups such as growth factors via self-assembly into coiled-coil triple helices.

In some cases, host-guest chemistry may be utilized for bioconjugation. For example, the adhesive properties of a β-cyclodextrin modified alginate scaffold could be controlled in situ through the addition of a guest naphthyl-functionalized RGDS peptide and by subsequently introducing a non-cell adhesive adamantane-RGES peptide with a higher host binding constant, dynamic modulation of fibroblast cell attachment was enabled. Host-guest interactions between cyclodextrin and naphthyl- or adamantane-functionalized peptides allow alginate functionalization, this may be applied to other appropriate biomolecules.

In some cases, biotin-(strept)avidin may be utilized for bioconjugation. For example, avidin and streptavidin are homotetrameric proteins that can simultaneously bind up to four molecules of their small molecule binding partner biotin. The small size of biotin (with a mass of just 244 Da) and the ease with which it can be functionalized via its free carboxylic acid has led to biotin-(strept)avidin binding finding widespread use as a means to undertake biomaterial conjugation. Streptavidin-protein fusions can be produced recombinantly and bound to suitably functionalized surfaces to achieve conjugation. In some cases, biomolecule biotinylation may be undertaken, and this construct may be then bound to a (strept)avidin functionalized surface. In some cases, this can either be achieved by a direct route, via chemical preconjugation of the material with (strept)-avidin, or by exploiting the tetrameric binding of (strept)avidin to mediate indirect modification or cross-linking of biotin-functionalized scaffolds.

In some cases, nucleic acids may be utilized for bioconjugation. In some cases, in an analogous fashion to self-assembling peptides, nucleic acids can also form assembled materials themselves, to generate tunable platforms for the display of biomolecules. In some cases, DNA-tagged peptides and growth factors can be conjugated to a suitably functionalized biomaterial and used to elicit a desired biological effect on a localized cell population.

Generally, incorporating reactive handles may be utilized for bioconjugation. For example, introducing uniquely reactive motifs into biomolecule substrates provides a chemical "tag" which allows single-site selectivity or specificity to be achieved. In some cases, short peptides and oligonucleotides can typically be produced via solid phase synthesis (SPS). The versatility of organic synthesis allows difficulties in reactive handle incorporation to be overcome, with a wide range of suitably functionalized amino acids and oligonucleotides available as described herein. In some cases, an alternative approach may be to introduce unnatural amino acids (UAAs) bearing the desired reactive handles. This may be achieved via the modification of lysine residues with amine-reactive derivatives. In some cases, the use of auxotrophic bacterial strains, which are unable to biosynthesise a particular amino acid and thus require uptake from the growth media, by starving the bacteria of the native amino acid and supplementing it with a structurally related unnatural analogue, the bacterial cells can will incorporate the UAA during translation. This technique may be used to install azide- and alkyne-based mimics of methionine, leading to the introduction of reactive handles for undertaking CuAAC and SPAAC reactions. Analogous strategies can be used for the incorporation of unnatural monosaccharides, enabling the remodelling of complex glycans. In some cases, the use of codon reassignment using orthogonal tRNA and tRNA synthetase pairs that selectively recognize and charge an UAA during translation. In some cases, this may be achieved by reassigning the amber stop-codon, UAG, by incorporating a $tRNA_{CUA}$/tRNA synthetase pair from an alternative kingdom into the host cell. This pair may be able to install the desired UAA, while being effectively invisible to the endogenous cell machinery. As a result, site-directed mutagenesis can be used to introduce a single TAG codon at the desired position of the coding DNA, leading to the singular introduction of the UAA with high specificity and selectivity.

In some cases, one or more functional groups may release a reporter when reacted with another functional group, or with a SNAP or biological entity, chemical, or physical entity. Having a reporter released when the SNAP and biological, chemical, or physical entity are conjugated may allow tracking of the reaction. In some cases, it may be possible to monitor the degree of completion of a SNAP-biological/chemical entity conjugation reaction by monitoring the concentration of free reporter. In some cases, the reporter may fluoresce once released by the conjugation reaction.

In some cases, the biological, chemical, or physical entity may be functionalized with a linker. In some cases, functionalizing the biological, chemical, or physical entity with a linker may decrease steric hindrance. A linker may comprise a rigid or semi-rigid moiety which can hold the biological, chemical, or physical entity away from the SNAP. In some cases, the linker may be a long, moderate or short linker. In some cases, the linker may comprise one or more component selected from PEG, DNA, short carboxyl, carbon chain, peptoid, spacer, and/or glycer, among other examples.

In some cases, the SNAPs, seeds, and/or biological, chemical, or physical entities may be functionalized using single pot proteomics methods. Single pot proteomics methods may result in very high efficiency of functionalization. In some cases, single pot proteomics methods may be useful to functionalize biological, chemical, or physical entities with very low levels of loss of the entities.

In some embodiments, a SNAP may be a polymer which may be grown from the seed. For example if the seed is a DNA oligonucleotide then the SNAP may be a DNA molecule. In some cases, the SNAP may be a DNA molecule with regions of internal complementarity such that the molecule may self-hybridize. For example, the SNAP may be a DNA cluster, formed by self hybridization within the molecule. In some cases, the SNAP may be formed from DNA, RNA, L-DNA, L-RNA, LNA, PNA, or a mixture of two or more different types of nucleic acid. In some cases, the SNAP may have a repeating structure, such as a repeating sequence of nucleotides. In some cases, the SNAP may be an irregular polymer without a repeating sequence. For example, the SNAP may comprise a random sequence of nucleotides.

In some cases, a SNAP may be formed by rolling circle amplification. A plasmid, or other circular nucleic acid molecule, may be provided as a template, together with a primer that binds to the circular nucleic acid molecule, wherein said primer comprises a functional group on the 5' end. Performing a polymerase chain reaction (PCR) with a sufficiently long extension step, or merely a polymerase extension reaction, will allow the functionalized primer to bind the circular nucleic acid molecule and produce a single stranded nucleic acid product. The length of the single stranded nucleic acid product may be influenced by altering the extension time, the polymerase enzyme used, or the reaction conditions. In some cases, the circular nucleic acid template contains regions of internal complementarity, such that the single stranded nucleic acid product will contain regions which may self-hybridize. In some cases, the circular nucleic acid template may be a dsDNA molecule. In some cases, the single stranded nucleic acid product may be an ssDNA molecule. In some cases, the polymerase used may be a DNA polymerase.

In some cases, a SNAP may be formed by nucleic acid origami, or DNA origami. DNA origami generally refers to the nanoscale folding of DNA to create non-arbitrary two- and three-dimensional shapes at the nanoscale. The specificity of the interactions between complementary base pairs can make DNA a useful construction material. In some cases, the interactions between different regions may be controlled through design of the base sequences. DNA origami may be used to create scaffolds that hold other molecules in place or to create structures all on its own.

SNAPs as described herein can include those created via nucleic acid origami. Commonly, nucleic acid origami can refer to DNA origami, but it can also refer to RNA origami, origami of a combination of DNA and RNA molecules, or origami of nucleic acid molecules which can be other than DNA or RNA, such as a silicon-based nucleic acid, among other examples. Nucleic acid origami can result in a nucleic acid molecule which has an engineered shape. The engineered shape can be a shape which has been partially or fully planned. The planning of the shape can comprise planning or engineering what sections of nucleic acid bind, where a segment of nucleic acid can fold, where a segment of nucleic acid can be single stranded, where a segment of nucleic acid can be double stranded, where a segment of nucleic acid can be bound to a segment of nucleic acid of the same strand, or where a segment of nucleic acid can be bound to a segment of nucleic acid on another strand. In some cases, non-nucleic acid molecules, such as protein, can be used to encourage nucleic acid into the engineered shape.

Generally, nucleic acid origami can comprise at least one or more long nucleic acid strand and one or more short nucleic acid strands. Commonly, these nucleic acid strands are single stranded, although they can have segments which can be double stranded. One of the short strands can comprise at least a first segment which can be complementary to a first segment of the long strand, as well as a second segment which can be complementary to a second segment of the long strand. When the short and long strands are incubated under conditions that can allow hybridization of nucleotides, the shorter oligonucleotide can hybridize with the longer oligonucleotide. This hybridization can give shape to the nucleic acid molecule. For example, if the two segments on the first strand are separated, then these two segments can be brought together during hybridization to create a shape. In some cases, a short strand can bind to at least 2, 3, 4, 5, or 6 segments which can bind to at least 2, 3, 4, 5, or 6 complementary segments of the long nucleic acid strand.

In some cases, a short strand can have one or more segments which can be not complementary to the long strand. In such a case, the segment which may be not complementary to the long strand can be at least about 1, 2, 3, 4, 5, 10, 15, or 20 nucleotides long.

This process can be performed with at least about 1, 2, 3, 4, 5, 6, 7, 8, 9, 10, 15, 20, 30, 40, 50, 60, 70, 80, 90, 100, 150, 200, 250, 300, or more short nucleic acid strands. These short nucleic acid strands can each bind to one or more different segments of the long nucleic acid strand. Each short nucleic acid strand which hybridizes to the long nucleic acid strand can lead to a fold in the long nucleic acid strand. In some cases, the number of short strands can be correlated with the complexity of the engineered shape. For example, an engineered shape with many folds can utilize more short nucleic acid strands than an engineered shape with few folds. An engineered shape can have at least about 1, 2, 3, 4, 5, 6, 7, 8, 9, 10, 15, 20, 30, 40, 50, 60, 70, 80, 90, 100, 150, 200, 250, 300, or more folds.

In some cases, more than one long strand can be incorporated into the nucleic acid origami structure. This can be done for example to increase the complexity of the engineered shape, to ease the designing or planning of the engineered shape, to avoid the creating of a shape which may be more thermodynamically stable than the desired engineered shape, to make the creation of the engineered shape easier, or to manage costs of creating the engineered shape.

Incorporation of more than one long strand can be accomplished by designing the 2 or more long strands such that each strand has at least one segment that can be complimentary to a segment of the other strand, or by designing the 2 or more long strands such that each has at least one segment which can be complementary to a region of a short nucleic acid strand, such that both long strands have segments complementary to the short nucleic acid strand.

Short nucleic acid strands can have complementarity to one long nucleic acid strand or more than one long nucleic acid strand. In some cases, a short nucleic acid strand can also have complementarity to one or more short nucleic acid strands.

The terms "long" and "short" herein are meant to be general terms. A long strand can be longer than a short strand, although in some instances a long strand can be the same size as a short strand. In some cases, a long strand can be at least about 30, 40, 50, 100, 150, 200, 250, 300, 400, 500, 600, 700, 800, 900, 1000, or more nucleotides long. In some cases, a short strand can be at least about 6, 7, 8, 9, 10, 15, 20, 25, 30, 35, 40, 45, 50, 60, 70, 80, 90, 100, or more nucleotides long.

An engineered shape can be designed for a specific purpose. For example, an engineered shape can be designed to support a load, encapsulate a molecule, bind a molecule, connect two or more molecules, fit into a cavity, bind a protuberance, or other purpose. An engineered shape can any shape, such as oblong, rectangular, round, circular, spherical, flat, textured, smooth, symmetrical, asymmetrical, conical, or irregular. An engineered shape can be a cube, pyramid, box, cage, ladder, or tree.

An engineered shape or SNAP formed via nucleic acid origami as described above can be assembled. Assembly can refer to the process by which the nucleic acid strands hybridize to each other to create the engineered shape.

An engineered shape or SNAP can be spontaneously self-assembling. Self-assembly can occur when long and short oligonucleotides having regions which can be complimentary are incubated together. During spontaneous self-assembly, the nucleotides can hybridize and the engineered shape can be created during incubation without the help of a helper molecule or catalyst. Such self-assembling can occur under specific conditions or a range of specific conditions. Conditions which can be considered when incubating DNA strands for self-assembly can be salt concentration, temperature, and time.

Sometimes, assembly can utilize or require a catalyst. In such cases, the catalyst can speed up assembly or ensure the assembly results in a particular desired engineered shape. A catalyst can comprise RNA, DNA, or protein components.

The salt concentration during assembly can be less than 1 M, less than 0.5M, less than 0.25 M, less than 0.1M, less than 0.05 M, less than 0.01 M, less than 0.005 M, or less than 0.001 M.

The temperature during assembly can be at least room temperature. In some cases, the temperature during assembly can be at least about 50, 60, 70, 80, 85, 90, or 95° C. In some cases, the temperature during assembly can vary. For instance, the temperature can be increased to at least about 20, 30, 40, 50, 60, 70, 80, 85, 90, or 95° C. This increase can ensure the nucleic acid strands do not comprise a secondary structure prior to assembly. Once the temperature is increased as described, it can be decreased, for example to about 20, 30, 40, 50, 60, 70, or 80° C. This decrease in temperature can allow the nucleic acids to hybridize. In some cases, the decrease in temperature can occur over about 0.5, 1, 2, 3, 4, 5, 10, 15, 20, 25, 30, 45, or 60 minutes.

Assembly can be performed stepwise. In such cases, a subset of the nucleic acid molecules can be incubated together first. After these molecules are allowed to hybridize, one or more additional nucleic acid molecules can be added and allowed to hybridize. In some cases, two or more engineered shapes which have been assembled can be incubated together for assembly into a larger engineered shape.

In some cases, assembly can comprise fractal assembly. Fractal assembly can create a SNAP which can be an array of engineered shapes. Assembly can occur in stages, which can simplify the design process or ensure correct assembly. Such an array can be assembled in at least 1, 2, 3, 4, 5, 10, 15, 20, 30, 40, 50, 60, 70, 80, 90, 100, 200, 300, 400, 500, 1000, or more stages. In some cases, the number of stages used can correlate with a reduction of spurious interactions. This can be due to a reduction in the total number of possible reactions at any given time.

SNAPs can be assembled into an array which can be at least 3×3, at least 5×5, at least 10×10, at least 50×50, at least 100×100, or at least 1000×1000 (engineered shapes×engineered shapes).

Each hybridization reaction can take about 10, 20, 30, 40, 50, or 60 seconds. In some cases, each hybridization reaction can take about 1, 2, 3, 4, 5, 10, 15, 20, 30, 40, 50, or 60 minutes. In some cases, a hybridization reaction can take more than 1 hour.

Nucleic acid origami may be used to preferentially choose how the SNAP will "land" on the solid support. For example, nucleic acid origami may be used to construct a SNAP with a landing surface that can preferentially contact the solid support, A SNAP such as one made via nucleic acid origami can be designed to comprise a region that can create steric or electrostatic interactions with the support that can influence the orientation of the SNAP on the support. For example, the region can comprise nucleotides having modifications e.g. to the backbone of the nucleic acid which can promote interaction between the SNAP and the solid support. In further examples, the region can comprise protuberances or cavities which can "fit" to cavities or protuberances on the solid support. In some cases, the support surface can comprise chemical structuring (e.g. nanoparticles or oligonucleotides), click reagents, or other rationally designed materials that can influence the position and orientation of SNAP structures, including SNAPs synthesized via nucleic acid origami.

Nucleic acid origami can be used to construct a SNAP with a linker which can attach a biological, chemical, or physical entity, wherein said linker may be positioned relative to the landing surface such that the biological, chemical, or physical entity can be distal or approximately distal to the solid support. The linker may also comprise a region of dsDNA to force a rigid outpost from the SNAP. In some cases, protein origami may also be used.

A surface can have properties such that a SNAP can bind to the surface in such a way that it can flop or lean. The SNAP can flop or lean to the left, to the right, to the front, to the back, or to any combination of sides thereof. The SNAP can flop or lean once and remain in place, or itcan flop freely between sides over time. In some cases, the SNAP can preferentially flop in one direction over one or more other directions. In some cases, the SNAP can preferentially avoid flopping in a particular direction.

In some cases, for example, filamentous or stranded molecules, such as nanoparticles or oligonucleotide strands, can be attached to a surface. A SNAP, which can comprise an engineered shape, can comprise one or more moieties which can bind to a filamentous or stranded molecule, such as a dangling single stranded oligonucleotide or nanoparticle. Upon contacting the surface with such SNAPs, the one or more moieties can interact with one or more of the filamentous or stranded molecules. In some cases, the moieties can bind tightly to the filamentous or stranded molecules. The SNAPs can be removable or non-removable in such cases.

Computational modeling or simulation tools may be employed to design and optimize oligonucleotide or protein sequences to create particular SNAP structures.

In some cases, a SNAP may be a nucleic acid plasmid, such as a DNA plasmid. Plasmids may exist in a compact form known as supercoiled DNA. The radii of a supercoiled plasmid may be determined by the plasmid size—i.e. a plasmid with a longer backbone will form a larger supercoiled entity. In some cases, a SNAP may comprise a plasmid with a backbone of between 5 kb and 150 kb. In some cases, a SNAP may comprise a plasmid with a backbone of between 5 kb and 100 kb. In some cases, a SNAP may comprise a plasmid with a backbone of between 5 kb and 90 kb. In some cases, a SNAP may comprise a plasmid with a backbone of between 25 kb and 50 kb. In some cases, a SNAP may comprise a plasmid with a backbone of at least about 5 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 105 kb, 110 kb, 115 kb, 120 kb, 125 kb, 130 kb, 135 kb, 140 kb, 145 kb, or 150 kb. In some embodiments, SNAPs may be imaged using an imaging platform, such as Nanocyte or Leica In some cases, a SNAP may have a branched structure. For example the SNAP may be a dendrimer. Some examples of dendrimers may be found in Newkome, George R., and Carol D. Shreiner. "Poly(amidoamine), polypropylenimine, and related dendrimers and dendrons possessing different 1→2 branching motifs: an overview of the divergent procedures." Polymer 49.1 (2008): 1-173. A dendrimer used with the methods of this disclosure may be a G1, G2, G3, G4, G5, G6, G7, G8, G9, G10, G11, G12, G13, G14, or G15 dendrimer. In some cases, the dendrimer may be higher than a G15 dendrimer, for example dendrimer between G15 and G30.

In some embodiments, the SNAP may be a protein, or comprised of proteins. For example the SNAP may be a protein fibril. The SNAP may be comprised of proteins known to form into fibrils, such as, for example, the tau protein, or portions of the tau protein. A 31 residue portion of tau which assembles into fibrils is described in Stöhr, Jan, et al. "A 31-residue peptide induces aggregation of tau's microtubule-binding region in cells." Nature chemistry 9.9 (2017): 874. In some cases, the SNAP may comprise tetratricopeptide repeats. Examples of tetratricopeptide repeats may be found in Blatch, Gregory L., and Michael Lassie. "The tetratricopeptide repeat: a structural motif mediating protein-protein interactions." Bioessays 21.11 (1999): 932-939. Other examples of proteins which may assemble may be found in Speltz, Elizabeth B., Aparna Nathan, and Lynne Regan. "Design of protein-peptide interaction modules for assembling supramolecular structures in vivo and in vitro." ACS chemical biology 10.9 (2015): 2108-2115.

In some embodiments, the SNAP may be a single molecule. In some embodiments the SNAP may not be a single molecule. In some cases, the SNAP may be assembled from several molecules which bind non-covalently. For example, the SNAP may be formed from two or more nucleic acid molecules which hybridize together. In another example the SNAP may be formed from two or more protein molecules which assemble together via non-covalent bonds.

In some embodiments, the SNAPs are between about 50 nm and about 100 um in diameter.

The SNAPs are generally polymeric molecules. These may be grown through a controlled polymerization reaction, a stepwise polymerization reaction, or a step by step synthesis method. The growth of the SNAPs may be controlled by the amount of monomers available, the length of time the reaction may be allowed to proceed, or the number of synthesis steps performed.

Each SNAP may have a diameter of at least about 10 nanometers (nm), or about 10 nm, about 50 nm, about 75 nm, about 100 nm, about 125 nm, about 150 nm, about 175 nm, about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, about 700 nm, about 725 nm, about 750 nm, about 775 nm, about 800 nm, about 825 nm, about 850 nm, about 875 nm, about 900 nm, about 925 nm, about 950 nm, about 975 nm, about 1000 nm, about 1025 nm, about 1050 nm, about 1075 nm, about 1100 nm, about 1125 nm, about 1150 nm, about 1175 nm, about 1200 nm, about 1225 nm, about 1250 nm, about 1275 nm, about 1300 nm, about 1325 nm, about 1350 nm, about 1375 nm, about 1400 nm, about 1425 nm, about 1450 nm, about 1475 nm, about 1500 nm, about 1525 nm, about 1550 nm, about 1575 nm, about 1600 nm, about 1625 nm, about 1650 nm, about 1675 nm, about 1700 nm, about 1725 nm, about 1750 nm, about 1775 nm, about 1800 nm, about 1825 nm, about 1850 nm, about 1875 nm, about 1900 nm, about 1925 nm, about 1950 nm, about 1975 nm, about 2000 nm, about 3000 nm, about 4000 nm, about 5000 nm, about 6000 nm, about 7000 nm, about 8000 nm, about 9000 nm, about 10 µm, about 15 µm, about 20 µm, about 25 µm, about 30 µm, about 40 µm, about 50 µm, about 75 µm, about 100 µm, about 200 µm, about 300 µm, about 400 µm, about 500 µm, or more than about 500 µm. In some cases, the SNAP may have a diameter between about 100 nm and 500 nm, between about 200 nm and about 400 nm, between about 500 nm and about 10 µm, or between about 1000 nm and about 10 µm.

In some cases the SNAPs may be covalently attached to the solid support using a click chemistry. Generally, the term "click chemistry" is used to describe reactions that are high yielding, wide in scope, create only byproducts that can be removed without chromatography, are stereospecific, simple to perform, and can be conducted in easily removable or benign solvents (McKay, C., & Finn M. G. (2014) Click Chemistry in Complex Mixtures Bioorthogonal Bioconjugation vol 21, Issue 9, pp 1075-1101; M. G. Meldal, M., & Tornøoe, C. W. (2008). Cu-Catalyzed Azide-Alkyne Cycloaddition. Chemical Reviews, 108(8), 2952-3015; Lutz, J., & Zarafshani, Z. (2008). Efficient construction of therapeutics, bioconjugates, biomaterials and bioactive surfaces using azide-alkyne "click" chemistry. Advanced Drug Delivery Reviews, 60(9), 958-970, herein incorporated by reference).

In some cases, the click chemistry reaction may be a CuAAC, SPAAC, SPANC, or as described elsewhere herein. In some cases, the click chemistry reaction may need a copper source such as, for example, $CuSO_4$, Cu(O), CuBr $(Ph_3P)_3$, CuBr, CuBr/Cu(OAc)$_2$, CuBr$_2$, [Cu(CH3CN)4] PF6, PS—NMe2:CuI, silica: CuI, (EtO)3P:CuI, CuCl/Pd2 (dba)3, CuBF4, CuCl, CuCl2, Cu(AcO)2, Cu(2), TTA: CuSO4, Cu(1) zeolite (USY), Cu(CH3CN)4OTf, CuOTf, Cu(2):bis-batho, or a combination thereof. In some cases a copper source is not needed for the click chemistry reaction to proceed. In some cases, the reducing agent of the click chemistry reaction may be, for example, NaAsc, air, ICI, oxygen, $N_2$, HAsc, TCEP, dithithreitol (DTT), PPh$_3$, mercaptoethanol, tris(2-carboxyethyl)phosphine (TCEP), TCEPT-hydrochloric acid a combination thereof, or no reducing agent. In some cases, the solvent of the click chemistry reaction may be, for example, THF, pyridine, DMSO, DMF, toluene, NMP, acetonitrile, water, tBuOH, iBuOH, EtOH, MeOH, dioxane, dichloromethane, HEPES, NaCl buffer, acetone, PBS, SFM, Tris buffer, borate buffer, PB, TFH, AcOEt, PIPES, urea, acetone, Tris, saline, AllOCO$_2$Me, TMS-N$_3$, urea solution, bicarbonate buffer, a combination thereof, or no solution. In some cases, the base of the click chemistry reaction may be, for example, DIPEA, Lut Na2CO3, iPr$_2$NH, DBU, Et$_3$N, Et$_3$N·HCl, Et$_3$NH+—OAc, K$_2$CO$_3$, TBAF, CuSO$_4$, PS—NMe$_2$, piperidine, a desired pH, or a combination thereof. In some cases, the ligand of the click chemistry reaction may be, for example, TBTA, proline, BMAH, Lut, chiral Lig's, pyridine, His, Batho, TTA, Bim, Phen, Bipy, PMDETA, dNbipy, TRMEDA, or a combination thereof. In some cases, the temperature of the click chemistry reaction may be, for example, 0-5° C., 5-15° C., 15-25° C., 20-25° C., 25-35° C., 35-45° C., 45-55° C., 55-65° C., 65-75° C., 75-85° C., 85-95° C., or greater. In some cases, the temperature of the click chemistry reaction may be less than 0° C. In some reactions, the click chemistry reaction may be covered by aluminum foil. In some cases, the click chemistry reaction may include an acid, for example, trifluoroacetic acid, trichloroacetic acid, or tribromoacetic acid.

In some cases, a crosslinker may be used for conjugation. In some cases, the crosslinker may be a zero-length crosslinker, homobifunctional crosslinker, heterobifunctional crosslinker, or a trifunctional cross linker. Crosslinkers may be incorporated into a biomolecule preformed or in-situ.

In some cases, zero-length crosslinkers mediate the conjugation for bioconjugation by forming a bond containing no additional atoms. Thus, one atom of a molecule may be covalently attached to an atom of a second molecule with no intervening linker or spacer. In so conjugation schemes, the final complex may be bound together by virtue of chemical components that add foreign structures to the substances being crosslinked. Carbodiimides may be used to mediate the formation of amide linkages between carboxylates and amines or phosphoramidate linkages between phosphates and amines and are popular type of zero-length crosslinker that may be used, being efficient in forming conjugates between two protein molecules, between a peptide and a protein, between an oligonucleotide and a protein, between a biomolecule and a surface or particle, or any combination of these with small molecules. In some cases, EDC (or EDAC; 1-ethyl-3-(3-dimethylaminopropyl) carbodiimide hydrochloride) may be used for conjugating biomolecules containing carboxylates and amines. In some cases, CMC, or 1-cyclohexyl-3-(2-morpholinoethyl) carbodiimide (usually synthesized as the methop-toluene sulfonate salt), may be a water-soluble reagent used to form amide bonds between one molecule containing a carboxylate and a second molecule containing an amine that may be used as a crosslinker for bioconjugation. In some cases, DIC, or diisopropyl carbodiimide may be used for bioconjugation as a zero-length crosslinker. In some cases, DCC (dicyclohexyl carbodiimide) may be used for bioconjugation as a zero-length crosslinker. In some cases, Woodward's reagent K is N-ethyl-3-phenylisoxazolium-3'-sulfonate, a zero-length crosslinking agent able to cause the condensation of carboxylates and amines to form amide bonds. In some cases, CDI, or N,N'-carbonyl diimidazole may be used for bioconjugation as a zero-length crosslinker. In some cases, Schiff base formation and reductive amination may be used for bioconjugation as a zero-length cross linker.

In some cases, homobifunctional crosslinkers mediate the conjugation for bioconjugation. In some cases, homofictuional NHS esters may be used for bioconjugation. For example, Lomant's reagent [(dithiobis(succinimidylpropionate), or DSP]) is a homobifunctional NHS ester crosslinking agent containing an eight-atom spacer 12 Å in length. The sulfo-NHS version of DSP, dithiobis(sulfosuccin-imidylpropionate) or DTSSP, is a water-soluble analog of Lomant's reagent that can be added directly to aqueous reactions without prior organic solvent dissolution. In some cases, disuccinimidyl suberate (DSS), an amine-reactive, homobifunctional, NHS ester, crosslinking reagent produces an eight-atom bridge (11.4 Å) between conjugated biomolecules. In some cases, disuccinimidyl tartarate (DST), a homobifunctional NHS ester crosslinking reagent that contains a central diol that is susceptible to cleavage with sodium periodate may be used forms amide linkages with α-amines and ε-amines of proteins or other amine-containing molecules. In some cases, BSOCOES [bis[2-(succinimidyloxycarbonyloxy)ethyl] sulfone], a water-insoluble, homobifunctional NHS ester crosslinking reagent that contains a central sulfone group, where the two NHS ester ends are reactive with amine groups in proteins and other molecules to form stable amide linkages. In some cases, ethylene glycolbis(succinimidylsuccinate) (EGS), a homobifunctional crosslinking agent that contains NHS ester groups on both ends. The two NHS esters are amine reactive, forming stable amide bonds between cross-linked molecules within a pH range of about 7 to 9. In some cases, disuccinimidyl glutarate (DSG), a water-insoluble, homobifunctional crosslinker containing amine-reactive NHS esters at both ends, may be used for biconjugation. In some cases, N,N'-Disuccinimidyl carbonate (DSC), the smallest homobifunctional NHS ester crosslinking reagent available may be used. In some cases, Dimethyl adipimidate (DMA), Dimethyl pimelimidate (DMP), Dimethyl suberimidate (DMS), dimethyl 3,3'-dithiobispropionimidate (DTBP), 1,4-di-[3'-(2'-pyridyldithio)propionamido] butane, bismaleimidohexane, 1,5-difluoro-2,4-dinitrobenzene or 1,3-difluoro-4,6-dinitrobenzene, DFDNPS (4,4'-difluoro-3,3'-dinitrophenylsulfone), Bis-[β-(4-azidosalicylamido)ethyl]disulfide (BASED), formaldehyde, Glutaraldehyde, 1,4-butanediol diglycidyl ether, adipic dihydrazide, carbohydrazide, 3,3'-dimethylbenzidine,p-diaminodiphenyl, or haloacetyl derivatives may be used as homobifunctional crosslinkers.

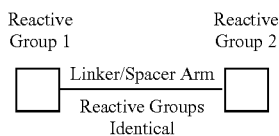

In some cases, heterobifunctional crosslinkers mediate the conjugation for bioconjugation. Heterobifunctional reagents can be used to crosslink proteins and other molecules in a two- or three-step process. In some cases, one protein may be modified with a heterobifunctional compound using the crosslinker's most reactive or most labile end. The modified protein may then be purified from excess reagent by gel filtration or rapid dialysis. In some cases, heterobifunctionals contain at least one reactive group that displays extended stability in aqueous environments, therefore allowing purification of an activated intermediate before adding the second molecule to be conjugated. For instance, an N-hydroxysuccinimide (NHS ester-maleimide hetero-bifunctional can be used to react with the amine groups of one protein through its NHS ester end (the most labile functionality), while preserving the activity of its maleimide functionality. Since the maleimide group has greater stability in aqueous solution than the NHS ester group, a maleimide-activated intermediate may be created. After a quick purification step, the maleimide end of the crosslinker can then be used to conjugate to a sulfhydryl-containing molecule. Heterobifunctional crosslinking reagents may also be used to site-direct a conjugation reaction toward particular parts of target molecules. In some cases, amines may be coupled on one molecule while sulfhydryls or carbohydrates are targeted on another molecule. In some cases, heterobifunctional reagents containing one photo-reactive end may be used to insert nonselectively into target molecules by UV irradiation. Another component of heterobifunctional reagents may be the cross-bridge or spacer that ties the two reactive ends together. Crosslinkers may be selected based not only on their reactivities, but also on the length and type of cross-bridge they possess. Some heterobifunctional families differ solely in the length of their spacer. The nature of the cross-bridge may also govern the overall hydrophilicity of the reagent. For instance, polyethylene glycol (PEG)-based cross-bridges create hydrophilic reagents that provide water solubility to the entire heterobifunctional compound. In some cases, a number of heterobifunctionals contain cleavable groups within their cross-bridges, lending greater flexibility to the experimental design. A few crosslinkers contain peculiar cross-bridge constituents that actually affect the reactivity of their functional groups. For instance, it is known that a maleimide group that has an aromatic ring immediately next to it is less stable to ring opening and loss of activity than a maleimide that has an aliphatic ring adjacent to it. In addition, conjugates destined for use in vivo may have different properties depending on the type of spacer on the associated crosslinker. Some spacers may be immunogenic and cause specific antibody production to occur against them. In other instances, the half-life of a conjugate in vivo may be altered by the choice of cross-bridge, especially when using cleavable reagents. In some cases, the heterobifunctional crosslinker may be N-succinimidyl 3-(2-pyridyldithio)propionate (SPDP), standard SPDP, LC-SPDP, sulfo-LC-SPDP, succinimidyloxycarbonyl-α-methyl-α-(2-pyridyldithio) toluene, succinimidyl-4-(N-maleimidomethyl)cyclo-hexane-1-carboxylate, sulfosuccinimidyl-4-(N-maleimidomethyl) cyclohexane-1-carboxylate, m-maleimidobenzoyl-N-hydroxysuccinimide ester, m-maleimidobenzoyl-N-hydroxysulfo-succinimide ester, N-succinimidyl(4-iodoacetyl)aminobenzoate, sulfosuccinimidyl(4-iodoacetyl)amino-benzoate, succinimidyl-4-(p-maleimidophenyl)butyrate, N-(γ-maleimidobutyryloxy) succinimide ester, succinimidyl-3-(bromoacetamide) propionate, succinimidyl iodoacetate, 4-(4-N-maleimidophenyl)butyric acid hydrazide, 4-(N-maleimidomethyl)cyclohexane-1-carboxyl-hydrazide, 3-(2-pyridyldithio)propionyl hydrazide, N-hydroxysuccinimidyl-4-azidosalicylic acid, sulfosuccinimidyl-2-(p-azidosalicylamido) ethyl-1,3'-dithiopropionate, N-hydroxysulfosuccinimidyl-4-azido-benzoate, N-succinimidyl-6-(4'-azido-2'-nitropheny-lamino)hexanoate, sulfosuccinimidyl-6-(4'-azido-2'-nitrophenylamino)hexanoate, N-5-Azido-2-nitrobenzoyloxysuccinimide, Sulfosuccinimidyl-2-(m-azido-o-nitrobenzamido)-ethyl-1,3'-dithiopropionate, N-succinimidyl-(4-azidophenyl)1,3'-dithiopropionate, sulfosuccinimidyl 4-(p-azidophenyl) butyrate, Sulfosuccinimidyl 2-(7-azido-4-methylcoumarin-3-acetamide)ethyl-1, 3'-dithiopropionate, sulfosuccinimidyl 7-azido-4-methylcoumain-3-acetate, p-Nitrophenyl diazopyruvate, p-nitrophenyl-2-diazo-3,3,3-trifluoropropionate, 1-(p-azidosalicylamido)-4-(iodoacetamido)butane, N-[4-(p-azidosalicylamido)butyl]-3'-(2'-pyridyldithio) propionamide, Benzophenone-4-maleimide, p-azidobenzoyl hydrazide, 4-(p-azidosalicylamido)butylamine, or p-azidophenyl glyoxal.

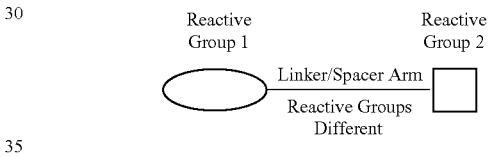

Other examples of crosslinkers, but not limited to, may be NHS-PEG$_4$-Azide, NHS-phosphine, N-γ-maleimidobutyryl-oxysulfosuccinimide ester, m-maleimidobenzoyl-N-hydroxysuccinimide ester, sulfosuccinimidyl (4-iodoacetyl)aminobenzoate, succinimidyl 3-(2-pyridyldithio)propionate), sulfosuccinimidyl (4-iodoacetyl)aminobenzoate, m-maleimidobenzoyl-N-hydroxysuccinimide ester, 1-Ethyl-3-[3-dimethylaminopropyl]carbodiimide hydrochloride, dimethyl pimelimidate, sulfosuccinimidyl 6-(3'-(2-pyridyldithio)propionamido)hexanoate, 6-(3'-[2-pyridyldithio]-propionamido)hexanoate, tris-(succinimidyl)aminotriacetate, Sulfo-NHS-LC-Diazirine, bismaleimidohexane, 1,4-bismaleimidobutane, sulfosuccinimidyl 4-(N-maleimidophenyl)butyrate, Sulfo-SBED Biotin Label Transfer Reagent, succinimidyl 6-(3(2-pyridyldithio)propionamido)hexanoate, succinimidyl 3-(2-pyridyldithio)propionate, sulfosuccinimidyl 6-(3'-(2-pyridyldithio)propionamido)hexanoate, L-Photo-Leucine, L-Photo-Methionine, sulfosuccinimidyl 4-(N-maleimidomethyl)cyclohexane-1-carboxylate, Pierce BS(PEG)5, sulfosuccinimidyl 2-((4,4'-azipentanamido)ethyl)-1,3'-dithiopropionate, Sulfo-NHS—SS-Diazirine, Pierce SM(PEG)n, NHS-dPEG-Mal, N-hydroxysulfosuccinimide, sulfosuccinimidyl 4-(N-maleimidomethyl)cyclohexane-1-carboxylate, Sulfosuccinimidyl-4-(N-maleimidomethyl)cyclohexane-1-carboxylate, 1-Ethyl-3-(3-Dimethylaminopropyl)carbodiimide Hydrochloride, N-α-maleimidoacet-oxysuccinimide ester, Sulfo-NHS-LC-Biotin, bis(sulfosuccinimidyl)suberate, trans-4-(maleimidylmethyl)cyclohexane-1-Carboxylate, bismaleimidohexane, 1,8-bismaleimido-diethyleneglycol, N-β-maleimidopropionic acid hydrazide, N-succinimidyl 3-(2- pyridyldithio)-propionate, sulfosuccinimidyl 4-(N-maleimidomethyl)cyclohexane-1-carboxylate, 3-(2-pyridyldithio) propionyl hydrazide, 4-(4-N-maleimidophenyl)butyric acid hydrazide, 3,3'-dithiobis(sulfosuccinimidyl propionate, bis (sulfosuccinimidyl) 2,2,4,4-glutarate-d4, or Succinimidyl-4-(N-maleimidomethyl)cyclohexane-1-carboxylate.

In some cases, the alkyne derivative attached to the solid support or SNAP may be, for example, dib enzocyclooctyne-amine, dibenzocyclooctyne-acid, dibenzocyclooctyne-N-hydroxysuccinimidyl ester, dibenzocyclooctyne-N-hydroxysuccinimidyl ester, dibenzocyclooctyne-sulfo-N-hydroxysuccinimidyl ester, ibenzocyclooctyne-sulfo-N-hydroxysuccinimidyl ester, Dibenzocyclooctyne-S—S—N-hydroxysuccinimidyl ester, dibenzocyclooctyne-PEG4-N-hydroxysuccinimidyl ester, dibenzocyclooctyne-PEG4-acid, dibenzocyclooctyne-maleimide, sulfo-dibenzocyclooctyne-biotin conjugate, (1R,8S,9s)-Bicyclo[6.1.0]non-4-yn-9-ylmethyl N-succinimidyl carbonate, (1R,8S,9s)-Bicyclo6.1.0non-4-yn-9-ylmethanol, APN-BCN, (1R,8S,9s)-Bicyclo6.1.0non-4-yn-9-ylmethanol, ethyl (1R,8S,9s)-bicyclo6.1.0non-4-ene-9-carboxylate, Alkyne-PEGS-acid, (R)-3-Amino-5-hexynoic acid hydrochloride, (S)-3-Amino-5-hexynoic acid hydrochloride, (R)-3-(Boc-amino)-5-hexynoic acid, (S)-3-(Boc-amino)-5-hexynoic acid, N-Boc-4-pentyne-1-amine, 4-pentyne-1-amine, Boc-propargyl-Gly-OH, 3-Ethynylaniline, 4-Ethynylaniline, PC biotin-alkyne, Propargyl chloroformate, Propargyl-N-hydroxysuccinimidyl ester, N—Z-4-pentyne-1-amine, 1-Azido-2-(2-(2-ethoxyethoxy)ethoxy)ethane, O-(2-Azido-ethyl)heptaethylene glycol, Click-iT® DIBO-Alexa Fluor® 488, Click-iT® DIBO-Alexa Fluor® 555, Click-iT® DIBO-Alexa Fluor® 594, Click-iT® DIBO-Alexa Fluor® 647, Click-iT® DIBO TAMRA, Click-iT® DIBO-biotin, Click-iT® DIBO-amine, Click-iT® DIBO-maleimide, Click-iT® DIBO-succinimidyl ester, Alexa Fluor® 488 alkyne, Alexa Fluor® 555 alkyne, triethylammonium salt, Alexa Fluor® 594 carboxamido-(5-(and 6-)propargyl), bis(triethylammonium salt, 3-propargyloxypropanoic acid, succinimidyl ester, biotin alkyne, tetraacetyl fucose alkyne, Oregon Green® 488 alkyne*6-isomer*, iodoacetamide alkyne, or 5-carboxytetramethylrhodamine propargylamine.

In some cases, the azide derivative attached to a solid support, SNAP, or biomolecule may be, for example, (S)-5-Azido-2-(Fmoc-amino)pentanoic acid, (S)-(−)-2-Azido-6-(Boc-amino)hexanoic acid (dicyclohexylammonium), (S)-2-Azido-3-(4-tert-butoxyphenyl)propionic acid cyclohexylammonium salt, L-Azidohomoalanine hydrochloride, (S)-2 Azido-3-(3-indolyl)propionic acid cyclohexylammonium salt, (S)-2-Azido-3-methylbutyric acid cyclohexylammonium salt, (S)-2-Azido-3-phenylpropionic acid (dicyclohexylammonium) salt, Boc-3-azido-Ala-OH (dicyclohexylammonium) salt, N-Boc-4-azido-L-homoalanine (dicyclohexylammonium) salt, N-Boc-6-azido-L-norleucine (dicyclohexylammonium) salt, Boc-4-azido-Phe-OH, (S)-(−)-4-tert-Butyl hydrogen 2-azidosuccinate (dicyclohexylammonium) salt, N2-[(1,1-Dimethylethoxy)carbonyl]-N6-[(2-propynyloxy)carbonyl]-L-lysine, Fmoc-β-azido-Ala-OH, 2-Acetamido-2-deoxy-β-D-glucopyranosyl azide, 2-Acetamido-2-deoxy-β-D-glucopyranosyl azide 3,4,6-triacetate, 2-Acetamido-3,4,6-tri-O-benzyl-2-deoxy-β-D-glucopyranosyl azide, N-Azidoacetylgalactosamine-tetraacylated, N-Azidoacetylglucosamine, N-Azidoacetyl-glucosamine-tetraacylated, 6-Azido-6-deoxy-1,2:3,4-di-O-isopropylidene-α-D-galactopyranose, 1-Azido-1-deoxy-β-D-galactopyranoside, 1-Azido-1-deoxy-β-D-galactopyranoside tetraacetate, 6-Azido-6-deoxy-D-galactose, 1-Azido-1-deoxy-β-D-glucopyranoside, 2-Azido-2-deoxy-D-glucose, 6-Azido-6-deoxy-D-glucose, 1-Azido-1-deoxy-β-D-lactopyranoside, 3-Azido-2,3-dideoxy-1-O-(tert-butyldimethylsilyl)-β-D-arabino-hexopyranose, 2-Azido-D-galactose tetraacetate, 1,2-Di-O-acetyl-3-azido-3-deoxy-5-O-(p-toluoyl)-D-ribofuranose, α-D-Mannopyranosyl azide tetraacetate, 2,3,4,6-Tetra-O-acetyl-1-azido-1-deoxy-α-D-galactopyranosyl cyanide, 2,3,4-Tri-O-acetyl-β-D-xylopyranosyl azide, 3'-Azido-3'-deoxythymidine, γ-(2-Azidoethyl)-ATP sodium salt solution, γ-[(6-Azidohexyl)-imido]-ATP sodium salt, (2'S)-2'-Deoxy-2'-fluoro-5-ethynyluridine, 5-Ethynyl-2'-deoxycytidine, N6-Propargyl-ATP sodium salt, 4-Acetamidobenzenesulfonyl azide, (E)-N-(2-Aminoethyl)-4-{2-[4-(3-azidopropoxy)phenyl]diazenyl}benzamide hydrochloride, Azidoacetic acid NHS ester, 1-Azidoadamantane, 4-Azidoaniline hydrochloride, (4S)-4-[(1R)-2-Azido-1-(benzyloxy)ethyl]-2,2-dimethyl-1,3-dioxolane, NHS-PEG$_4$-azide, [3aS-(3aa,4a,5(3,7aa)]-5-Azido-7-bromo-3a,4,5,7a-tetrahydro-2,2-dimethyl-1,3-benzodioxol-4-ol, 3'-Azido-3'-2-azido-1-methylquinolinium tetrafluoroborate, 5-Azidopentanoic acid, 4-Azidophenacyl bromide, 4-Azidophenyl isothiocyanate, 3-(4-Azidophenyl)propionic acid, 3-Azido-1-propanamine, 3-Azido-1-propanol, Azo biotin-azide, Biotin picolyl azide, tert-Butyl 2-(4-{[4-(3-azidopropoxy)phenyl]azo}benzamido)ethylcarbamate, 4-Carboxybenzenesulfonazide, 7-(Diethylamino)coumarin-3-carbonyl azide, Ethidium bromide monoazide, Ethyl azidoacetate, 4-Methoxybenzyloxycarbonyl azide, aryl azides, diazierines, or O-(2-Aminoethyl)-O'-(2-azidoethyl)heptaethylene glycol, bromoacetomido-PEG$_3$-azide, iodoacetamide-azide, Alexa Fluor® 488 azide, Alexa Fluor® 488 5-carboxamido-(6-azidohexanyl), bis(triethylammonium salt), Alexa Fluor® 555 azide triethylammonium salt, Alexa Fluor® 594 carboxamido-(6-azidohexanyl), bis(triethylammonium salt), Alexa Fluor® 647 azide triethylammonium salt, 3-(azidotetra(ethyleneoxy))propionic acid succinimidyl ester, biotin azide, L-azidohomoalanine, L-homopropargylglycine, Click-iT® farnesyl alcohol azide, 15-azidopentadecanoic acid, 12-azidododecanoic acid, tetraacetylated N-azidoacetylgalactosamine, tetraacetylated N-azidoacetyl-D-mannosamine, tetraacetylated N-azidoacetylglucosamine, iodoacetamide azide, or tetramethylrhodamine 5-carboxamido-(6-azidohexanyl).

In some cases, the SNAPs may be covalently attached to the solid support using an inherent chemistry of the SNAP. In some cases, the solid support may be covered with functional groups that may be reactive to the SNAP. These functional groups, for example, may be hydroxyl, carbonyl, carboxyl, amino, amides, azides, alkynes, alkenes, phosphates, sulfhydryl, thiols, isothiocyanates, isocyanates, acyl azides, NHS esters, silane, sulfonyl chlorides, aldehydes, esters, glyoxals, epoxides, oxiranes, alkanethiols, carbonates, aryl halides, imidoesters, carbodiimides, anhydrides, fluorophenyl esters, amines, thymines or a combination thereof. In some cases, the SNAP may have a functional group that may react with a functional group on the solid support to form a covalent bond. For example, a DNA SNAP may be attached to a solid support by reacting one or more thymines in the DNA with amines on the solid support. For example, the —NH$_2$ at the N-terminus of a polypeptide chain or —COOH at the C-terminus of a polypeptide chain may react with an appropriate functional group and be attached to the solid support through a covalent bond. In some cases, for example, the functional group of a SNAP may be hydroxyl, carbonyl, carboxyl, amino, amides, azides, alkynes, silane, alkenes, phosphates, sulfhydryl, thiols, isothiocyanates, isocyanates, acyl azides, NHS esters, sulfonyl chlorides, aldehydes, esters, glyoxals, epoxides, oxiranes, alkanethiols, carbonates, aryl halides, imidoesters, carbodiimides, anhydrides, fluorophenyl esters, amines, thymines or a combination thereof. Other bioconjugation processes, reactions, and functional groups are described elsewhere within that may be used to attach a SNAP to a solid support. Such a reaction could be spontaneous, or could be induced by application of heat or ultraviolet radiation.

In some cases, silane chemistry may be employed for bioconjugation. In some cases, functional silane compounds containing an organofunctional or organo-reactive arm can be used to conjugate biomolecules to inorganic substrates. The appropriate selection of the functional or reactive group for a particular application can allow the attachment of proteins, oligonucleotides, whole cells, organelles, or even tissue sections to substrates. The organosilanes used for these applications may include functional or reactive groups such as hydroxyl, amino, aldehyde, epoxy, carboxylate, thiol, and even alkyl groups to bind molecules through hydrophobic interactions. In some cases, 3-Aminopropyltriethoxysilane (APTES) and 3-Aminopropyltrimethoxysilane are used to create a functional group on an inorganic surface or particle. In some cases, once deposited on a substrate, the alkoxy groups form a covalent polymer coating with the primary amine groups sticking off the surface and available for subsequent conjugation. Carboxyl- or aldehyde-containing ligands may be directly coupled to the aminopropyl groups using a carbodiimide reaction or reductive amination. In some cases, alternatively, surfaces initially derivatized with an aminopropylsilane compound can be modified further with spacer arms or crosslinkers to create reactive groups for coupling affinity ligands or biomolecules. For instance, the amine groups may be derivatized with an NHS-PEGn-azide compound for use in click chemistry or Staudinger ligation reactions for linking proteins or other biomolecules. In some cases, APTES-modified surfaces may be further derivatized with amine-reactive crosslinkers to create additional surface characteristics and reactivity. Modification with NHS-PEG4-azide forms a hydrophilic PEG spacer terminating in an azido group that can be used in a click chemistry or Staudinger ligation reaction to couple other molecules.

In some cases, other crosslinking agents that contain an amine-reactive group on one end also may be used to modify and activate the APTES-modified substrate. Surfaces may be designed to contain, for instance, reactive hydrazine or aminooxy groups for conjugation with carbonyl-containing molecules, such as aldehydes formed through periodate oxidation of carbohydrates or natively present at the reducing end of sugars and glycans. In other instances, crosslinking reagents may contain an amine-reactive group on one end to attach to the APTES-modified substrate and the other end can be a moiety that can intercalate DNA bases (for example, NHS esters of psoralen or other intercalating agents). Once SNAPs are immobilized by the intercalating interaction, they can be covalently crosslinked by thymidine adducts by exposure to UV light.

In some cases, the amine groups on ATPS surfaces may be acylated using glutaric anhydride to create carboxylate functionalities, which were then activated with NHS/DCC to form the NHS ester. This derivative could be used to couple amine-containing proteins and other molecules via amide bond formation. In a second activation strategy, the aminopropyl groups on the surface were activated with 1,4-phenylenediisothiocyanate (PDITC) to create terminal isothiocyanate groups for coupling amines. Both methods resulted in the successful coupling of amine-dendrimers to silica surfaces for use in arrays. In some cases, amine surfaces prepared using an aminosilane compound can be modified to contain carboxylate groups using the following protocol involving the reaction with an anhydride, such as succinic anhydride or glutaric anhydride. After modification, the carboxylates then can be used to couple amine-containing molecules using a carbodiimide reaction with EDC plus sulfo-NHS. In some cases, modification of an APTES surface with glutaric anhydride creates terminal carboxylates for coupling of amine-containing ligands which may be used for bioconjugation.

In some cases, aminosilane surfaces also may be activated by use of a bifunctional crosslinker to contain reactive groups for subsequent coupling to biomolecules. In one such reaction, N,N'-disuccinimidyl carbonate (DSC) was used to react with the amines on a slide surface and create terminal NETS-carbonate groups, which then could be coupled to amine-containing molecules, which may be used for bioconjugation. In some cases, APTES-modified surfaces can be activated with DSC to form amine-reactive succinimidyl carbonates for coupling proteins or other amine-containing molecules.

In some cases, silane coupling agents containing carboxylate groups may be used to functionalize a surface with carboxylic acids for subsequent conjugation with amine-containing molecules. For example, carboxyethylsilanetriol contains an acetate organo group on a silanetriol inorganic reactive end. The silanetriol component may be reactive immediately with inorganic —OH substrates without prior hydrolysis of alkoxy groups, as in the case with most other silanization reagents. In some cases, carboxyethylsilanetriol has been used to add carboxylate groups to fluorescent silica nanoparticles to couple antibodies for multiplexed bacteria monitoring. This reagent can be used in similar fashion to add carboxylate functionality to many inorganic or metallic nano-materials, which also will create negative charge repulsion to maintain particle dispersion in aqueous solutions. In some cases, covalent coupling to the carboxylated surface then can be done by activation of the carboxylic acid groups with a carbodiimide to facilitate direct reaction with amine-containing molecules or to form intermediate NHS esters, which may be used for bioconjugation. In some cases, carboxylethylsilanetriol can be used to modify an inorganic substrate to containing carboxylate groups for coupling amine-containing ligands.

In some cases, silane modification agents such as glycidoxy compounds may be utilized for bioconjugation to a surface substrate. Glycidoxy compounds contain reactive epoxy groups. Surfaces covalently coated with these silane coupling agents can be used to conjugate thiol-, amine-, or hydroxyl-containing ligands, depending on the pH of the reaction. In some cases, 3-glycidoxy-propyltrimethoxysilane (GOPTS) or 3-glycidoxypro-pyltriethoxysilane can be used to link inorganic silica or other metallic surfaces containing —OH groups with biological molecules containing any three of these major functional groups. In some cases, epoxy-containing silane coupling agents form reactive surfaces that can be used to couple amine-, thiol-, or hydroxyl-containing ligands which may be used for bioconjugation.

In some cases, the reaction of the epoxide with a thiol group yields a thioether linkage, whereas reaction with a hydroxyl gives an ether and reaction with an amine results in a secondary amine bond. The relative reactivity of an epoxy group is thiol>amine>hydroxyl, and this may be reflected by the optimal pH range for each reaction. In this case, the lower the reactivity of the functional group the higher the pH required to drive the reaction efficiently.

In some cases, isocyanates groups may be utilized for bioconjugation to a surface support. Isocyanate groups are extremely reactive toward nucleophiles and will hydrolyze rapidly in aqueous solution which are especially useful for covalent coupling to hydroxyl groups under nonaqueous conditions, which may be appropriate for conjugation to many carbohydrate ligands. Silanization can be accomplished in dry organic solvent to form reactive surfaces while preserving the activity of the isocyanates. Isocyanato-propyltriethoxysilane (ICPTES) contains an isocyanate group at the end of a short propyl spacer, which may be connected to the triethoxysilane group useful for attachment to inorganic substrates. In some cases, the isocyanate-containing silane coupling agent can be used to couple hydroxyl-containing molecules to inorganic surfaces which may be used for bioconjugation.

In some cases, ICPTES may be used to create novel chitosan-siloxane hybrid polymers by coupling the isocyanate groups to the functional groups of the carbohydrate and forming a silica polymer using the triethoxysilane backbone. In some cases, ICPTES and APTES have been used in combination to create organically modified silica xerogels through carboxylic acid solvolysis that formed hybrid materials with luminescent properties.

In some cases, nanoparticles or microparticles may be utilized as a surface support for bioconjugation. In some cases, particle types and compositions of almost limitless shape and size, including spherical, amorphous, or aggregate particles, as well as elaborate geometric shapes like rods, tubes, cubes, triangles, and cones. In addition, new symmetrical organic constructs have emerged in the nanometer range that include fullerenes (e.g., Bucky-balls), carbon nanotubes, and dendrimers, which are highly defined synthetic structures used as bioconjugation scaffolds. The chemical composition of particles may be just as varied as their shape. Particles can comprise of polymers or copolymers, inorganic constructs, metals, semiconductors, superparamagnetic composites, biodegradable constructs, synthetic dendrimers, and dendrons. Polymeric particles can be constructed from a number of different monomers or copolymer combinations. Some of the more common ones include polystyrene (traditional "latex" particles), poly(styrene/divinylbenzene) copolymers, poly(styrene/acrylate) copolymers, polymethylmethacrylate (PMMA), poly (hydroxyethyl methacrylate) (pHEMA), poly (vinyltoluene), poly(styrene/butadiene) copolymers, and poly(styrene/vinyltoluene) copolymers. In some cases, by mixing into the polymerization reaction combinations of functional monomers, one can create reactive or functional groups on the particle surface for subsequent coupling to affinity ligands. One example of this may be a poly(styrene/acrylate) copolymer particle, which creates carboxylate groups within the polymer structure, the number of which may be dependent on the ratio of monomers used in the polymerization process. In some cases, inorganic particles are used extensively in various bioapplications. For example, gold nanoparticles may be used for detection labels for immunohistochemical (IHC) staining and lateral flow diagnostic testing. In some cases, the use of particles in bioapplications like bioconjugation involves the attachment of affinity capture ligands to their surface, by either passive adsorption or covalent coupling. The coupling of an affinity ligand to such particles creates the ability to bind selectively biological targets in complex sample mixtures. The affinity particle complexes can thus be used to separate and isolate proteins or other biomolecules or to specifically detect the presence of these targets in cells, tissue sections, lysates, or other complex biological samples. In some cases, the reactions used for coupling affinity ligands to nanoparticles or microparticles are basically the same as those used for bioconjugation of molecules described herein.

In some cases, particle type used for bioapplications (e.g. bioconjugation) may be the polymeric microsphere or nanosphere, which comprises a spherical, nonporous, "hard" particle made up of long, entwined linear or crosslinked polymers. In some cases, creation of these particles involves an emulsion polymerization process that uses vinyl monomers, sometimes in the presence of divinyl crosslinking monomers. In some cases, larger microparticles may be built from successive polymerization steps through growth of much smaller nanoparticle seeds. In some cases, polymeric particles comprise of polystyrene or copolymers of styrene, like styrene/divinylbenzene, styrene/butadiene, sty-rene/acrylate, or styrene/vinyltoluene. Other common polymer supports include polymethylmethacrylate (PMMA), polyvinyltoluene, poly(hydroxyethyl meth-acrylate) (pHEMA), and the copolymer poly(ethylene glycol dimethacrylate/2-hydroxyethylmetacrylate) [poly(EGDMA/HEMA)].

In some cases, one method of attaching biomolecules to hydrophobic polymeric particles may be the use of passive adsorption. In some cases, protein adsorption onto hydrophobic particles takes place through strong interactions of nonpolar or aromatic amino acid residues with the surface polymer chains on the particles with concomitant exclusion of water molecules. Since proteins usually contain hydrophobic core structures with predominately hydrophilic surfaces, their interaction with hydrophobic particles must involve significant conformational changes to create large-scale hydrophobic contacts.

In some cases, particle types contain functional groups that are built into the polymer backbone and displayed on their surface. The quantity of these groups can vary widely depending on the type and ratios of monomers used in the polymerization process or the degree of secondary surface modifications that have been performed. In some cases, functionalized particles can be used to couple covalently biomolecules through the appropriate reaction conditions.

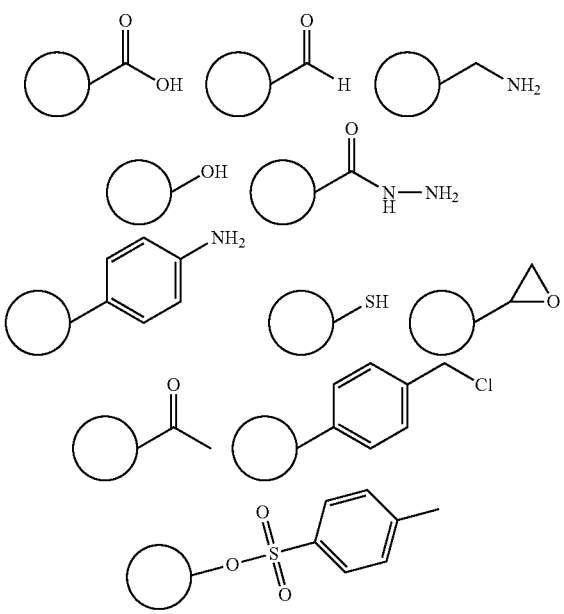

 = particle or solid support

Common Functional Groups or Reactive Groups on Particles for Bioconjugation

In some cases, a particle may couple with a crosslinker for bioconjugation.

In some cases, the rate of attachment of DNA SNAPs s to the solid support, or the efficacy or strength of attachment, may be altered by altering the sequence of DNA comprising the SNAP. For example, in the case of a DNA SNAP attached to a solid support by a reaction involving one or more thymines the attachment may be varied by varying the number of thymines in the DNA sequence. In some cases, increasing the number of thymines may facilitate the attachment of the SNAP to the solid support.

In some cases, the solid support may be a part of a flow cell. In some cases, the SNAPs may be attached to a solid support in a flow cell. In some cases, the SNAPs may be directly conjugated to a solid support in a flow cell. In some cases, the SNAPs may be adsorbed to a solid support in a flow cell. Attaching the SNAPs in the flow cell may allow visualization of the SNAPs as they attach to the solid support. The attachment of the SNAPs may be optimized by monitoring the number of attached SNAPs compared to the number of attachment sites during the attachment process. In some cases, the attachment of the SNAPs may be optimized by monitoring the area of the solid support covered by the SNAPs and the area of the solid support that may be unoccupied by the SNAPs during the attachment process.

In some cases, the SNAPs may be conjugated directly in a flow cell. In some cases, the SNAPs may be conjugated to a surface within the flow cell. In some cases, the SNAPs may be conjugated to a surface within the flow cell before being conjugated to the biological, chemical, or physical entities. In some cases, a biological, chemical, or physical entity may be flowed into a flow cell and conjugated to a SNAP that may be already conjugated to the solid support. In some cases, a biological, chemical, or physical entity may be conjugated to a SNAP before said SNAP may be introduced into a flow cell and conjugated to a solid support in a flow cell. In some cases, a biological, chemical, or physical entity and a SNAP may be introduced into a flow cell and conjugated to each other within the flow cell, before the SNAP may be conjugated to a solid support within the flow cell.

In some cases, the biological, chemical, or physical entities may be conjugated to the SNAPs prior to attaching the SNAPs to a solid support. After performing such a reaction the products may be purified to separate out conjugated SNAP-biological/chemical entity moieties from unconjugated SNAPs and biological/chemical entities.

The methods of this disclosure may be used to spatially separate biological, chemical, or physical entities. In some embodiments, methods of this disclosure may be used to spatially separate proteins, small molecules, DNAs, RNAs, glycoproteins, metabolites, carbohydrates, enzymes, or antibodies. In some embodiments, methods of this disclosure may be used to spatially separate complexes, such as protein complexes comprising two or more proteins, protein nucleic acid complexes, or other complexes. In some cases, the methods may be used to spatially separate viral particles or viroids. In some cases, the methods may be used to separate cells, such as bacterial cells, microbial cells, mammalian cells or other cells.

In some embodiments, the SNAP may be formed on the seed prior to the seed being attached to the biological, chemical, or physical entity.

In some embodiments this disclosure provides a composition comprising a nucleic acid SNAP attached to a protein, a nucleic acid SNAP attached to a small molecule, a nucleic acid SNAP attached to a protein complex, a nucleic acid SNAP attached to a protein nucleic acid SNAP, a nucleic acid SNAP attached to a carbohydrate, a nucleic acid SNAP attached to a viral particle or a nucleic acid SNAP attached to a cell.

In some embodiments this disclosure provides a composition comprising a dendrimer attached to a protein, a dendrimer attached to a small molecule, a dendrimer attached to a protein complex, a dendrimer attached to a protein dendrimer, a dendrimer attached to a carbohydrate, a dendrimer attached to a viral particle or a dendrimer attached to a cell.

In some cases, the biological, chemical, or physical entities may be eluted from the solid support either by cleaving a photo-cleavable bond, or by chemically or enzymatically digesting the SNAP.

In some cases, the biological, chemical, or physical entities may attach to the solid support directly, while the SNAPs occlude other biological, chemical, or physical entities from attaching in the immediate vicinity. In some cases the biological, chemical, or physical entities may attach directly to an attachment site within a microwell or nanowell, and the size of the SNAPs may be selected to prevent more than one SNAP from occupying the microwell or nanowell. In such cases, the SNAP may be removed, either by cleaving a photo-cleavable bond, or by chemically or enzymatically digesting the SNAP.

In some embodiments, SNAPs of this disclosure may be used as nanoparticles. For example, SNAPs of this disclosure may be used as nanoparticles for detection or visualization. In some cases, a nucleic acid SNAP may be formed which incorporates modified nucleotides which comprise fluorescent moieties. Any fluorescently labeled nucleotide known in the art may be used in a SNAP of this disclosure. Examples of fluorescently labeled nucleotides include, but are not limited to, Alexa Fluor™ 555-aha-dCTP, Alexa Fluor™ 555-aha-dUTP, 1 mM in TE buffer, Alexa Fluor™ 647 ATP (Adenosine 5'-Triphosphate, Alexa Fluor™ 647 2'-(or-3)-O—(N-(2-Aminoethyl) Urethane), Hexa(Triethylammonium) Salt), Alexa Fluor™ 647-aha-dCTP, Alexa Fluor™ 647-aha-dUTP, 1 mM in TE buffer, BODIPY™ FL ATP (Adenosine 5'-Triphosphate, BODIPY™ FL 2"-(or-3)-O—(N-(2-Aminoethyl)Urethane), Trisodium Salt), 5 mM in buffer, BODIPY™ FL ATP-γ-S, Thioester (Adenosine 5'-O-(3-Thiotriphosphate), BODIPY™ FL Thioester, Sodium Salt), BODIPY™ FL GDP (Guanosine 5'-Diphosphate, BODIPY™ FL 2'-(or-3)-O—(N-(2-Aminoethyl) Urethane), Bis (Triethylammonium) Salt), ChromaTide™ Alexa Fluor™ 488-5-UTP, ChromaTide™ Alexa Fluor™ 488-5-dUTP, ChromaTide™ Alexa Fluor™ 546-14-UTP, ChromaTide™ Alexa Fluor™ 546-14-dUTP, ChromaTide™ Alexa Fluor™ 568-5-dUTP, ChromaTide™ Alexa Fluor™ 594-5-dUTP, ChromaTide™ Fluorescein-12-dUTP, ChromaTide™ Texas Red™-12-dUTP, Fluorescein-12-dUTP Solution (1 mM), Fluorescein-aha-dUTP—1 mM in TE Buffer, Guanosine 5'-O-(3-Thiotriphosphate), BODIPY™ FL Thioester, Sodium Salt (BODIPY™ FL GTP-γ-S, Thioester), Guanosine 5'-Triphosphate, BODIPY™ FL 2'-(or-3)-O—(N-(2-Aminoethyl) Urethane), Trisodium Salt (BODIPY™ FL GTP), Guanosine 5'-Triphosphate, BODIPY™ TR 2'-(or-3)-O—(N-(2-Aminoethyl) Urethane), Trisodium Salt (BODIPY™ TR GTP), MANT-ADP (2'-(or-3)-O—(N-Methylanthraniloyl) Adenosine 5'-Diphosphate, Disodium Salt), MANT-ATP (2'-(or-3)-O—(N-Methyl anthraniloyl) Adenosine 5'-Triphosphate, Trisodium Salt), MANT-GDP (2'-(or-3)-O—(N-Methylanthraniloyl) Guanosine 5'-Diphosphate, Disodium Salt), MANT-GMPPNP (2'-(or-3)-O—(N-Methylanthraniloyl)-β:γ-Imidoguanosine 5'-Triphosphate, and Trisodium Salt), MANT-GTP (2'-(or-3)-O—(N-Methylanthraniloyl) Guanosine 5'-Triphosphate, Trisodium Salt).

In some cases, a SNAP of this disclosure may be designed such that probes may be attached onto the surface of the SNAP. A SNAP with attached probes may be used as a detection reagent. In some cases, a SNAP with attached probes may be also labeled with fluorescent moieties to form a fluorescent detection reagent. In some cases, a SNAP with attached probes and fluorescent moieties may provide a high degree of signal amplification. The amount of probes on the SNAP may be titrated to achieve a desired degree of sample amplification. In some cases, differently sized SNAPs may be attached to different probes. In some cases, differently colored SNAPs may be attached to different probes. In some cases a library of different probes may be attached to fluorescently labeled SNAPs such that a first probe may be attached to a SNAP which may be a different size and/or color from a SNAP each other probe may be attached to.

A biomolecule may be coupled to an array on a solid support that is coupled to a light sensing device comprising a plurality of pixels, where each pixel is capable of independently sensing incident light. The biomolecule may be directly coupled to the support or may be coupled by linking molecule (e.g., a SNAP or a magnetic nanoparticle). The biomolecule may be coupled to the solid support coupled to the light sensing device by covalent conjugation or a non-covalent interaction (e.g., electrostatic adhesion). Coupled biomolecules on an array may comprise a protein, peptide, DNA molecule, RNA molecule, carbohydrate, binding ligand, or a complex comprising more than one molecule of any of the aforementioned biomolecules.

An array comprising a plurality of biomolecules may have any configuration of biomolecules on the array. An array comprising a plurality of biomolecules may comprise about 10, 100, 1000, 10000, 100000, 1000000, 10000000, 100000000, 1000000000, 10000000000 or more than 10000000000 biomolecules. An array comprising a plurality of biomolecules may comprise at least about 10, 100, 1000, 10000, 100000, 1000000, 10000000, 100000000, 1000000000, 10000000000 or more than 10000000000 biomolecules. An array comprising a plurality of biomolecules may comprise about 10000000000, 1000000000, 100000000, 10000000, 1000000, 100000, 10000, 1000, 100, 10 or less than 10 biomolecules.

An array comprising a plurality of biomolecules may comprise an ordered array. An ordered array comprising a plurality of biomolecules may be created on a structured or ordered surface (e.g., an array created by nanolithography of a substrate). An array comprising a plurality of biomolecules may comprise a non-ordered array (e.g., random distribution of attachment sites for biomolecules). An array comprising a plurality of biomolecules may have a one-dimensional configuration, two-dimensional configuration (attachment to a flat surface or a planar surface), or three-dimensional configuration (attachment on a non-planar or curved surface, e.g., nanowells, beads).

An array comprising a plurality of coupled biomolecules may have complete occupancy of attachment sites or less than complete occupancy of binding sites. An array comprising a plurality of binding sites may comprise a sparse array if it has more unoccupied attachments sites than occupied attachment sites. An array comprising a plurality of binding sites may comprise a dense array if it has more occupied attachment sites than unoccupied sites. An array may be characterized by an occupancy count or a vacancy count. An occupancy count or a vacancy count may be absolute (e.g., M attachment sites are unoccupied, N attachment sites are occupied) or relative (e.g., X % of binding sites are unoccupied, Y % of attachment sites are occupied). An array comprising a plurality of biomolecules may have an occupancy count or vacancy count of about 0.1%, 1%, 5%, 10%, 15%, 20%, 25%, 30%, 35%, 40%, 45%, 50%, 55%, 60%, 65%, 70%, 75%, 80%, 85%, 90%, 95%, 99%, 99.9%, or more than 99.9%. An array comprising a plurality of biomolecules may have an occupancy count or vacancy count of at least about 0.1%, 1%, 5%, 10%, 15%, 20%, 25%, 30%, 35%, 40%, 45%, 50%, 55%, 60%, 65%, 70%, 75%, 80%, 85%, 90%, 95%, 99%, 99.9%, or more than 99.9%. An array comprising a plurality of biomolecules may have an occupancy count or vacancy count of no more than about 99.9%, 99%, 95%, 90%, 85%, 80%, 75%, 70%, 65%, 60%, 55%, 50%, 45%, 40%, 35%, 30%, 25%, 20%, 15%, 10%, 5%, 1%, 0.1%, or less than 0.1%. An occupancy count or a vacancy count may be determined over an entire array or a subsection, area, or region of an array comprising a plurality of biomolecules.

An array may be characterized by an occupancy rate or a vacancy rate. An occupancy rate or vacancy rate may be defined as the number of occupied or unoccupied attachment sites, respectively, per some reference number of sites. An array may have an occupancy rate or a vacancy rate of about 1 in 10, 1 in 20, 1 in 50, 1 in 100, 1 in 200, 1 in 500, 1 in 1000, 1 in 2000, 1 in 5000, 1 in 10000, 1 in 20000, 1 in 50000, 1 in 100000, 1 in 200000, 1 in 500000, 1 in 1000000, or more than 1 in 1000000. An array may have an occupancy rate or a vacancy rate of at least about 1 in 10, 1 in 20, 1 in 50, 1 in 100, 1 in 200, 1 in 500, 1 in 1000, 1 in 2000, 1 in 5000, 1 in 10000, 1 in 20000, 1 in 50000, 1 in 100000, 1 in 200000, 1 in 500000, 1 in 1000000, or more than 1 in 1000000. An array may have an occupancy rate or a vacancy rate of no more than about 1 in 1000000, 1 in 500000, 1 in 200000, 1 in 100000, 1 in 50000, 1 in 20000, 1 in 10000, 1 in 5000, 1 in 2000, 1 in 1000, 1 in 500, 1 in 200, 1 in 100, 1 in 50, 1 in 20, 1 in 10, or less than 1 in 10. An occupancy rate or a vacancy rate may be determined over an entire array or a subsection, area, or region of an array comprising a plurality of biomolecules.

Figure 9C:
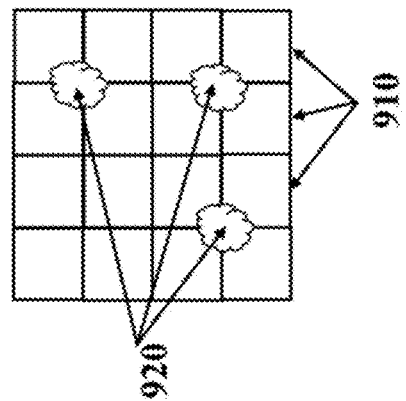
FIGS. 9A, 9B, and 9C depict various surface densities of single molecule biomolecule arrays configured over detection pixels, in accordance with disclosed embodiments.
Figure 9B:
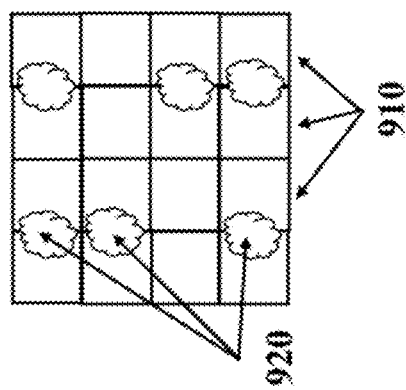
Figure 9A:
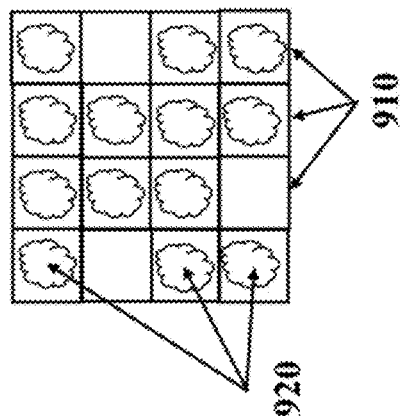

A plurality of biomolecules may be coupled to a solid support at a surface density that is determined by the size of each pixel of a light sensing device. Biomolecules may be conjugated to a solid support such that each pixel of the light sensing device detects a single biomolecule. In some cases, biomolecules may be coupled to a solid support such that each biomolecule is detected by more than one pixel. FIGS. 9A-9C depict top-down views of pixel arrays with biomolecules deposited at differing densities. FIG. 9A depicts a view of a pixel array comprising 16 contiguous pixels 910 with biomolecules 920 deposited at a density of about 1 biomolecule per pixel, although the occupancy of the array is less than 100%. FIGS. 9B and 9C depict arrays with 2 pixels 910 per biomolecule 920 and 4 pixels 910 per biomolecule 920, respectively, at less than 100% occupancy of binding sites for biomolecules. Having more than one pixel available per biomolecule may increase the accuracy and sensitivity of the detection device. Biomolecules may be coupled to the solid support that is coupled to the light sensing device at a surface density of at least about 1 pixel per biomolecule, 2 pixels per biomolecule, 3 pixels per biomolecule, 4 pixels per biomolecule, 5 pixels per biomolecule, 6 pixels per biomolecule, 7 pixels per biomolecule, 8 pixels per biomolecule, 9 pixels per biomolecule, 10 pixels per biomolecule, 15 pixels per biomolecule, 20 pixels per biomolecule, 25 pixels per biomolecule, 50 pixels per biomolecule, 100 pixels per biomolecule, or more than about 100 pixels per biomolecule. Biomolecules may be coupled to the solid support that is coupled to the light sensing device at a surface density of no more than about 100 pixel per biomolecule, 50 pixels per biomolecule, 25 pixels per biomolecule, 20 pixels per biomolecule, 15 pixels per biomolecule, 10 pixels per biomolecule, 9 pixels per biomolecule, 8 pixels per biomolecule, 7 pixels per biomolecule, 6 pixels per biomolecule, 5 pixels per biomolecule, 4 pixels per biomolecule, 3 pixels per biomolecule, 2 pixels per biomolecule, or less than 2 pixels per biomolecule. A solid support may have a biomolecule occupancy based upon the total number of available attachment sites of at least about 5%, 10%, 15%, 20%, 25%, 30%, 35%, 40%, 45%, 50%, 55%, 60%, 65%, 70%, 75%, 80%, 85%, 90%, 95%, 99%, or more than 99%. A solid support may have a biomolecule occupancy based upon the total number of available attachment sites of no more than about 99%, 95%, 90%, 85%, 80%, 75%, 70%, 65%, 60%, 55%, 50%, 45%, 40%, 35%, 30%, 25%, 20%, 15%, 10%, 5%, or less than 5%.

Each pixel of a light sensing device coupled to a solid support may be capable of detecting the interaction of incident light with a biomolecule coupled to the solid support. In some cases, the interaction of the incident light with the biomolecule may comprise the absorbance of the incident light, the transmission of the incident light, the reflection or refraction of the incident light, or the emission of photons of differing wavelength in response to incident light. Each pixel of the light sensing device may detect the presence or absence of incident photons. Each pixel of the light sensing device may be capable of detecting the intensity of incident photons.

In some cases, a light sensing device coupled to a solid support may detect the interaction of an affinity reagent or a plurality of affinity reagents with one or more biomolecules coupled to the solid support. The interaction of the affinity reagent may include a non-covalent interaction such as binding or complex formation of the affinity reagent with the biomolecule. The interaction of the affinity reagent may include a covalent interaction such as the reaction of the affinity reagent with the biomolecule. A biomolecule may comprise a detectable label such as a fluorophore, radiolabel, or bioluminescent moiety that may transmit light to a pixel of a light sensing device.

Figure 10:
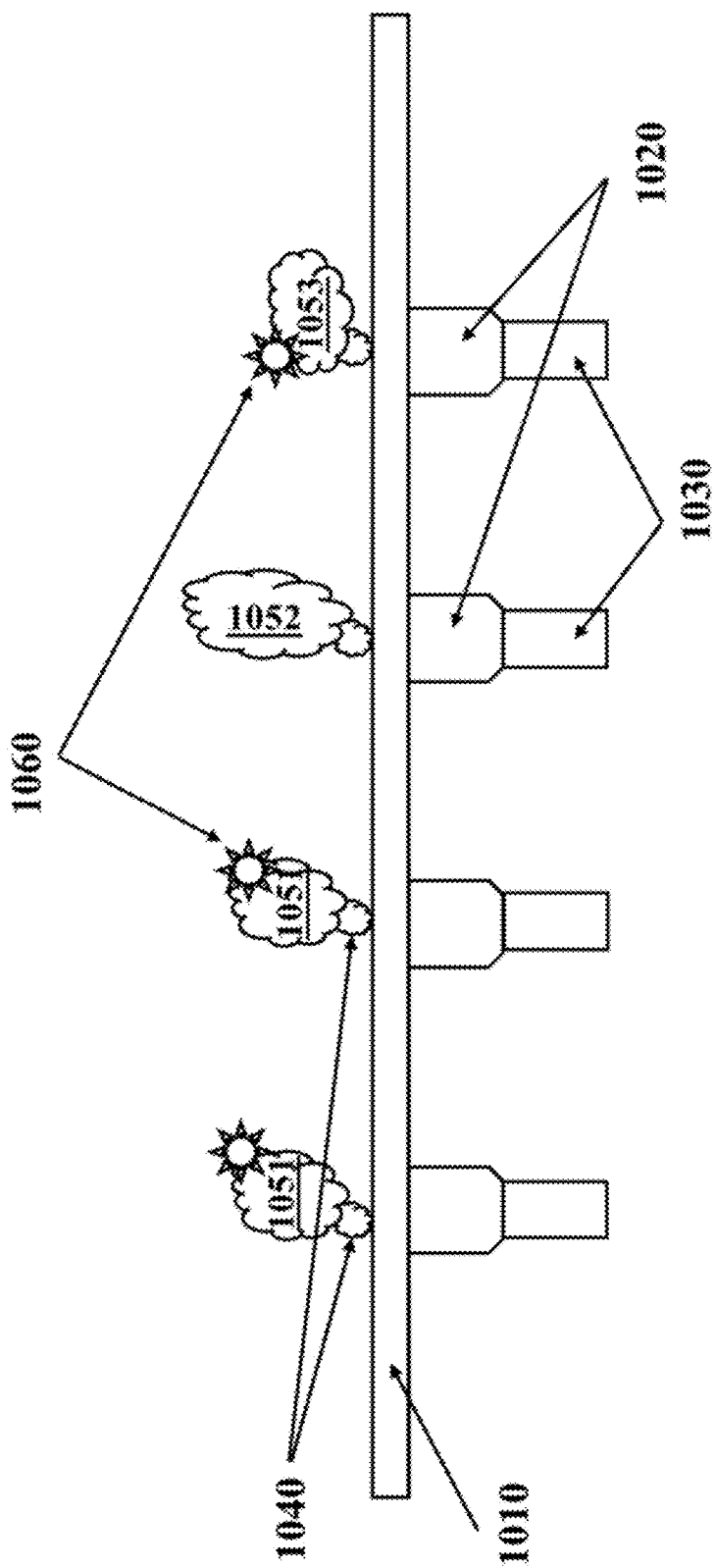
FIG. 10 illustrates a cross-sectional view of an array of biomolecules coupled to a solid support with integrated light-sensing devices, with detectable affinity reagents coupled to some of the biomolecules, in accordance with disclosed embodiments.

FIG. 10 depicts a cross-sectional view of a light sensing device coupled to an array of biomolecules, in accordance with some embodiments. A solid support 1010 is coupled to an array of light sensing pixels, with each pixel comprising a nanowell 1020 and a light sensing element 1030. At the surface of the solid support 1010, linking molecules 1040 (e.g. SNAPs) bind differing biomolecules 1051, 1052, and 1053 to the solid support. Detectable affinity reagents 1060 bind to biomolecules 1051 and 1053, but do not bind to biomolecule 1052. In the presence of an exciting radiation field, photons of emitted light may be transferred from the detectable labels 1060 to the corresponding light sensing element 1030.

Affinity reagents may include aptamers, antibodies, antibody fragments, mini-peptide binders, avimers, peptimers, phage display, metal nanoparticles (e.g., TiO2 nanoparticles), and magnetic nanoparticles (e.g., paramagnetic nanoparticles). Affinity reagents may also include reagents that interact in identifiable manners with biomolecules, such as kinases, proteases, restriction enzymes, reducing agents, oxidizing agents, and reactive labels (e.g., amine-reactive dyes or thiol-reactive dyes). An interaction of a reactive affinity reagent may be detected directly by methods such as fluorescence detection, luminescence detection, or surface plasmon resonance. An interaction of a reactive affinity reagent may be detected by a change in the properties of a biomolecule (e.g., removal of a protein-linked fluorophore caused by the action of a protease). An interaction of a reactive affinity reagent may be detected indirectly by secondary interactions with reactive affinity reagents. For example, an affinity reagent may comprise a cross-linking reagent that contains an amine-reactive or thiol-reactive group for reacting with a protein side chain and a second reactive group that can be reacted with other detectable reagents (fluorophores, magnetic particles, etc.). In some cases, more than one affinity reagent may be linked to form an affinity reagent complex (e.g., two linked aptamers, an aptamer linked to a protease). Affinity reagents complexes may be used to obtain additional information when characterizing the interaction of the affinity reagent complex with a protein or peptide. For example, an affinity reagent complex may be used to determine if an epitope is within a certain proximity to another epitope.

An affinity agent may have a known or characterized degree of nonspecificity. A degree of nonspecificity may be defined as the property of binding to more than one unique biomolecule. For example, an affinity reagent may comprise a degree of nonspecificity if it binds to any protein that contains an epitope from the family of epitopes defined by the sequence X1-X2-G, where X1 and X2 may be any amino acid residue or a known subset of amino acid residues (e.g., M-F-G, K-W-G, S-K-G, W-A-G, etc.). An affinity reagent with a degree of nonspecificity may bind to more than one family of epitopes (e.g., A-X2-T and G-X2-E). An affinity reagent with a degree of nonspecificity may bind to epitopes with a common structural pattern (e.g., all positive or neutral charge side chains). An affinity reagent with a degree of nonspecificity may bind to a random, known set of amino acid epitopes (e.g., K-D-S, R-M-W, D-T-C, etc.). An affinity reagent may have a degree of nonspecificity if it binds to more than one protein molecule with a family of proteins molecules or if it binds to more than one type of protein molecule. An affinity reagent may have a known or characterized degree of nonspecificity if the binding of the affinity reagent has been observed to bind to more than one protein molecule. In some cases, the degree of nonspecificity of an affinity reagent may be described in a probabilistic fashion (e.g., binding of an affinity reagent is observed in at least 25%, 50%, 75%, 90% or more of proteins comprising the epitope G-X-G). An affinity reagent with a degree of nonspecificity may be observed to bind to a subset of protein molecules within a proteome with the binding being linked to a known common structural element within the subset of protein molecules (e.g., a common epitope, a common post-translational modification). An affinity reagent with a degree of nonspecificity may be observed to bind to a subset of protein molecules within a proteome without the binding being linked to a known common structural element within the subset of protein molecules (e.g., no common epitope, no common post-translational modification). Each unique affinity reagent may have a unique binding profile when interacting with a plurality of differing biomolecules (e.g., a heterogeneous plurality of proteins derived from a single cell) such that the affinity reagent may only be detected at pixels where a biomolecule containing a target epitope is located. A series or sequence of differing affinity reagents may produce a series or sequence of detected binding patterns when allowed to interact with a plurality of biomolecules coupled to the solid support or a light sensing device.

The interaction of an affinity reagent with a biomolecule may occur over a particular time interval. The interaction of an affinity reagent may occur for a long enough time interval for the interaction to be detected by the light sensing device. A pixel of a light sensing device may be capable of detecting an interaction between an affinity reagent and a biomolecule that occurs for at least about 1 microsecond (μs), 10 μs, 50 μs, 100 μs, 250 μs, 500 μs, 1 millisecond (ms), 10 ms, 50 ms, 100 ms, 250 ms, 500 ms, 1 second (s), 5 s, 10 s, 30 s, 1 minute (min), 5 min, 10 min, or more than about 10 minutes. A pixel of a light sensing device may be capable of detecting an interaction between an affinity reagent and a biomolecule that occurs for no more than about 10 min, 5 min, 1 min, 30 second (s), 10 s, 5 s, 1 s, 500 millisecond ms, 250 ms, 100 ms, 50 ms, 10 ms, 1 ms, 500 μs, 250 μs, 1000 μs, 50 μs, 10 μs, 1 μs, or less than about 1 μs.

A pixel on a light sensing device may be configured to minimize cross-talk or incident light emitted from entities not associated with the pixel. In some cases, adjacent pixels on a light sensing device may be spaced, oriented or shaped to minimize cross-talk or incident light emitted from entities not associated with the pixel. For example, a plurality of biomolecules (e.g., proteins) may be coupled to a solid support such that each individual biomolecule is coupled to a portion of the solid support associated with one or more unique pixels on a light sensing device. The biomolecules may have light-emitting or light-absorbing entities (e.g., fluorophores) that interact with the biomolecules (e.g., an affinity reagent) at some or all of the biomolecules. A pixel may be arranged to minimize the amount of light received from a light-emitting entity not associated with the pixel. In some cases, the amount of incident light at a particular pixel may fall below the threshold of detection for the pixel. In some cases, the incident light at a particular pixel may comprise no more than about 50%, 45%, 40%, 35%, 30%, 25%, 20%, 15%, 10%, 5%, 4%, 3%, 2%, 1%, 0.9%, 0.8%, 0.7%, 0.6%, 0.5%, 0.4%, 0.3%, 0.2%, 0.1%, 0.05%, 0.01%, 0.005%, 0.001%, or less than 0.001% light from non-associated entities.

Figure 3:
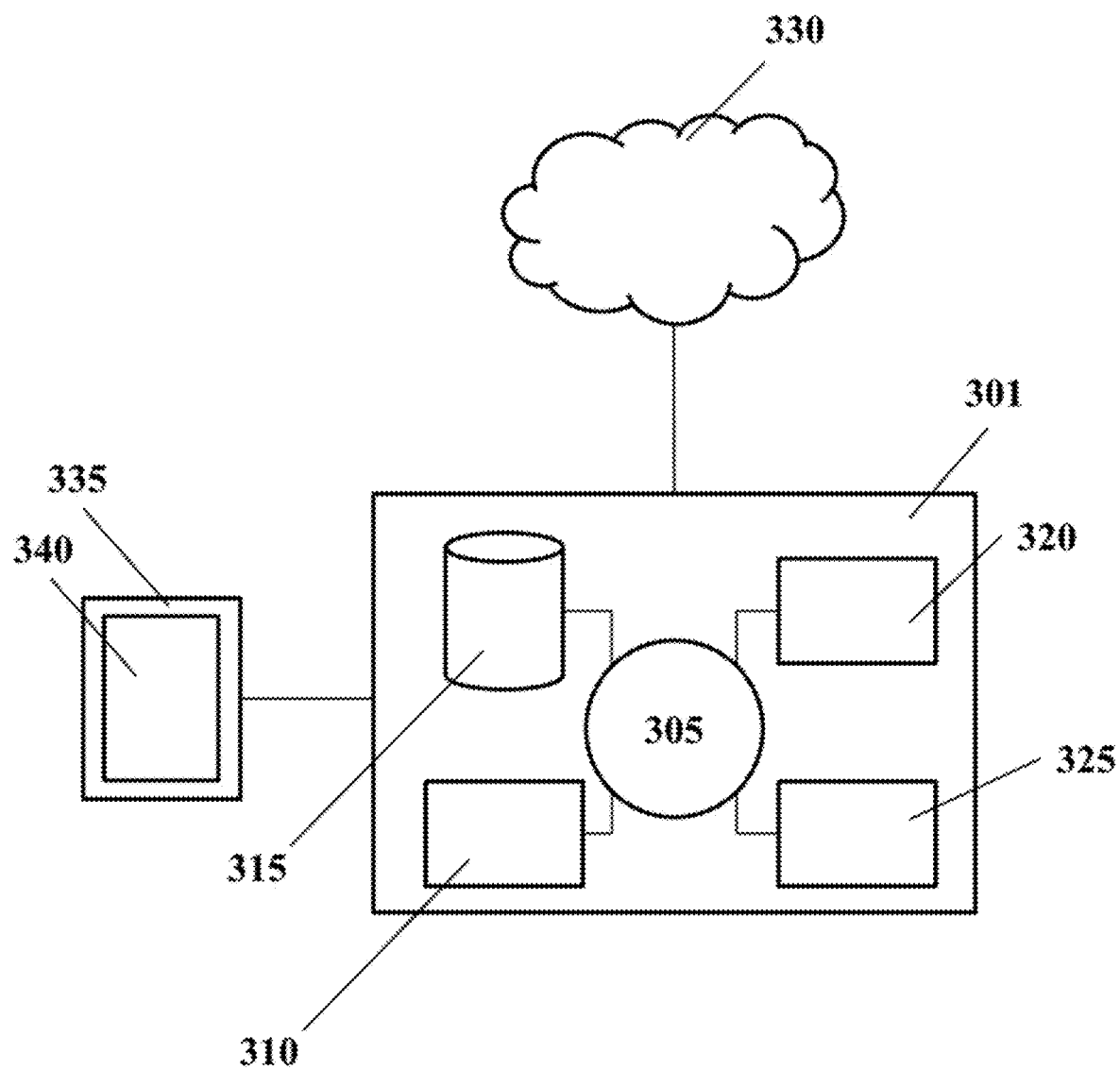
FIG. 3 illustrates a computer system that is programmed or otherwise configured to implement methods provided herein.

The present disclosure provides computer systems that are programmed to implement methods of the disclosure. FIG. 3 shows a computer system 301 that is programmed or otherwise configured to, for example, acquire pixel information of an array of biological, chemical, or physical entities; and detect the array of biological, chemical, or physical entities based at least in part on the acquired pixel information. The computer system 301 can regulate various aspects of analysis, calculation, and generation of the present disclosure, such as, for example, acquiring pixel information of an array of biological, chemical, or physical entities; and detecting the array of biological, chemical, or physical entities based at least in part on the acquired pixel information. The computer system 301 can be an electronic device of a user or a computer system that is remotely located with respect to the electronic device. The electronic device can be a mobile electronic device.

The computer system 301 includes a central processing unit (CPU, also "processor" and "computer processor" herein) 305, which can be a single core or multi core processor, or a plurality of processors for parallel processing. The computer system 301 also includes memory or memory location 310 (e.g., random-access memory, read-only memory, flash memory), electronic storage unit 315 (e.g., hard disk), communication interface 320 (e.g., network adapter) for communicating with one or more other systems, and peripheral devices 325, such as cache, other memory, data storage and/or electronic display adapters. The memory 310, storage unit 315, interface 320 and peripheral devices 325 are in communication with the CPU 305 through a communication bus (solid lines), such as a motherboard. The storage unit 315 can be a data storage unit (or data repository) for storing data. The computer system 301 can be operatively coupled to a computer network ("network") 330 with the aid of the communication interface 320. The network 330 can be the Internet, an internet and/or extranet, or an intranet and/or extranet that is in communication with the Internet. The network 330 in some cases is a telecommunication and/or data network. The network 330 can include one or more computer servers, which can enable distributed computing, such as cloud computing. For example, one or more computer servers may enable cloud computing over the network 330 ("the cloud") to perform various aspects of analysis, calculation, and generation of the present disclosure, such as, for example, acquiring pixel information of an array of biological, chemical, or physical entities; and detecting the array of biological, chemical, or physical entities based at least in part on the acquired pixel information. Such cloud computing may be provided by cloud computing platforms such as, for example, Amazon Web Services (AWS), Microsoft Azure, Google Cloud Platform, and IBM cloud. The network 330, in some cases with the aid of the computer system 301, can implement a peer-to-peer network, which may enable devices coupled to the computer system 301 to behave as a client or a server.

The CPU 305 can execute a sequence of machine-readable instructions, which can be embodied in a program or software. The instructions may be stored in a memory location, such as the memory 310. The instructions can be directed to the CPU 305, which can subsequently program or otherwise configure the CPU 305 to implement methods of the present disclosure. Examples of operations performed by the CPU 305 can include fetch, decode, execute, and writeback.

The CPU 305 can be part of a circuit, such as an integrated circuit. One or more other components of the system 301 can be included in the circuit. In some cases, the circuit is an application specific integrated circuit (ASIC).

The storage unit 315 can store files, such as drivers, libraries and saved programs. The storage unit 315 can store user data, e.g., user preferences and user programs. The computer system 301 in some cases can include one or more additional data storage units that are external to the computer system 301, such as located on a remote server that is in communication with the computer system 301 through an intranet or the Internet.

The computer system 301 can communicate with one or more remote computer systems through the network 330. For instance, the computer system 301 can communicate with a remote computer system of a user (e.g., a physician, a nurse, a caretaker, a patient, or a subject). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 301 via the network 330.

Methods as described herein can be implemented by way of machine (e.g., computer processor) executable code stored on an electronic storage location of the computer system 301, such as, for example, on the memory 310 or electronic storage unit 315. The machine executable or machine readable code can be provided in the form of software. During use, the code can be executed by the processor 305. In some cases, the code can be retrieved from the storage unit 315 and stored on the memory 310 for ready access by the processor 305. In some situations, the electronic storage unit 315 can be precluded, and machine-executable instructions are stored on memory 310.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 301 can include or be in communication with an electronic display 335 that comprises a user interface (UI) 340 for providing, for example, determined quantitative measures generated from a blood sample of a subject, statistical measures of deviation of the counts, and determined tumor progression or tumor non-progression of the subject. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 305. The algorithm can, for example, acquire pixel information of an array of biological, chemical, or physical entities; and detect the array of biological, chemical, or physical entities based at least in part on the acquired pixel information.

EXAMPLES

Figure 4:
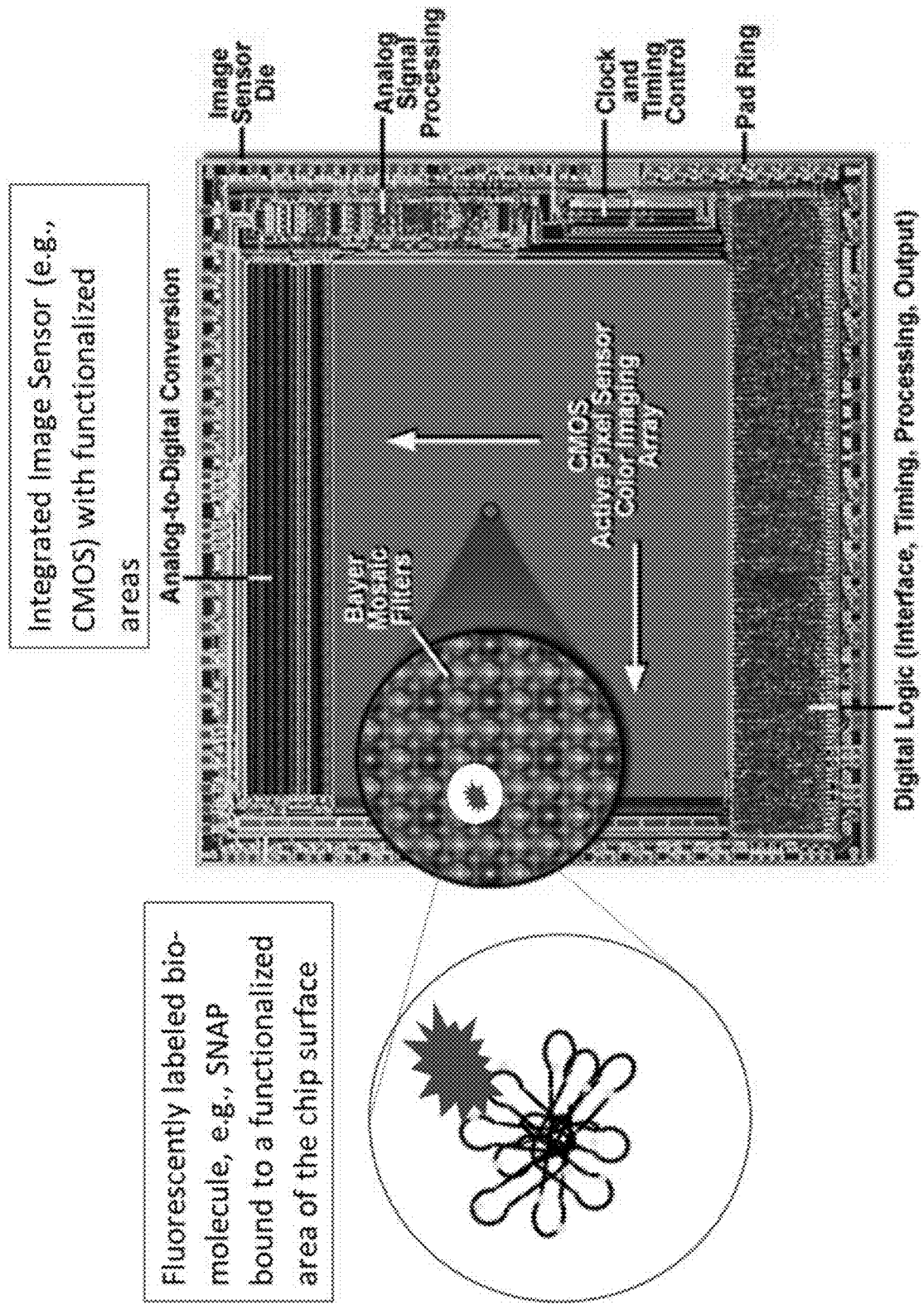
FIG. 4 illustrates a top view of an array of light-sensing devices with fluorescently labeled biomolecules bound to a functionalized area of the chip surface (e.g., immobilized SNAPs) and a probe, in accordance with disclosed embodiments.

Example 1: Array of Light-Sensing Devices with Fluorescently Labeled Biomolecules Bound to a Functionalized Area of the Chip Surface (e.g., Immobilized SNAPs) and a Probe FIG. 4 illustrates a top view of an array of light-sensing devices with fluorescently labeled biomolecules bound to a functionalized area of the chip surface (e.g., immobilized SNAPs) and a probe, in accordance with disclosed embodiments. The array of light-sensing devices may be integrated with digital logic (e.g., interface, timing, processing, and output). The array of light-sensing devices may be integrated with an integrated image sensor (e.g., CMOS sensor) with functionalized areas. The CMOS sensor may be a CMOS active pixel sensor color imaging array.

Figure 5:
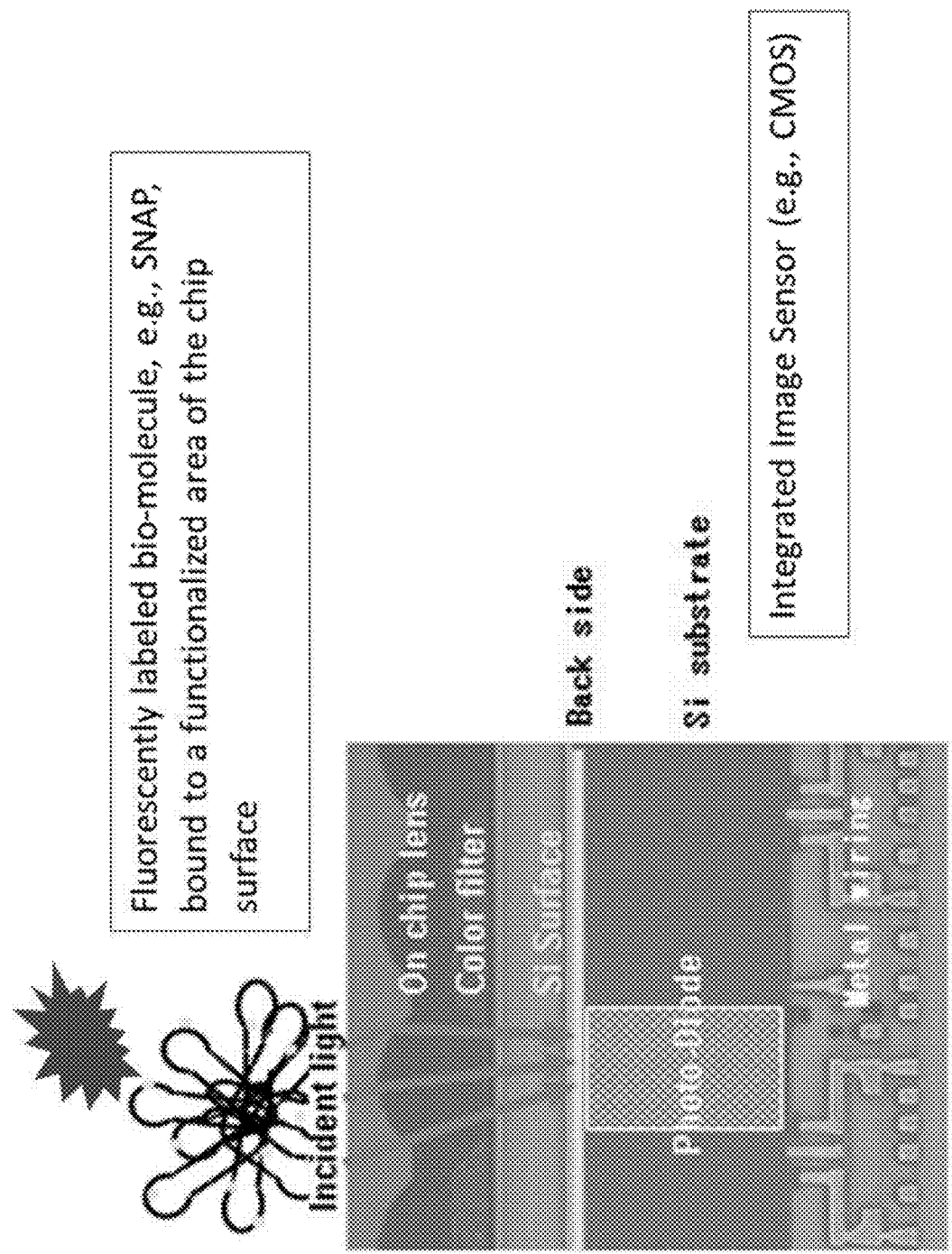
FIG. 5 illustrates a cross-sectional view of one pixel of a light-sensing device with fluorescently labeled biomolecules bound to a functionalized area of the chip surface (e.g., immobilized SNAPs) and a probe, in accordance with disclosed embodiments.

FIG. 5 illustrates a cross-sectional view of one pixel of a light-sensing device with fluorescently labeled biomolecules bound to a functionalized area of the chip surface (e.g., immobilized SNAPs) and a probe, in accordance with disclosed embodiments. Incident light may be collected by an on-chip lens and then processed by a color filter. When the incident light hits the silicon surface on the backside of the silicon substrate, a photo-diode can collect the photons of the incident light and convert the photons into electrons. In some embodiments, an on-chip lens may not be needed.

Figure 6:
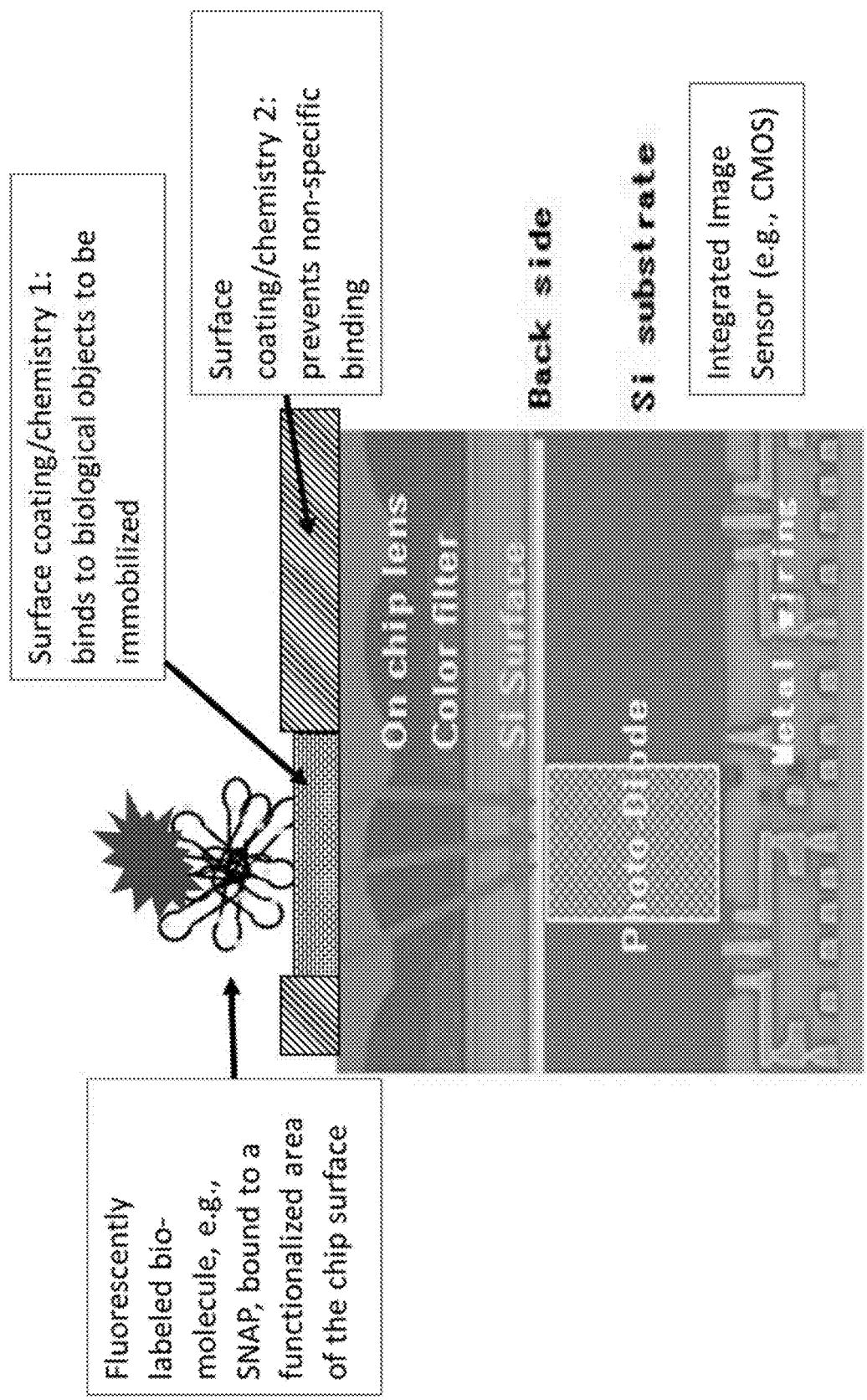
FIG. 6 illustrates a cross-sectional view of one pixel of a light-sensing device with fluorescently labeled biomolecules bound to a functionalized area of the chip surface (e.g., immobilized SNAPs), a probe, and a differential surface coating, in accordance with disclosed embodiments.

Example 2: Array of Light-Sensing Devices with Fluorescently Labeled Biomolecules Bound to a Functionalized Area of the Chip Surface (e.g., Immobilized SNAPs), a Probe, and a Differential Surface Coating FIG. 6 illustrates a cross-sectional view of one pixel of a light-sensing device with fluorescently labeled biomolecules bound to a functionalized area of the chip surface (e.g., immobilized SNAPs), a probe, and a differential surface coating, in accordance with disclosed embodiments. A first surface coating or chemistry may bind to biological objects to be immobilized. A second surface coating or chemistry may prevent non-specific binding. Incident light may be collected by an on-chip lens and then processed by a color filter. When the incident light hits the silicon surface on the backside of the silicon substrate, a photo-diode can collect the photons of the incident light and convert the photons into electrons. In some embodiments, an on-chip lens may not be needed.

Figure 7:
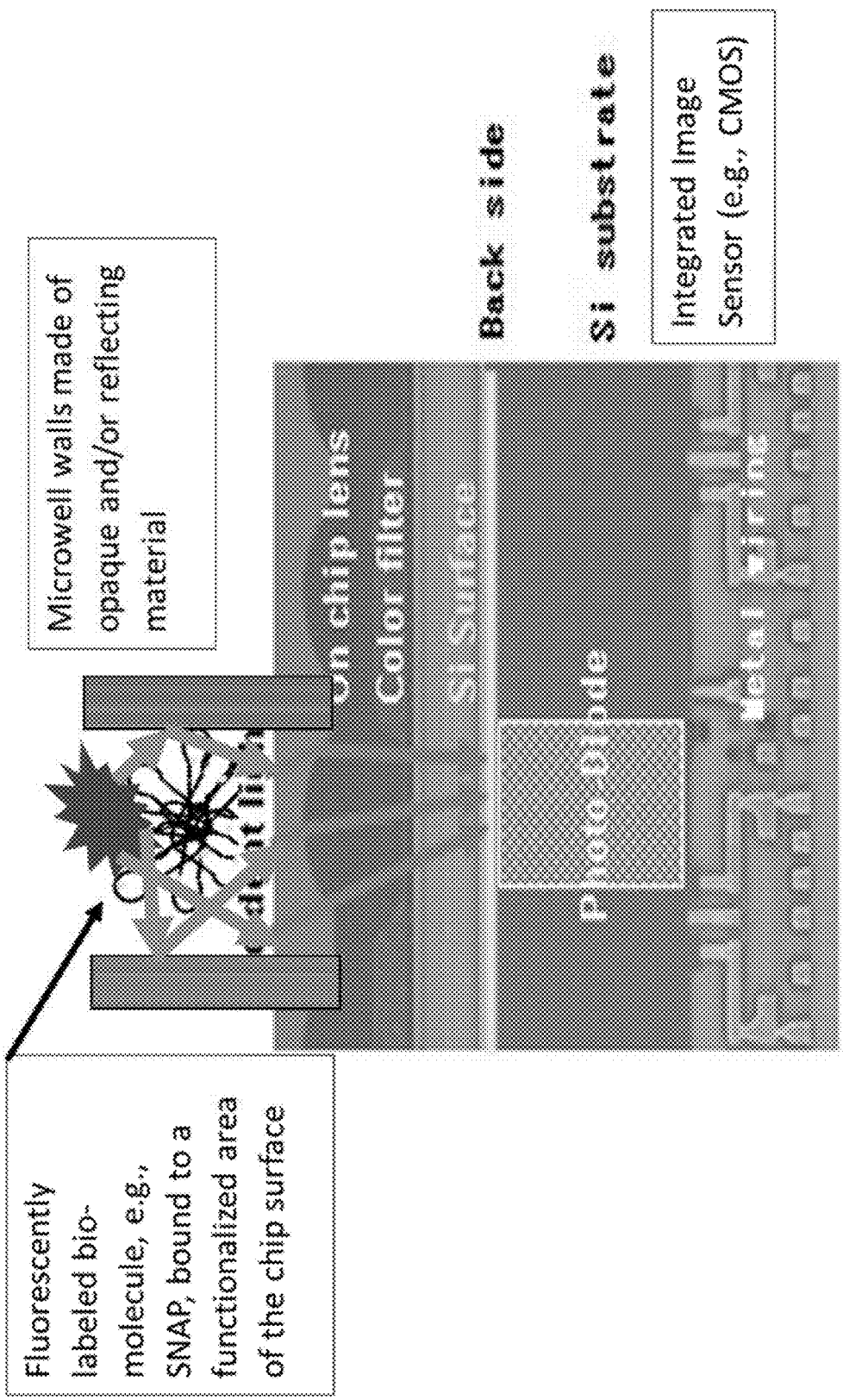
FIG. 7 illustrates a cross-sectional view of one pixel of a light-sensing device with fluorescently labeled biomolecules bound to a functionalized area of the chip surface (e.g., immobilized SNAPs), a probe, and a micro-well to prevent cross talk between pixels, in accordance with disclosed embodiments.

Example 3: Array of Light-Sensing Devices with Fluorescently Labeled Biomolecules Bound to a Functionalized Area of the Chip Surface (e.g., Immobilized SNAPs), a Probe, and a Micro-Well to Prevent Cross Talk Between Pixels FIG. 7 illustrates a cross-sectional view of one pixel of a light-sensing device with fluorescently labeled biomolecules bound to a functionalized area of the chip surface (e.g., immobilized SNAPs), a probe, and a micro-well to prevent cross talk between pixels, in accordance with disclosed embodiments. The microwell walls are made of opaque and/or reflecting material. Incident light may be collected by an on-chip lens and then processed by a color filter. When the incident light hits the silicon surface on the backside of the silicon substrate, a photo-diode can collect the photons of the incident light and convert the photons into electrons. In some embodiments, an on-chip lens may not be needed.

Figure 8:
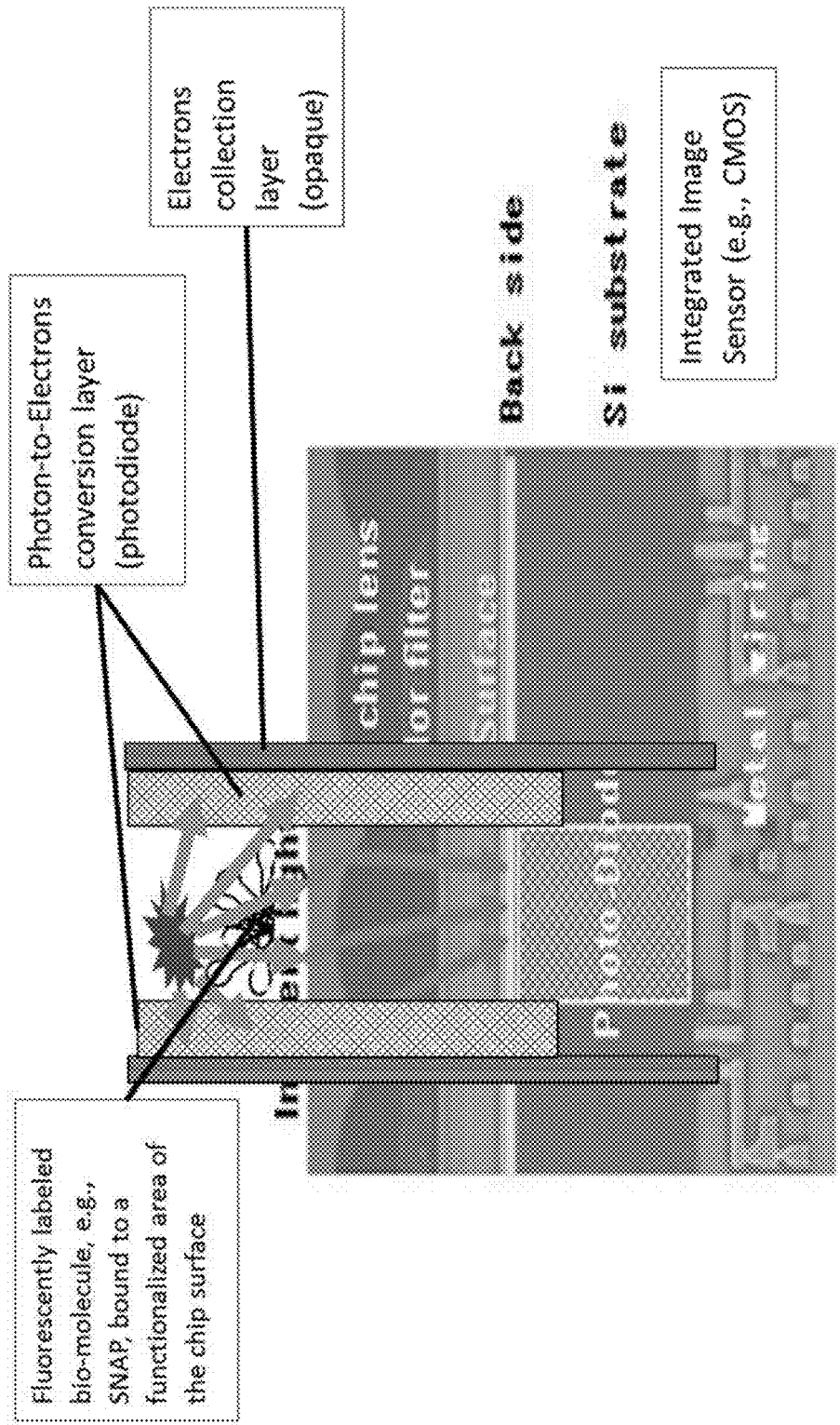
FIG. 8 illustrates a cross-sectional view of one pixel of a light-sensing device with fluorescently labeled biomolecules bound to a functionalized area of the chip surface (e.g., immobilized SNAPs), a probe, and a micro-well to increase collection and conversion of emitted light, in accordance with disclosed embodiments.

Example 4: Array of Light-Sensing Devices with Fluorescently Labeled Biomolecules Bound to a Functionalized Area of the Chip Surface (e.g., Immobilized SNAPs), a Probe, and a Micro-Well to Increase Collection and Conversion of Emitted Light FIG. 8 illustrates a cross-sectional view of one pixel of a light-sensing device with fluorescently labeled biomolecules bound to a functionalized area of the chip surface (e.g., immobilized SNAPs), a probe, and a micro-well to increase collection and conversion of emitted light, in accordance with disclosed embodiments. The microwell walls comprise photon-to-electron conversions layers that function as photodiodes, and electron collection layers that are made of an opaque material. Incident light may be collected by an on-chip lens and then processed by a color filter. When the incident light hits the silicon surface on the backside of the silicon substrate, a photo-diode can collect the photons of the incident light and convert the photons into electrons. In addition, the microwell walls also collect and convert emitted light. In some embodiments, an on-chip lens may not be needed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition, comprising:
    a. a substrate;
    b. a first structured nucleic acid particle coupled to the substrate, wherein a biological entity is coupled to the first structured nucleic acid particle; and
    c. a fluorescent detection agent, wherein the fluorescent detection agent comprises an affinity reagent attached to a second structured nucleic acid particle, wherein the affinity reagent is bound to the biological entity, wherein the first structured nucleic acid particle is coupled to the substrate by binding between a first oligonucleotide and a second oligonucleotide, wherein the first oligonucleotide is attached to the substrate, and wherein the second oligonucleotide comprises a strand of the structured nucleic acid particle.

2. The composition of claim 1, wherein the biological entity comprises a protein.

3. The composition of claim 1, wherein the biological entity comprises a small molecule, a DNA, an RNA, a glycoprotein, a metabolite, a carbohydrate, an enzyme, or an antibody.

4. The composition of claim 1, wherein the biological entity consists essentially of a single protein.

5. The composition of claim 1, wherein the first structured nucleic acid particle comprises a nucleic acid origami.

6. The composition of claim 5, wherein the nucleic acid origami comprises a long nucleic acid strand and one or more short nucleic acid strands.

7. The composition of claim 6, wherein the nucleic acid origami comprises at least 100 short nucleic acid strands.

8. The composition of claim 7, wherein the nucleic acid origami comprises a landing surface that preferentially contacts the substrate.

9. The composition of claim 1, wherein the second structured nucleic acid particle comprises a nucleic acid origami.

10. The composition of claim 1, wherein the first structured nucleic acid particle comprises a short nucleic acid strand hybridized to a long nucleic acid strand.

11. The composition of claim 1, wherein the fluorescent detection agent comprises two or more affinity reagents coupled to the second structure nucleic acid particle.

12. The composition of claim 1, wherein the affinity reagent comprises an antibody or an antibody fragment.

13. The composition of claim 1, wherein the affinity reagent comprises an aptamer.

14. The composition of claim 1, wherein the affinity reagent comprises a mini-peptide binder or a peptimer.

15. The composition of claim 1, wherein the affinity reagent comprises a known degree of nonspecificity.

16. The composition of claim 1, wherein the substrate comprises silicon, silica, fused silica, quartz, or glass.

17. The composition of claim 1, wherein the substrate comprises a microstructure that is coupled to the first structured nucleic acid particle.

18. The composition of claim 1, wherein the substrate further comprises a passivating layer.

19. The composition of claim 1, wherein the substrate further comprises a functionalized region.

20. The composition of claim 1, wherein the functionalized region comprises a filamentous molecule.

21. The composition of claim 20, wherein the filamentous molecule comprises an oligonucleotide or a nanoparticle.

22. The composition of claim 20, wherein the first structured nucleic acid particle comprises a moiety that is bound to the filamentous molecule.

23. The composition of claim 1, wherein the substrate comprises a light-sensing device.

24. The composition of claim 23, wherein the light-sensing device comprises a charge-coupled device, a complementary metal-oxide semiconductor sensor, a charge injection device, or a JOT image sensor.

\* \* \* \* \*